(12) United States Patent
Koenemann et al.

(10) Patent No.: US 11,441,036 B2
(45) Date of Patent: Sep. 13, 2022

(54) 2-PHENYLPHENOXY-SUBSTITUTED PERYLENE BISIMIDE COMPOUNDS AND THEIR USE

(71) Applicant: BASF SE, Ludwigshafen am Rhein (DE)

(72) Inventors: Martin Koenemann, Ludwigshafen (DE); Gerhard Wagenblast, Wachenheim (DE); Sorin Ivanovici, Ludwigshafen (DE); Martina Mitgude, Ludwigshafen (DE)

(73) Assignee: BASF SE

( * ) Notice: Subject to any disclaimer, the term of this patent is extended or adjusted under 35 U.S.C. 154(b) by 828 days.

(21) Appl. No.: 16/339,653

(22) PCT Filed: Oct. 5, 2017

(86) PCT No.: PCT/EP2017/075274
§ 371 (c)(1),
(2) Date: Apr. 4, 2019

(87) PCT Pub. No.: WO2018/065502
PCT Pub. Date: Apr. 12, 2018

(65) Prior Publication Data
US 2020/0071531 A1 Mar. 5, 2020

(30) Foreign Application Priority Data

Oct. 6, 2016 (EP) .................................. 16192617

(51) Int. Cl.
| | |
|---|---|
| C09B 67/22 | (2006.01) |
| C09B 5/62 | (2006.01) |
| F21K 9/64 | (2016.01) |
| C09D 11/037 | (2014.01) |
| C09K 11/06 | (2006.01) |
| F21Y 115/10 | (2016.01) |

(52) U.S. Cl.
CPC ............ C09B 5/62 (2013.01); C09B 67/0033 (2013.01); C09D 11/037 (2013.01); C09K 11/06 (2013.01); F21K 9/64 (2016.08); C09K 2211/1018 (2013.01); F21Y 2115/10 (2016.08)

(58) Field of Classification Search
CPC ....... C09B 5/62; C09B 67/0033; C09K 11/06; C09K 2211/1018; C09D 11/037; F21Y 2115/10; F21K 9/64
See application file for complete search history.

(56) References Cited

U.S. PATENT DOCUMENTS

| | | | |
|---|---|---|---|
| 5,998,925 A | 12/1999 | Shimizu et al. | |
| 6,066,861 A | 5/2000 | Hoehn et al. | |
| 6,245,259 B1 | 6/2001 | Hoehn et al. | |
| 6,429,583 B1 | 8/2002 | Levinson et al. | |
| 6,576,930 B2 | 6/2003 | Reeh et al. | |
| 6,669,866 B1 | 12/2003 | Kummer et al. | |
| 6,765,237 B1 | 7/2004 | Doxsee et al. | |
| 6,809,347 B2 | 10/2004 | Tasch et al. | |
| 6,812,500 B2 | 11/2004 | Reeh et al. | |
| 6,943,380 B2 | 9/2005 | Ota et al. | |
| 7,119,224 B2 | 10/2006 | Schroeder et al. | |
| 7,252,785 B2 | 8/2007 | Parker et al. | |
| 7,267,787 B2 | 9/2007 | Dong et al. | |
| 7,311,858 B2 | 12/2007 | Wang et al. | |
| 7,741,487 B2 | 6/2010 | Koenemann et al. | |
| 7,795,431 B2 | 9/2010 | Pschirer et al. | |

(Continued)

FOREIGN PATENT DOCUMENTS

| | | |
|---|---|---|
| CN | 104619794 A | 5/2015 |
| CN | 107428775 A | 12/2017 |

(Continued)

OTHER PUBLICATIONS

U.S. Appl. No. 14/673,992, filed Mar. 31, 2015, US 2015-0274977 A1, Hansulrich Reisacher, et al.

(Continued)

*Primary Examiner* — Bijan Ahvazi
(74) *Attorney, Agent, or Firm* — Faegre Drinker Biddle & Reath LLP

(57) ABSTRACT

The present invention relates to a perylene bisimide compound of formula (I)

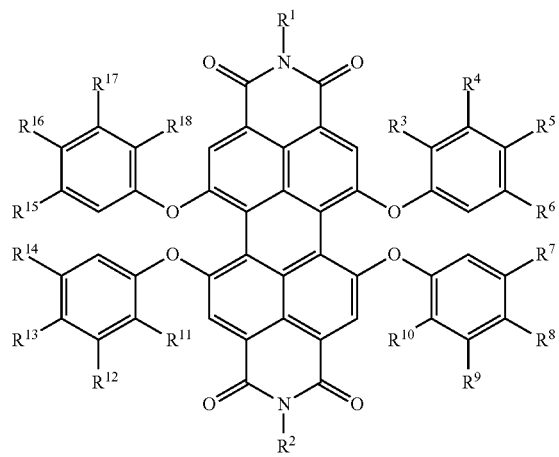

or a mixture thereof. The present invention also relates to the use of the compound in color converters, to the color converters and their use, and to lighting devices containing at least one LED and at least one of the color converters. The present invention also relates to a printing ink formulation for security printing containing at least one of the phenoxy-substituted perylene bisimide compounds.

16 Claims, No Drawings

(56) References Cited

U.S. PATENT DOCUMENTS

| | | | |
|---|---|---|---|
| 7,799,920 B2 | 9/2010 | Koenemann et al. | |
| 8,052,899 B2 | 11/2011 | Qu et al. | |
| 8,071,775 B2 | 12/2011 | Koenemann et al. | |
| 8,084,603 B2 | 12/2011 | Koenemann | |
| 8,231,809 B2 | 7/2012 | Pschirer et al. | |
| 8,309,728 B2 | 11/2012 | Koenemann | |
| 8,501,046 B2 | 8/2013 | Pschirer et al. | |
| 8,611,070 B2 | 12/2013 | Ivanovici et al. | |
| 8,674,104 B2 | 3/2014 | Koenemann et al. | |
| 9,236,535 B2 | 1/2016 | Wagenblast et al. | |
| 9,406,848 B2 | 8/2016 | Koenemann et al. | |
| 9,512,354 B2 | 12/2016 | Koenemann et al. | |
| 9,577,243 B2 | 2/2017 | Schmidt et al. | |
| 9,711,665 B2 | 7/2017 | Wagenblast et al. | |
| 9,790,423 B2 | 10/2017 | Koenemann et al. | |
| 9,919,999 B2 | 3/2018 | Koenemann et al. | |
| 10,214,525 B2 | 2/2019 | Koenemann et al. | |
| 10,230,023 B2 | 3/2019 | Koenemann et al. | |
| 2008/0167467 A1 | 7/2008 | Konemann et al. | |
| 2014/0076397 A1* | 3/2014 | Wagenblast | H01L 31/055 428/522 |
| 2015/0002591 A1 | 1/2015 | Kozee et al. | |
| 2015/0372240 A1* | 12/2015 | Lub | H05B 33/12 546/37 |
| 2016/0101639 A1 | 4/2016 | Kozee et al. | |
| 2017/0183295 A1* | 6/2017 | Koenemann | C09K 11/7774 |
| 2018/0065980 A1 | 3/2018 | Koenemann et al. | |
| 2019/0010165 A1 | 1/2019 | Koenemann et al. | |
| 2019/0023905 A1 | 1/2019 | Konemann et al. | |

FOREIGN PATENT DOCUMENTS

| | | |
|---|---|---|
| EP | 2807220 A2 | 12/2014 |
| EP | 3 072 887 A1 | 9/2016 |
| EP | 3274334 A1 | 1/2018 |
| JP | 2014-519191 A | 8/2014 |
| JP | 2016-513338 A | 5/2016 |
| JP | 2017-523124 A | 8/2017 |
| JP | 2018-512418 A | 5/2018 |
| KR | 10-2017-0129766 A | 11/2017 |
| TW | 201708229 A | 3/2017 |
| WO | WO 02/11214 A1 | 2/2002 |
| WO | WO 2005/052087 A1 | 6/2005 |
| WO | WO 2007/006717 A1 | 1/2007 |
| WO | WO 2012/042438 A1 | 4/2012 |
| WO | WO 2012/152812 A1 | 11/2012 |
| WO | WO 2012/168395 A1 | 12/2012 |
| WO | 2013/112899 A2 | 8/2013 |
| WO | WO 2014/122549 A1 | 8/2014 |
| WO | WO 2014/131628 A1 | 9/2014 |
| WO | WO 2015/019270 A1 | 2/2015 |
| WO | WO 2015/169935 A1 | 11/2015 |
| WO | WO 2016/151068 A1 | 9/2016 |
| WO | WO 2017/121833 A1 | 7/2017 |

OTHER PUBLICATIONS

U.S. Appl. No. 16/069,954, filed Jul. 13, 2018, US 2019-0023905 A1, Martin Koenemann, et al.

International Preliminary Report on Patentability received for PCT Patent Application No. PCT/EP2017/075274, dated Oct. 1, 2018, 4 pages.

International Search Report dated Dec. 4, 2017 in PCT/EP2017/075274 filed Oct. 5, 2017.

Seybold, G. et al, "New Perylene and Violanthrone Dyestuffs for Fluorescent Collectors," Dyes and Pigments, vol. 11, 1989, pp. 303-317.

* cited by examiner

2-PHENYLPHENOXY-SUBSTITUTED PERYLENE BISIMIDE COMPOUNDS AND THEIR USE

FIELD OF THE INVENTION

The present invention relates to novel perylene bisimide compounds carrying in each bay position (1,6,7,12-positions) of the conjugated perylene core a 2-phenylphenoxy substituent. In particular, the present invention relates to the use of said compound(s) in color converters, to said color converters and their use and to lighting devices comprising at least one LED and at least one of said color converters. The present invention also relates to a printing ink formulation for security printing comprising at least one of said phenoxy-substituted perylene bisimide compounds.

BACKGROUND OF THE INVENTION

LEDs (light-emitting diodes) are an important class of devices that convert electric energy into light and are increasingly replacing conventional light sources such as incandescent lamps and fluorescent lamps. They provide light in a more efficient manner, since they have substantially higher conversion efficiencies than incandescent lamps, longer lifetimes and smaller size and use less electrical power than conventional light sources. They are used in many different lighting applications such as general lighting systems, traffic signals, automotive lighting, or backlighting.

Light emission of LEDs is based on the recombination of electron-hole pairs (excitons) in the junction region of a pn junction poled in forward direction in a semiconductor. LEDs generate light in a narrow spectral wavelength range, where the center emission peak wavelength is determined by the semiconductor materials forming the active layer. For examples blue to green LEDs can be produced using nitride semiconductors such as AlN (aluminium nitride), GaN (gallium nitride), InN (indium nitrirde) or InGaN (indium gallium nitride); red LEDs can be produced using semiconductors such as GaP (gallium phosphide), AlGaAs (aluminium gallium arsenide) or GaAsP (gallium arsenide phosphide).

White light illumination is often required for general lighting purpose as well as in a wide range of other applications such as liquid-crystal display backlighting. Currently, there exists no LED which can emit white light directly. As it is well known, red, green and blue LEDs can be configured to generate white light. Because of the different brightnesses and operating conditions for the different LEDs, the multi-LED is technically complex and therefore expensive. Moreover, component miniaturization of the multi-LED is severely limited.

A further approach for LED based white-light sources is depositing a wavelength-converting material such as a yellowish phosphor over the emission surface of a blue LED. Blue photons generated in the LED either pass unchanged through the yellow phosphor layer or are converted into yellow photons in the yellow phosphor layer. The unabsorbed blue light is mixed with the yellow light to mimic white light.

One type of white light sources based on LED is constructed from a blue LED, where inorganic phosphor material is applied directly and without intervening space to the LED chip. This type of LED is also referred to as "phosphor on chip" LED or phosphor-converted LED. A drawback is that the phosphor materials are subject to relatively high thermal and radiative stress. A most commonly used phosphor for this purpose is cerium-doped yttrium aluminum garnet (also referred to as Ce:YAG). However, phosphor-converted LEDs using Ce:YAG emit cool white light having a correlated color temperature (CCT) above 6,000 K and poor color rendering (CRI) around 70, because the red component in the spectrum of the generated white light is too weak. Thus, this type of white light source does not meet the requirements of general lighting applications. To obtain a warm-white light, the emission spectrum has to be red-shifted, for example by adding other phosphors that emit in the red portion of the visible spectrum. Inorganic red phosphors are based on rare-earth phosphors which are expensive and, in addition, not enviromental friendly. Also blends of quantum dots with inorganic phosphors can be used to tune the wavelength of the emitted white light.

The materials and thickness selected for the phosphor layer have an influence on the CCT of the emitted white light. Even small variations in the ratio of blue to yellow light and/or in the thickness/uniformity of the phosphor layer cause huge variations in the CCT.

A further type of white light sources based on LEDs is constructed from a blue LED in combination with a color converter (also referred to simply as "converter"), where the color converter is at a certain distance from the blue LED chip. Such structures are referred to as "remote phosphor" or "remote-phosphor" LED. The color converter generally comprises at least one polymer and at least one organic fluorescent dye. Generally, organic fluorescent dyes are sensitive to relative high temperatures and radiation but the spatial distance between the primary light source, i.e. the blue LED, and the color converter reduces the stress resulting from heat and radiation to such an extent that the requirements on the stability can be achieved by suitable organic fluorescent dyes. Organic fluorescence dyes often have strong and tunable emissive properties. According to this approach, a mixture of yellow organic and red organic fluorescent dyes are often used to broaden the emission spectrum, which results in a warm-white light. White light sources based on remote phosphor LEDs cover almost the whole visible spectrum and part of the near infrared spectrum, so that remote phosphor LEDs are suitable for general lighting. However, one drawback of remote-phosphor LEDs is that they are less efficient than phosphor-converted LEDs, because a large portion of the red phosphor emission occurs above 700 nm, which is beyond the sensitivity of the human eye.

Another type of white light sources based on LEDs is constructed from a phosphor-converted LED pumped by blue LED in combination with a color converter comprising at least one organic fluorescent dye, where the phosphor-converted LED and the color converter are in a spatial distance (remote phosphor arrangement). This type is also referred to as hybrid LED.

Phosphor-converted LEDs pumped by blue LED provide cool-white light suitable as backlight for LCDs (liquid crystal displays). Current processes do not provide phosphor-converted LEDs with consistent CCT due to variations in manufacturing process. For backlight applications, variations in CCT can become a significant problem and backlight manufacturer only use LEDs with a close matching to the spectra needed for backlights. LEDs which do not meet these requirements are regarded as "defective products". Currently, large amounts of "defective" LEDs have been available in the market. It would be desirable to use them for other applications, especially for general lighting applications. Thus, there is an ongoing need for improving the performance characteristics of LEDs not suitable as backlights, especially improving CCT and/or CRI which are key factors in the choice of light sources for general lighting.

G. Seybold and G. Wagenblast describe in Dyes and Pigments, 1989, 303-317, dyes of the peryleneimide type. It is mentioned that N,N'-bis(2,6-diisopropylphenyl)-1,6,7,12-tetraphenoxyperylene-3,4:9,10-tetracarboxdiimide has an excellent fastness to weathering and a high fluorescence quantum yield.

WO 2007/006717 discloses substituted rylene derivatives and their use for coloring high molecular weight organic and inorganic materials, for producing aqueous polymer dispersions which absorb and/or emit electromagnetic radiation, for obtaining markings and inscriptions which absorb infrared light and are invisible to the human eye, as infrared absorbers for heat management, as IR laser beam-absorbent materials in the fusion bonding of plastics parts, for laser marking and laser inscription, as semiconductors in organic electronics, as filters and emitters in display applications, as emitters in chemiluminescence applications, as labeling groups in detection methods and as active components in photovoltaics. Perylene diimides carrying 2-phenylphenoxy at each bay position of the perylene core are not disclosed.

EP 3072887 describes N,N'-bis(2,6-diisopropylphenyl)-1,7-di(2,6-diphenyl-phenoxy)perylene-3,4;9,10-tetracarbox-imide, N,N'-bis(2,6-diisopropylphenyl)-1,6-di(2,6-diphenylphenoxy)perylene-3,4;9,10-tetracarboximide and the use of said compound(s) in color converters for improving the luminous efficacy of white-light emitting diodes.

Unpublished EP 16151228.0 (post-published WO 2017/121833) describes perylene bisimide compounds with rigid 2,2'-biphenoxy bridges that are useful as fluorescent dye in a color converter for improving luminous efficacy of LEDs. The compounds are also suitable as absorber for security printing.

WO 2012/042438 describes color converters comprising perylene tetracarboxylic acid diimides in a polymeric material comprising a polyester having an aromatic moiety incorporated in the polymer backbone. The perylene tetracarboxylic acid diimides carry up to four substituents at the bay-positions of the perylene core, the substituents being selected from fluorine, methoxy, unsubstituted $C_1$-$C_{16}$-alkyl and phenoxy which is optionally substituted by fluorine, methoxy or $C_1$-$C_{16}$-alkyl.

WO 2012/152812 describes color converters that may comprise perylene tetracarboxylic acid diimides carrying in each bay position a phenoxy group which is unsubstituted or substituted by 1, 2 or 3 linear or branched alkyl groups.

WO 2015/169935 describes cyanated perylene compounds and their use as fluorescent dye, in particular in color converters for blue LEDs.

WO 2014/122549 describes perylenetetracarboxylic acid diimides as organic red emitter and light emitting devices using the same. The perylene tetracarboxylic acid diimides carry up to four substituents at the bay positions of the perylene core, the substituents being selected from fluorine, chlorine, methoxy, unsubstituted $C_1$-$C_{16}$-alkyl and oxygen-containing alkyl with up to 16 carbon atoms and phenoxy which is optionally substituted by fluorine, methoxy or $C_1$-$C_{16}$-alkyl with the proviso that at least two of the substituents at the bay positions of the perylene core are phenoxy having at least one group selected from fluorine and chlorine.

Thus, the problem underlying the present invention is to provide novel organic fluorescent dyes having improved application properties. In particular, the novel fluorescent dyes should have at least one of the following properties:

Suitability for down-converting cool white LED light having a correlated color temperature between 6,000 K to 20 000 K into white light with a lower correlated color temperature;
suitability for down-converting blue LED light into white light;
high photostability;
high heat stability;
high chemical stability with respect to moisture and oxygen;
high fluorescence quantum yield in polymeric matrices;
high compatibility with the LED production operation;
suitability as fluorescent dye for security printing;
good fastness to chemicals, in particular fastness to bleaching with hypochlorite and fastness to solvents (like toluene, acetone or dichloromethane);
good fastness to boiling water;
high compatibility with a multiplicity of formulations, in particular printing ink formulations used in security printing and thermoplastic polymer formulations used for laser-welding.

This and further problems are solved by the perylene bisimide compounds of the formula (I) described below.

SUMMARY OF THE INVENTION

In a first aspect, the invention provides a novel perylene bisimide compound of the formula (I)

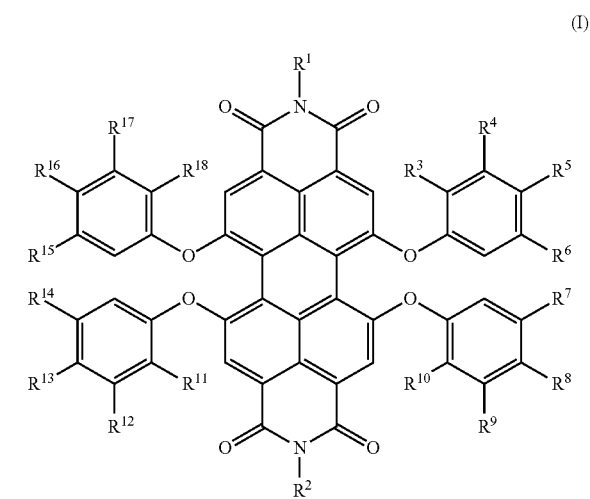

wherein
$R^1$ and $R^2$, independently of each other, are selected from the group consisting of hydrogen, in each case unsubstituted or substituted $C_1$-$C_{30}$-alkyl, polyalkyleneoxy, $C_1$-$C_{30}$-alkoxy, $C_1$-$C_{30}$-alkylthio, $C_3$-$C_{20}$-cycloalkyl, $C_3$-$C_{20}$-cycloalkyloxy, $C_6$-$C_{24}$-aryl and $C_6$-$C_{24}$-aryloxy;
$R^3$, $R^{10}$, $R^{11}$ and $R^{18}$, independently of each other, are selected from phenyl and phenyl, which is substituted by one, two, three, four or five radicals L, where L is selected from halogen, cyano, hydroxyl, mercapto, —NR$^{Ar1}$COR$^{Ar2}$, unsubstituted or substituted $C_1$-$C_{30}$-alkyl, polyalkyleneoxy, $C_1$-$C_{30}$-alkoxy, $C_1$-$C_{30}$-alkylthio, $C_3$-$C_{20}$-cycloalkyl, $C_3$-$C_{20}$-cycloalkoxy, $C_6$-$C_{24}$-aryl, $C_6$-$C_{24}$-aryloxy and $C_6$-$C_{24}$-arylthio;
$R^4$, $R^5$, $R^6$, $R^7$, $R^8$, $R^9$, $R^{12}$, $R^{13}$, $R^{14}$, $R^{15}$, $R^{16}$, and $R^{17}$ independently of each other, are selected from the group consisting of hydrogen, halogen, cyano, hydroxyl, mercapto, —NR$^{Ar1}$COR$^{Ar2}$, —CONR$^{Ar1}$R$^{Ar2}$, —SO$_2$NR$^{Ar1}$R$^{Ar2}$, —COOR$^{Ar1}$, —SO$_3$R$^{Ar2}$, in each case unsubstituted or substituted C$_1$-C$_{30}$-alkyl, polyalkyleneoxy, C$_1$-C$_{30}$-alkoxy, C$_1$-C$_{30}$-alkylthio, C$_3$-C$_{20}$-cycloalkyl, C$_3$-C$_{20}$-cycloalkoxy, C$_6$-C$_{24}$-aryl, C$_6$-C$_{24}$-aryloxy and C$_6$-C$_{24}$-arylthio, where R$^4$ and R$^5$, R$^5$ and R$^6$, R$^7$ and R$^8$, R$^8$ and R$^9$, R$^{12}$ and R$^{13}$, R$^{13}$ and R$^{14}$, R$^{14}$ and R$^{15}$, R$^{15}$ and R$^{16}$, and/or R$^{16}$ and R$^{17}$ together with the carbon atoms to which they are bonded, may also form a fused aromatic or non-aromatic carbon ring system wherein the fused ring system is unsubstituted or substituted; where R$^{Ar1}$ and R$^{Ar2}$, independently of each other, are hydrogen, unsubstituted or substituted C$_1$-C$_{18}$-alkyl, unsubstituted or substituted C$_3$-C$_{20}$-cycloalkyl, unsubstituted or substituted heterocyclyl, unsubstituted or substituted C$_6$-C$_{20}$-aryl or unsubstituted or substituted heteroaryl.

In a further aspect, the present invention provides a color converter comprising at least one compound of the formula (I) or mixtures thereof as fluorescent dye and at least one polymer as a matrix, wherein the polymer is selected from the group consisting of polystyrene, polycarbonate, polymethylmethacrylate, polyvinyl pyrrolidone, polymethacrylate, polyvinyl acetate, polyvinyl chloride, polybutene, silicone, polyacrylate, epoxy resin, polyvinyl alcohol, poly(ethylene vinylalcohol)-copolymer, polyacrylonitrile, polyvinylidene chloride, polystyreneacrylonitrile, polybutylene terephthalate, polyethylene terephthalate, polyvinyl butyrate, polyvinyl chloride, polyamides, polyoxymethylenes, polyimides, polyetherimides and mixtures thereof, preferably polystyrene, polycarbonate or polyethylene terephthalate.

In a further aspect, the present invention provides the use of a color converter as defined above, for converting light generated by a blue LED with a center wavelength of emission between 420 nm and 480 nm into light of a second, longer wavelength.

In a further aspect, the present invention provides the use of a color converter as defined above, for conversion of light generated by a cool white LED having a correlated color temperature between 6,000 K and 20,000 K to provide white light having a lower correlated color temperature.

In a further aspect, the present invention provides a lighting device comprising at least one blue LED with a center wavelength of emission from 420 nm to 480 nm and at least one color converter as defined above, wherein LED and color converter are in a remote phosphor arrangement.

In a further aspect, the present invention provides a lighting device comprising at least one cool white LED having a correlated color temperature between 6,000 K and 20,000 K and at least one color converter as defined above, wherein LED and color converter are in a remote phosphor arrangement.

In a further aspect, the present invention provides the use of a compound of the formula (I) or a mixture thereof in color converters for converting light emitted from a light source, in particular a light source selected from LEDs and OLEDs (organic light emitting diodes), into light of a second, longer wavelength, for coloring coatings, printing inks and plastics, producing aqueous polymer dispersions which absorb and/or emit electromagnetic radiation, for data storage, for optical labels, for security labels in documents and for brand protection or as a fluorescent label for biomolecules.

In a further aspect, the present invention provides the use of a perylene bisimide compound of the formula (I) or a mixture thereof as defined above in security inks for security printing.

In a further aspect, the present invention provides a printing ink formulation for security printing, comprising at least one compound of the formula (I) or a mixture thereof as defined above.

EMBODIMENTS OF THE INVENTION

Specially, the invention comprises the following preferred embodiments:

1. A perylene bisimide compound of the formula (I)

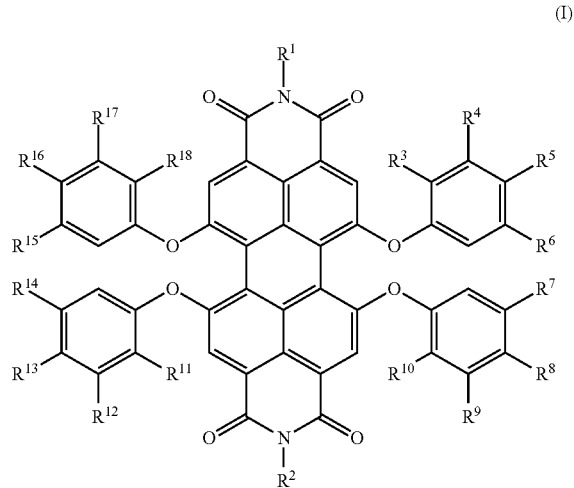

wherein

R$^1$ and R$^2$, independently of each other, are selected from the group consisting of hydrogen,
  in each case unsubstituted or substituted C$_1$-C$_{30}$-alkyl, polyalkyleneoxy, C$_1$-C$_{30}$-alkoxy, C$_1$-C$_{30}$-alkylthio, C$_3$-C$_{20}$-cycloalkyl, C$_3$-C$_{20}$-cycloalkyloxy, C$_6$-C$_{24}$-aryl and C$_6$-C$_{24}$-aryloxy;

R$^3$, R$^{10}$, R$^{11}$ and R$^{18}$, independently of each other, are selected from phenyl and phenyl, which is substituted by one, two, three, four or five radicals L, wherein L is selected from halogen, cyano, hydroxyl, mercapto, —NR$^{Ar1}$COR$^{Ar2}$, unsubstituted or substituted C$_1$-C$_{30}$-alkyl, polyalkyleneoxy, C$_1$-C$_{30}$-alkoxy, C$_1$-C$_{30}$-alkylthio, C$_3$-C$_{20}$-cycloalkyl, C$_3$-C$_{20}$-cycloalkoxy, C$_6$-C$_{24}$-aryl, C$_6$-C$_{24}$-aryloxy and C$_6$-C$_{24}$-arylthio;

R$^4$, R$^5$, R$^6$, R$^7$, R$^8$, R$^9$, R$^{12}$, R$^{13}$, R$^{14}$, R$^{15}$, R$^{16}$, and R$^{17}$ independently of each other, are selected from the group consisting of hydrogen, halogen, cyano, hydroxyl, mercapto, —NR$^{Ar1}$COR$^{Ar2}$, —CONR$^{Ar1}$R$^{Ar2}$, —SO$_2$NR$^{Ar1}$R$^{Ar2}$, —COOR$^{Ar1}$, —SO$_3$R$^{Ar2}$,
  in each case unsubstituted or substituted C$_1$-C$_{30}$-alkyl, polyalkyleneoxy, C$_1$-C$_{30}$-alkoxy, C$_1$-C$_{30}$-alkylthio, C$_3$-C$_{20}$-cycloalkyl, C$_3$-C$_{20}$-cycloalkoxy, C$_6$-C$_{24}$-aryl, C$_6$-C$_{24}$-aryloxy and C$_6$-C$_{24}$-arylthio,
  where R$^4$ and R$^5$, R$^5$ and R$^6$, R$^7$ and R$^8$, R$^8$ and R$^9$, R$^{12}$ and R$^{13}$, R$^{13}$ and R$^{14}$, R$^{14}$ and R$^{15}$, R$^{15}$ and R$^{16}$, and/or R$^{16}$ and R$^{17}$ together with the carbon atoms to which they are bonded, may also form a fused aromatic or non-aromatic carbon ring system wherein the fused ring system is unsubstituted or substituted;

where

R$^{Ar1}$ and R$^{Ar2}$, each independently of each other, are hydrogen, unsubstituted or substituted C$_1$-C$_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl.

2. The compound as defined in embodiment 1, where $R^1$ and $R^2$ in formula (I) independently of each other are selected from $C_1$-$C_{10}$-alkyl, which is unsubstituted or substituted by $C_6$-$C_{10}$-aryl which in turn is unsubstituted or substituted by 1, 2 or 3 $C_1$-$C_{10}$-alkyl, $C_3$-$C_8$-cycloalkyl, which is unsubstituted or substituted by 1, 2 or 3 $C_1$-$C_{10}$-alkyl, and $C_6$-$C_{10}$-aryl which is unsubstituted or substituted by 1, 2 or 3 $C_1$-$C_{10}$-alkyl.

3. The compound as defined in embodiment 2, where $R^1$ and $R^2$ in formula (I) independently of each other are selected from $C_1$-$C_8$-alkyl, $C_3$-$C_8$-cycloalkyl, which is unsubstituted or substituted by 1, 2 or 3 $C_1$-$C_6$-alkyl, and $C_6$-$C_{10}$-aryl which is unsubstituted or substituted by 1, 2 or 3 $C_1$-$C_6$-alkyl.

4. The compound as defined in embodiment 3, where $R^1$ and $R^2$ in formula (I) have the same meaning and are phenyl which is unsubstituted or substituted by 1, 2 or 3 $C_1$-$C_6$-alkyl.

5. The compound as defined in any of the preceding embodiments, where $R^3$, $R^{10}$, $R^{11}$ and $R^{18}$, independently of each other, are selected from phenyl and phenyl which is substituted by 1, 2 or 3 radicals L selected from $C_1$-$C_6$-alkyl, $C_1$-$C_6$-alkoxy-$C_1$-$C_6$-alkyl and $C_1$-$C_6$-alkoxy, preferably selected from phenyl and phenyl which is substituted by 1 or 2 radicals selected from $C_1$-$C_6$-alkyl, $C_1$-$C_6$-alkoxy-$C_1$-$C_6$-alkyl and $C_1$-$C_6$-alkoxy.

6. The compound as defined in embodiment 5, where $R^3$, $R^{10}$, $R^{11}$ and $R^{18}$, independently of each other, are selected from phenyl and phenyl which is substituted by 1 or 2 $C_1$-$C_6$-alkyl, preferably phenyl.

7. The compound as defined in any of the preceding embodiments, wherein $R^4$, $R^5$, $R^6$, $R^7$, $R^8$, $R^9$, $R^{12}$, $R^{13}$, $R^{14}$, $R^{15}$, $R^{16}$ and $R^{17}$, independently of each other, are selected from hydrogen, halogen, $C_1$-$C_{18}$-alkyl, $C_6$-$C_{10}$-aryl, $C_6$-$C_{10}$-aryl-$C_1$-$C_{10}$-alkylene, $C_6$-$C_{10}$-aryloxy and $C_6$-$C_{10}$-arylthio, where the aryl moiety of $C_6$-$C_{10}$-aryl, $C_6$-$C_{10}$-aryl-$C_1$-$C_{10}$-alkylene, $C_6$-$C_{10}$-aryloxy, and $C_6$-$C_{10}$-arylthio is unsubstituted or substituted by one or more $C_1$-$C_{10}$-alkyl,
and where $R^5$ and $R^6$, $R^7$ and $R^8$, $R^{13}$ and $R^{14}$ and/or $R^{15}$ and $R^{16}$, together with the carbon atoms to which they are bonded, may also form a fused benzene ring wherein the fused benzene ring is unsubstituted or substituted.

8. The compound as defined in any of the preceding embodiments, wherein $R^4$, $R^5$, $R^6$, $R^7$, $R^8$, $R^9$, $R^{12}$, $R^{13}$, $R^{14}$, $R^{15}$, $R^{16}$ and $R^{17}$, independently of each other, are selected from hydrogen, $C_1$-$C_6$-alkyl and $C_6$-$C_{10}$-aryl.

9. A color converter comprising at least one compound of the formula (I) or mixtures thereof as fluorescent dye as defined in the preceding embodiments and at least one polymer as a matrix, wherein the polymer is selected from the group consisting of polystyrene, polycarbonate, polymethyl methacrylate, polyvinylpyrrolidone, polymethacrylate, polyvinyl acetate, polyvinyl chloride, polybutene, silicone, polyacrylate, epoxy resin, polyvinyl alcohol, poly(ethylene vinylalcohol)-copolymer, polyacrylonitrile, polyvinylidene chloride, poly(styrene-acrylonitrile), polybutylene terephthalate, polyethylene terephthalate, polyvinyl butyrate, polyvinyl chloride, polyamides, polyoxymethylenes, polyimides, polyetherimides and mixtures thereof, preferably polystyrene, polycarbonate or polyethylene terephthalate.

10. The color converter as defined in embodiment 9, wherein the polymer consists essentially of polystyrene.

11. The color converter as defined in embodiment 9, wherein the polymer consists essentially of polycarbonate.

12. The color converter as defined in embodiment 9, wherein the polymer consists essentially of polyethylene terephthalate.

13. The color converter as defined in any of embodiments 9 to 12, wherein the color converter additionally comprises at least one inorganic white pigment as a scattering body.

14. The color converter as defined in any of embodiments 9 to 13, comprising at least one further organic fluorescent dye selected from
(i) a cyanated naphthoylbenzimidazole compound of the formula II

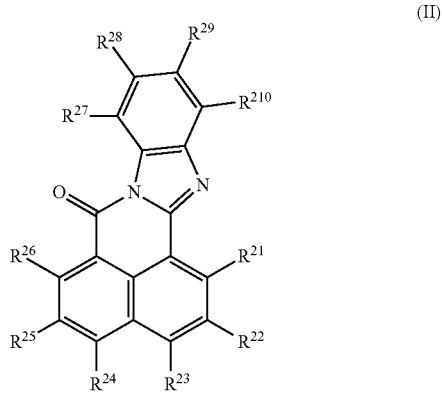

and mixtures thereof,
wherein
$R^{21}$, $R^{22}$, $R^{23}$, $R^{24}$, $R^{25}$, $R^{26}$, $R^{27}$, $R^{28}$, $R^{29}$ and $R^{210}$ are each independently hydrogen, cyano or aryl which is unsubstituted or has one or more identical or different substituents $R^{2Ar}$,
where
each $R^{2Ar}$ is independently selected from cyano, hydroxyl, mercapto, halogen, $C_1$-$C_{20}$-alkoxy, $C_1$-$C_{20}$-alkylthio, nitro, —$NR^{2Ar2}R^{2Ar3}$, —$NR^{2Ar2}COR^{2Ar3}$, —$CONR^{2Ar2}R^{2Ar3}$, —$SO_2NR^{2Ar2}R^{2Ar3}$, —$COOR^{2Ar2}$, —$SO_3R^{2Ar2}$, $C_1$-$C_{30}$-alkyl, $C_2$-$C_{30}$-alkenyl, $C_2$-$C_{30}$-alkynyl, where the three latter radicals are unsubstituted or bear one or more $R^{2a}$ groups, $C_3$-$C_8$-cycloalkyl, 3- to 8-membered heterocyclyl, where the two latter radicals are unsubstituted or bear one or more $R^{2b}$ groups, aryl, U-aryl, heteroaryl and U-heteroaryl, where the four latter radicals are unsubstituted or bear one or more $R^{2b}$ groups,
where
each $R^{2a}$ is independently selected from cyano, hydroxyl, oxo, mercapto, halogen, $C_1$-$C_{20}$-alkoxy, $C_1$-$C_{20}$-alkylthio, nitro, —$NR^{2Ar2}R^{2Ar3}$, —$NR^{2Ar2}COR^{2Ar3}$, —$CONR^{2Ar2}R^{2Ar3}$, —$SO_2NR^{2Ar2}R^{2Ar3}$, —$COOR^{2Ar2}$, —$SO_3R^{2Ar2}$, $C_3$-$C_8$-cycloalkyl, 3- to 8-membered heterocyclyl, aryl and heteroaryl, where the cycloalkyl, heterocyclyl, aryl and heteroaryl radicals are unsubstituted or bear one or more $R^{2b}$ groups;
each $R^{2b}$ is independently selected from cyano, hydroxyl, oxo, mercapto, halogen, $C_1$-$C_{20}$-alkoxy, $C_1$-$C_{20}$-alkylthio, nitro, —$NR^{2Ar2}R^{2Ar3}$, —NR$^{2Ar2}$COR$^{2Ar3}$, —CONR$^{2Ar2}$R$^{2Ar3}$, —SO$_2$NR$^{2Ar2}$R$^{2Ar3}$, —COOR$^{2Ar2}$, —SO$_3$R$^{2Ar2}$, C$_1$-C$_{18}$-alkyl, C$_2$-C$_{18}$-alkenyl, C$_2$-C$_{18}$-alkynyl, C$_3$-C$_8$-cycloalkyl, 3- to 8-membered heterocyclyl, aryl and heteroaryl, where the four latter radicals are unsubstituted or bear one or more R$^{2b1}$ groups;

each R$^{2b1}$ is independently selected from cyano, hydroxyl, mercapto, oxo, nitro, halogen, —NR$^{2Ar2}$R$^{2Ar3}$, —NR$^{2Ar2}$COR$^{2Ar3}$, —CONR$^{2Ar2}$R$^{2Ar3}$, —SO$_2$NR$^{2Ar2}$R$^{2Ar3}$, —COOR$^{2Ar2}$, —SO$_3$R$^{2Ar2}$, —SO$_3$R$^{2Ar2}$, C$_1$-C$_{18}$-alkyl, C$_2$-C$_{18}$-alkenyl, C$_2$-C$_{18}$-alkynyl, C$_1$-C$_{12}$-alkoxy, and C$_1$-C$_{12}$-alkylthio;

U is an —O—, —S—, —NR$^{2Ar1}$—, —CO—, —SO— or —SO$_2$— moiety; R$^{2Ar1}$, R$^{2Ar2}$, R$^{2Ar3}$ are each independently hydrogen, C$_1$-C$_{18}$-alkyl, 3- to 8-membered cycloalkyl, 3- to 8-membered heterocyclyl, aryl or heteroaryl, where alkyl is unsubstituted or bears one or more R$^{2a}$ groups, where 3- to 8-membered cycloalkyl, 3- to 8-membered heterocyclyl, aryl and heteroaryl are unsubstituted or bear one or more R$^{2b}$ groups;

with the proviso that the compound of the formula II comprises at least one cyano group;

(ii) a cyanated perylene compound of the formula (III)

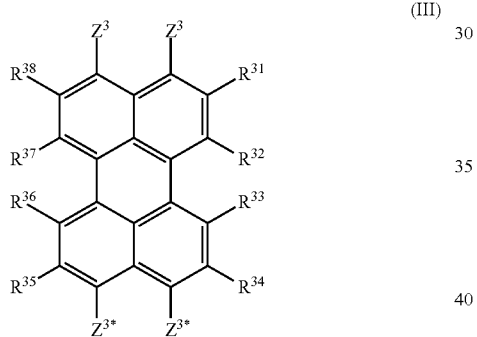

(III)

and mixtures thereof,
in which
one of the Z$^3$ substituents is cyano and the other Z$^3$ substituent is CO$_2$R$^{39}$, CONR$^{310}$R$^{311}$, C$_1$-C$_{18}$-alkyl, C$_2$-C$_{18}$-alkenyl, C$_2$-C$_{18}$-alkynyl, C$_3$-C$_{12}$-cycloalkyl or C$_6$-C$_{14}$-aryl, where
C$_1$-C$_{18}$-alkyl, C$_2$-C$_{18}$-alkenyl, C$_2$-C$_{18}$-alkynyl are unsubstituted or bear one or more identical or different Z$^{3a}$ substituents,
C$_3$-C$_{12}$-cycloalkyl is unsubstituted or bears one or more identical or different Z$^{3b}$ substituents, and
C$_6$-C$_{14}$-aryl is unsubstituted or bears one or more identical or different Z$^{3Ar}$ substituents;
one of the Z$^{3*}$ substituents is cyano and the other Z$^{3*}$ substituent is CO$_2$R$^{39}$, CONR$^{310}$R$^{311}$, C$_1$-C$_{18}$-alkyl, C$_2$-C$_{18}$-alkenyl, C$_2$-C$_{18}$-alkynyl, C$_3$-C$_{12}$-cycloalkyl or C$_6$-C$_{14}$-aryl, where
C$_1$-C$_{18}$-alkyl, C$_2$-C$_{18}$-alkenyl, C$_2$-C$_{18}$-alkynyl are unsubstituted or bear one or more identical or different Z$^{3a}$ substituents,
C$_3$-C$_{12}$-cycloalkyl is unsubstituted or bears one or more identical or different Z$^{3b}$ substituents, and
C$_6$-C$_{14}$-aryl is unsubstituted or bears one or more identical or different Z$^{3Ar}$ substituents;

R$^{31}$, R$^{32}$, R$^{33}$, R$^{34}$, R$^{35}$, R$^{36}$, R$^{37}$ and R$^{38}$ are each independently selected from hydrogen, cyano, bromine and chlorine,
with the proviso that 1, 2, 3, 4, 5, 6, 7 or 8 of the R$^{31}$, R$^{32}$, R$^{33}$, R$^{34}$, R$^{35}$, R$^{36}$, R$^{37}$ or R$^{38}$ substituents are cyano;
where
R$^{39}$ is hydrogen, C$_1$-C$_{10}$-alkyl, C$_2$-C$_{10}$-alkenyl, C$_2$-C$_{10}$-alkynyl, C$_3$-C$_{12}$-cycloalkyl or C$_6$-C$_{14}$-aryl, where
C$_1$-C$_{10}$-alkyl, C$_2$-C$_{10}$-alkenyl, C$_2$-C$_{10}$-alkynyl are unsubstituted or bear one or more identical or different R$^{3a}$ substituents,
C$_3$-C$_{12}$-cycloalkyl is unsubstituted or bears one or more identical or different R$^{3b}$ substituents and
C$_6$-C$_{14}$-aryl is unsubstituted or bears one or more identical or different R$^{3Ar}$ substituents;

R$^{310}$ and R$^{311}$ are each independently hydrogen, C$_1$-C$_{10}$-alkyl, C$_2$-C$_{10}$-alkenyl, C$_2$-C$_{10}$-alkynyl, C$_3$-C$_{12}$-cycloalkyl or C$_6$-C$_{14}$-aryl, where
C$_1$-C$_{10}$-alkyl, C$_2$-C$_{10}$-alkenyl, C$_2$-C$_{10}$-alkynyl are unsubstituted or bear one or more identical or different R$^{3a}$ substituents,
C$_3$-C$_{12}$-cycloalkyl is unsubstituted or bears one or more identical or different R$^{3b}$ substituents and
C$_6$-C$_{14}$-aryl is unsubstituted or bears one or more identical or different R$^{3Ar}$ substituents;

each Z$^{3a}$ is independently halogen, hydroxyl, NR$^{310a}$R$^{311a}$, C$_1$-C$_{10}$-alkoxy, C$_1$-C$_{10}$-haloalkoxy, C$_1$-C$_{10}$-alkylthio, C$_3$-C$_{12}$-cycloalkyl, C$_6$-C$_{14}$-aryl, C(=O)R$^{39a}$; C(=O)OR$^{39a}$ or C(O)NR$^{310a}$R$^{311a}$, where
C$_3$-C$_{12}$-cycloalkyl is unsubstituted or bears one or more identical or different R$^{3b}$ substituents and
C$_6$-C$_{14}$-aryl is unsubstituted or bears one or more identical or different R$^{3Ar}$ substituents;

each Z$^{3b}$ and each Z$^{3Ar}$ is independently halogen, hydroxyl, NR$^{310a}$R$^{311a}$, C$_1$-C$_{10}$-alkyl, C$_1$-C$_{10}$-alkoxy, C$_1$-C$_{10}$-haloalkoxy, C$_1$-C$_{10}$-alkylthio, C(=O)R$^{39a}$; C(=O)OR$^{39a}$ or C(O)NR$^{310a}$R$^{311a}$;

each R$^{3a}$ is independently halogen, hydroxyl, C$_1$-C$_{10}$-alkoxy, C$_3$-C$_{12}$-cycloalkyl or C$_6$-C$_{14}$-aryl;

each R$^{3b}$ is independently halogen, hydroxyl, C$_1$-C$_{10}$-alkyl, C$_1$-C$_{10}$-alkoxy, C$_1$-C$_{10}$-haloalkoxy, C$_1$-C$_{10}$-alkylthio, C$_2$-C$_{10}$-alkenyl, C$_2$-C$_{10}$-alkynyl, C$_3$-C$_{12}$-cycloalkyl or C$_6$-C$_{14}$-aryl;

each R$^{3Ar}$ is independently halogen, hydroxyl, C$_1$-C$_{10}$-alkyl, C$_1$-C$_{10}$-alkoxy, C$_1$-C$_{10}$-haloalkoxy, C$_1$-C$_{10}$-alkylthio, C$_2$-C$_{10}$-alkenyl, C$_2$-C$_{10}$-alkynyl, C$_3$-C$_{12}$-cycloalkyl or C$_6$-C$_{14}$-aryl;

R$^{39a}$ is hydrogen, C$_1$-C$_{10}$-alkyl, C$_2$-C$_{10}$-alkenyl, C$_2$-C$_{10}$-alkynyl, C$_3$-C$_{12}$-cycloalkyl or C$_6$-C$_{14}$-aryl; and R$^{310a}$, R$^{311a}$ are each independently hydrogen, C$_1$-C$_{10}$-alkyl, C$_2$-C$_{10}$-alkenyl, C$_2$-C$_{10}$-alkynyl, C$_3$-C$_{12}$-cycloalkyl or C$_6$-C$_{14}$-aryl;

(iii) a cyanated compound of the formula (IV)

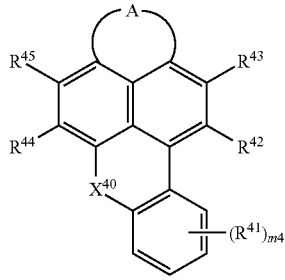

and mixtures thereof,
wherein
m4 is 0, 1, 2, 3 or 4;
each $R^{41}$ independently from each other is selected from bromine, chlorine, cyano, —$NR^{4a}R^{4b}$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, $C_6$-$C_{24}$-aryl-$C_1$-$C_{10}$-alkylene, where the rings of cycloalkyl, heterocycloalkyl, heteroaryl, aryl, aryloxy in the six last-mentioned radicals are unsubstituted or substituted with 1, 2, 3, 4 or 5 identical or different radicals $R^{41a}$ and where $C_1$-$C_{24}$-alkyl, $C_1$-$C_{24}$-haloalkyl, $C_1$-$C_{24}$-alkoxy, and the alkylene moiety of $C_6$-$C_{24}$-aryl-$C_1$-$C_{10}$-alkylene may be interrupted by one or more groups selected from O, S and $NR^{4c}$;
at least one of the radicals $R^{42}$, $R^{43}$, $R^{44}$ and $R^{45}$ is CN, and the remaining radicals, independently from each other, are selected from hydrogen, chlorine and bromine;
$X^{40}$ is O, S, SO or $SO_2$;
A is a diradical selected from diradicals of the general formulae (A.1), (A.2), (A.3), and (A.4)

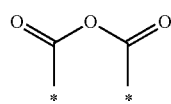

(A.1)

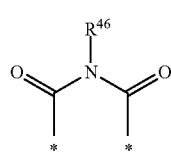

(A.2)

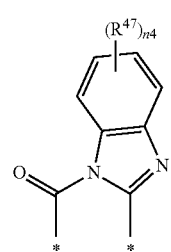

(A.3)

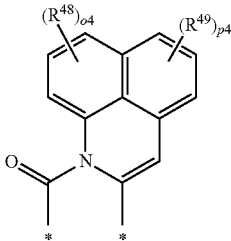

(A.4)

wherein
* in each case denotes the point of attachments to the remainder of the molecule;
n4 is 0, 1, 2, 3 or 4;
o4 is 0, 1, 2 or 3;
p4 is 0, 1, 2 or 3;
$R^{46}$ is hydrogen, $C_1$-$C_{24}$-alkyl, $C_1$-$C_{24}$-haloalkyl, $C_3$-$C_{24}$-cycloalkyl, $C_6$-$C_{24}$-aryl or $C_6$-$C_{24}$-aryl-$C_1$-$C_{10}$-alkylene, where the rings of cycloalkyl, aryl, and aryl-alkylene in the three last-mentioned radicals are unsubstituted or substituted with 1, 2, 3, 4 or 5 identical or different radicals $R^{46a}$, and where $C_1$-$C_{24}$-alkyl, $C_1$-$C_{24}$-haloalkyl and the alkylene moiety of $C_6$-$C_{24}$-aryl-$C_1$-$C_{10}$-alkylene may be interrupted by one or more heteroatoms or heteroatomic groups selected from O, S and $NR^{4c}$;
each $R^{47}$ independently from each other is selected from bromine, chlorine, cyano, —$NR^{4a}R^{4b}$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, $C_6$-$C_{24}$-aryl-$C_1$-$C_{10}$-alkylene, where the rings of cycloalkyl, heterocycloalkyl, heteroaryl, aryl and aryl-alkylene in the six last-mentioned radicals are unsubstituted or substituted with 1, 2, 3, 4 or 5 identical or different radicals $R^{47a}$ and where $C_1$-$C_{24}$-alkyl, $C_1$-$C_{24}$-haloalkyl, $C_1$-$C_{24}$-alkoxy, $C_1$-$C_{24}$-haloalkoxy, and the alkylene moiety of $C_6$-$C_{24}$-aryl-$C_1$-$C_{10}$-alkylene may be interrupted by one or more groups selected from O, S and $NR^{4c}$;
each $R^{48}$ independently from each other is selected from bromine, chlorine, cyano, $NR^{4a}R^{4b}$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, $C_6$-$C_{24}$-aryl-$C_1$-$C_{10}$-alkylene, where the rings of cycloalkyl, heterocycloalkyl, heteroaryl, aryl and aryl-alkylene in the six last-mentioned radicals are unsubstituted or substituted with 1, 2, 3, 4 or 5 identical or different radicals $R^{48a}$ and where $C_1$-$C_{24}$-alkyl, $C_1$-$C_{24}$-haloalkyl, $C_1$-$C_{24}$-alkoxy, $C_1$-$C_{24}$-haloalkoxy, and the alkylene moiety of $C_6$-$C_{24}$-aryl-$C_1$-$C_{10}$-alkylene may be interrupted by one or more groups selected from O, S and $NR^{4c}$;
each $R^{49}$ independently from each other is selected from bromine, chlorine, cyano, $NR^{4a}R^{4b}$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, $C_6$-$C_{24}$-aryl-$C_1$-$C_{10}$-alkylene, where the rings of cycloalkyl, heterocycloalkyl, heteroaryl, aryl and aryl-alkylene in the six last-mentioned radicals are unsubstituted or substituted with 1, 2, 3, 4 or 5 identical or different radicals $R^{49a}$ and where $C_1$-$C_{24}$-alkyl, $C_1$-$C_{24}$-haloalkyl, $C_1$-$C_{24}$-alkoxy, $C_1$-$C_{24}$-haloalkoxy, and the alkylene moiety of $C_6$-$C_{24}$-aryl-$C_1$-$C_{10}$-alkylene may be interrupted by one or more groups selected from O, S and $NR^{4c}$;

$R^{41a}$, $R^{46a}$, $R^{47a}$, $R^{48a}$, $R^{49a}$ are independently of one another selected from $C_1$-$C_{24}$-alkyl, $C_1$-$C_{24}$-fluoroalkyl, $C_1$-$C_{24}$-alkoxy, fluorine, chlorine and bromine;

$R^{4a}$, $R^{4b}$, $R^{4c}$ are independently of one another are selected from hydrogen, $C_1$-$C_{20}$-alkyl, $C_3$-$C_{24}$-cycloalkyl, heterocycloalkyl, heteroaryl and $C_6$-$C_{24}$-aryl;

(iv) a benzoxanthene compound of the formula (V)

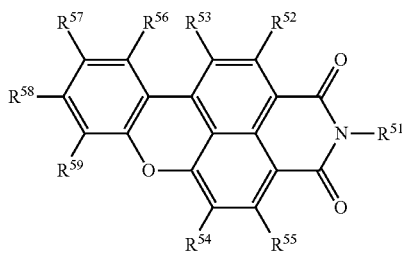

(V)

and mixtures thereof,
wherein
$R^{51}$ is phenyl which is unsubstituted or carries 1, 2, 3, 4, or 5 substituents selected from halogen, $R^{511}$, $OR^{552}$, $NHR^{552}$ and $NR^{552}R^{557}$;

$R^{52}$, $R^{53}$, $R^{54}$, $R^{55}$, $R^{56}$, $R^{57}$, $R^{58}$ and $R^{59}$ are independently of each other selected from hydrogen, halogen, $R^{553}$, $OR^{553}$, $NHR^{553}$ and $NR^{553}R^{554}$, wherein
$R^{511}$ is selected from $C_2$-$C_{18}$-alkyl, $C_6$-$C_{24}$-aryl and heteroaryl;

$R^{552}$ and $R^{557}$ are independently of each other selected from $C_1$-$C_{18}$-alkyl, $C_6$-$C_{24}$-aryl and heteroaryl; and $R^{553}$ and $R^{554}$ are independently of each other selected from $C_1$-$C_{18}$-alkyl, $C_6$-$C_{24}$-aryl and heteroaryl;

(v) a fluorescent compound comprising at least one structural unit of formula (VI)

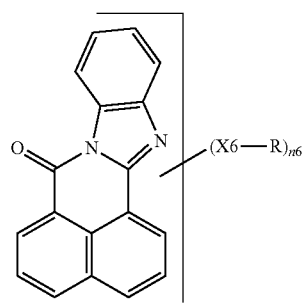

(VI)

where one or more CH groups of the six-membered ring of the benzimidazole structure shown may be replaced by nitrogen and where the symbols are each defined as follows:

n6 is a number from 0 to (10-p6) for each structural unit of the formula (VI); where p6 is the number of CH units which have been replaced by nitrogen in the six-membered ring of the benzimidazole structure shown X6 is a chemical bond, O, S, SO, $SO_2$, $NR^{61}$; and R is an aliphatic radical, cycloaliphatic radical, aryl, heteroaryl, each of which may bear substituents, an aromatic or heteroaromatic ring or ring system, each of which is fused to other aromatic rings of the structural unit of the formula (VI) is F, $C_1$, Br, CN, H when X6 is not a chemical bond;

where two R radicals may be joined to give one cyclic radical and where X6 and R, when n6>one, may be the same or different;

$R^{61}$ is each independently hydrogen, $C_1$-$C_{18}$-alkyl or cycloalkyl, the carbon chain of which may comprise one or more —O—, —S—, —CO—, —SO— and/or —$SO_2$— moieties and which may be mono- or polysubstituted;
aryl or heteroaryl which may be mono- or polysubstituted;

and mixtures thereof;

(vi) a perylene compound of the formulae (VII), (VIII), (IX) or (X)

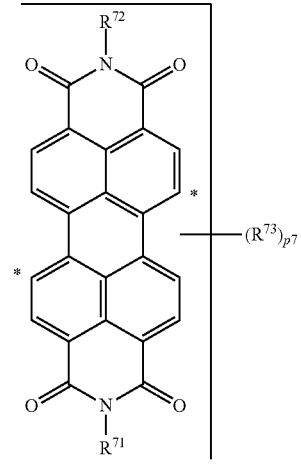

(VII)

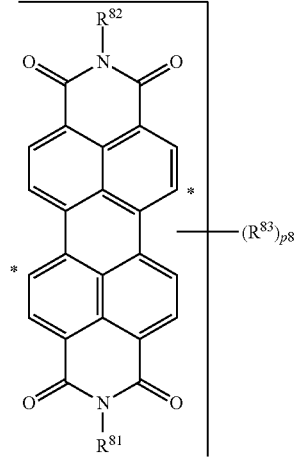

(VIII)

-continued (IX)

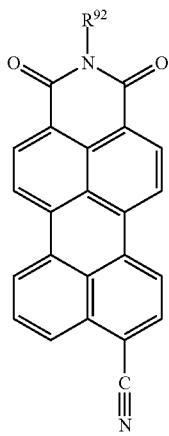

(X)

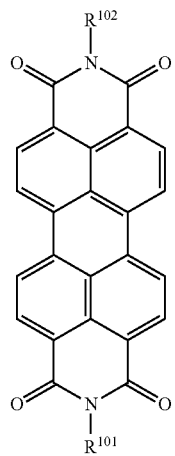

wherein
p7 is 2,
$R^{71}$, $R^{72}$ are each independently $C_1$-$C_{30}$-alkyl, $C_3$-$C_8$-cycloalkyl, aryl, heteroaryl, aryl-$C_1$-$C_{10}$-alkylene, where the aromatic ring in the three latter radicals is unsubstituted or mono- or polysubstituted by $C_1$-$C_{10}$-alkyl;
$R^{73}$ is aryloxy which is unsubstituted or mono- or polysubstituted by $C_1$-$C_{10}$-alkyl or $C_6$-$C_{10}$-aryl, where the $R^{73}$ radicals are at the positions indicated by *;
p8 is 2;
$R^{81}$, $R^{82}$ are each independently $C_1$-$C_{30}$-alkyl, $C_3$-$C_8$-cycloalkyl, aryl, heteroaryl, aryl-$C_1$-$C_{10}$-alkylene, where the aromatic ring in the three latter radicals is unsubstituted or mono- or polysubstituted by $C_1$-$C_{10}$-alkyl;
$R^{83}$ is aryloxy which is unsubstituted or mono- or polysubstituted by $C_1$-$C_{10}$-alkyl or $C_6$-$C_{10}$-aryl, where the $R^{83}$ radicals are at the positions indicated by *;
$R^{92}$ is $C_1$-$C_{30}$-alkyl, $C_3$-$C_8$-cycloalkyl, aryl, heteroaryl, aryl-$C_1$-$C_{10}$-alkylene, where the aromatic ring in the three latter radicals is unsubstituted or mono- or polysubstituted by $C_1$-$C_{10}$-alkyl;
$R^{101}$, $R^{102}$ are each independently $C_1$-$C_{30}$-alkyl, $C_3$-$C_8$-cycloalkyl, aryl, heteroaryl, aryl-$C_1$-$C_{10}$-alkylene, where the aromatic ring in the three latter radicals is unsubstituted or mono- or polysubstituted by $C_1$-$C_{10}$-alkyl;

(vii) a perylene bisimide compound of the formula (XI)

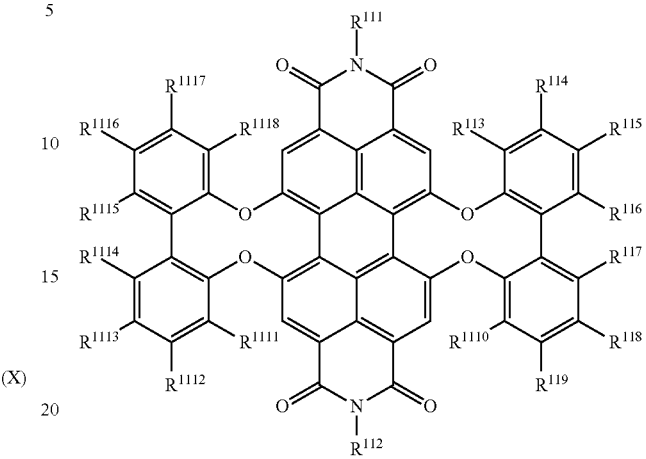

(XI)

and mixtures thereof,
wherein
$R^{111}$ and $R^{112}$, independently of each other, are selected from hydrogen, in each case unsubstituted or substituted $C_1$-$C_{30}$-alkyl, polyalkyleneoxy, $C_1$-$C_{30}$-alkoxy, $C_1$-$C_{30}$-alkylthio, $C_3$-$C_{20}$-cycloalkyl, $C_3$-$C_{20}$-cycloalkyloxy, $C_6$-$C_{24}$-aryl and $C_6$-$C_{24}$-aryloxy;
$R^{113}$, $R^{114}$, $R^{115}$, $R^{116}$, $R^{117}$, $R^{118}$, $R^{119}$, $R^{1110}$, $R^{1111}$, $R^{1112}$, $R^{1113}$, $R^{1114}$, $R^{1115}$, $R^{1116}$, $R^{1117}$ and $R^{1118}$ independently of each other, are selected from hydrogen, halogen, cyano, hydroxyl, mercapto, nitro, —$NE^{111}E^{112}$, —$NR^{Ar111}COR^{Ar112}$, —$CONR^{Ar111}R^{Ar112}$, —$SO_2NR^{Ar111}R^{Ar112}$, —$COOR^{Ar111}$, —$SO_3R^{Ar112}$,
in each case unsubstituted or substituted $C_1$-$C_{30}$-alkyl, polyalkyleneoxy, $C_1$-$C_{30}$-alkoxy, $C_1$-$C_{30}$-alkylthio, $C_3$-$C_{20}$-cycloalkyl, $C_3$-$C_{20}$-cycloalkoxy, $C_6$-$C_{24}$-aryl, $C_6$-$C_{24}$-aryloxy and $C_6$-$C_{24}$-arylthio,
where $R^{113}$ and $R^{114}$, $R^{114}$ and $R^{115}$, $R^{115}$ and $R^{116}$, $R^{116}$ and $R^{117}$, $R^{117}$ and $R^{118}$, $R^{118}$ and $R^{119}$, $R^{119}$ and $R^{1110}$, $R^{1111}$ and $R^{1112}$, $R^{1112}$ and $R^{1113}$, $R^{1113}$ and $R^{1114}$, $R^{1114}$ and $R^{1115}$, $R^{1115}$ and $R^{1116}$, $R^{1116}$ and $R^{1117}$ and/or $R^{1117}$ and $R^{1118}$ together with the carbon atoms of the biphenylyl moiety to which they are bonded, may also form a further fused aromatic or non-aromatic ring system wherein the fused ring system is unsubstituted or substituted;
where
$E^{111}$ and $E^{112}$, independently of each other, are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl;
$R^{Ar111}$ and $R^{Ar112}$, each independently of each, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl;
and mixtures thereof.
15. The color converter as defined in embodiment 14, wherein the at least one further organic fluorescent dye is selected from compounds of formula (II) and mixtures thereof,
compounds of formula (IV) and mixtures thereof,
compounds comprising at least one structural unit of formula (VI) and mixtures thereof,
compounds of formula (VII),
compounds of formula (VIII),
compounds of formula (XI) and mixtures thereof,
and mixtures thereof.

16. The color converter as defined in any of embodiments 14 or 15, wherein the compound comprising at least one structural unit of formula (VI) is selected from compounds of the formulae (VI-5), (VI-6), (VI-7), (VI-8),

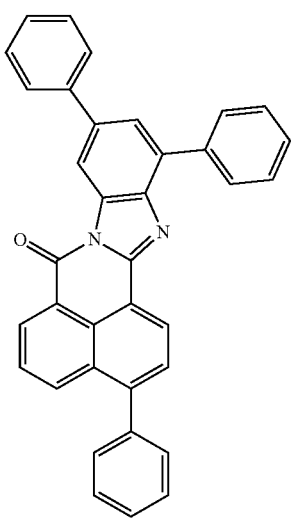

(VI-5)

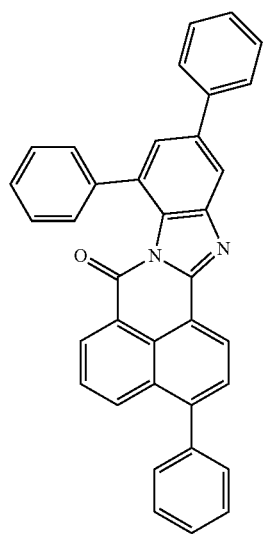

(VI-6)

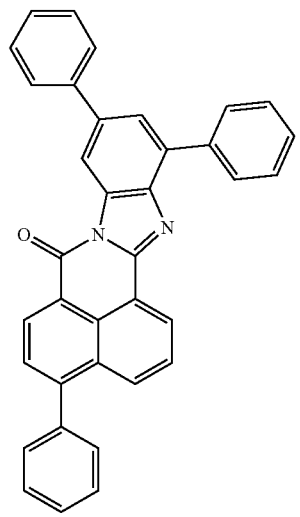

(VI-7)

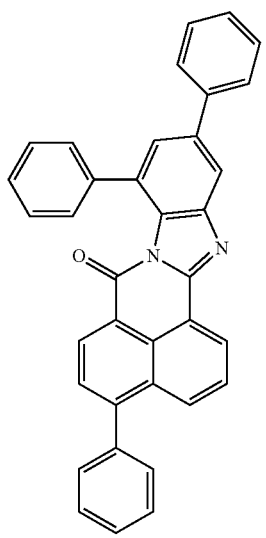

(VI-8)

and mixtures thereof.

17. The color converter as defined in any of embodiments 9 to 16, comprising as further fluorescent material at least one inorganic fluorescent material selected from garnets, silicates, sulfides, nitrides and oxynitrides.

18. The color converter as defined in any of embodiments 9 to 17, comprising at least one quantum dot from a crystalline semiconductor material.

19. The use of a color converter as defined in any of embodiments 9 to 18, for conversion of light generated by a blue LED with a center wavelength of emission between 420 nm and 480 nm to provide light of a second, longer wavelength.

20. The use of a color converter as defined in any of embodiments 9 to 18, for conversion of light generated by a cool white LED having a correlated color temperature between 6,000 K and 20,000 K, such as 20,000 K to 8,000 K or 15,000 K to 8,100 K to provide white light having a lower correlated color temperature.

21. A lighting device comprising at least one blue LED having a center wavelength of emission from 420 nm to 480 nm and at least one color converter as defined in any of embodiments 9 to 18, where LED and color converter are in a remote phosphor arrangement.

22. A lighting device comprising at least one a cool white LED having a correlated color temperature between 6,000 K and 20,000 K and at least one color converter as defined in any of embodiments 9 to 18, where LED and color converter are in a remote phosphor arrangement.

23. The use of a perylene bisimide compound of the formula I or a mixture thereof as defined in any of embodiments 1 to 8, in color converters for converting light emitted from a light source, in particular a light source selected from LEDs and OLEDs, into light of a second, longer wavelength, for coloring coatings, printing inks and plastics, producing aqueous polymer dispersions which absorb and/or emit electromagnetic radiation, for data storage, for optical labels, for security labels in documents and for brand protection or as a fluorescent label for biomolecules.

24. The use of a perylene bisimide compound of the formula I or a mixture thereof as defined in any of embodiments 1 to 8 in security inks for security printing.

25. A printing ink formulation for security printing, comprising at least one compound of the formula (I) or a mixture thereof as defined in any of embodiments 1 to 8.

26. A printing ink formulation as defined in embodiment 25, for security printing, comprising
   a) at least one compound of formula (I) or a mixture thereof as defined in any of embodiments 1 to 8;
   b) a polymeric binder;
   c) optionally an organic solvent;
   d) optionally at least one colorant; and
   e) optionally at least one further additive.

27. A printing ink formulation according to embodiments 25 or 26, comprising
   a) 0.0001 to 25% by weight of at least one compound of the formula (I) or a mixture thereof as defined in any of embodiments 1 to 8;
   b) 5 to 75% by weight of at least one polymeric binder,
   c) 0 to 94.9999% by weight of at least one solvent,
   d) 0 to 25% by weight of at least one colorant, and
   e) 0 to 25% by weight of at least one further additive, wherein the sum of components a) to e) adds up to 100%.

28. A process for the manufacture of a security document comprising the steps printing on a substrate a printing ink formulation according to any of embodiments 25 to 27.

29. A security document, comprising a substrate, a cured ink which ink comprises at least one compound of the formula (I) or a mixture thereof as defined in any of embodiments 1 to 8.

30. A security document according to embodiment 29 obtainable by a printing process wherein a printing ink formulation as defined in any of embodiments 25 to 27 is employed.

31. The security document according to embodiments 29 or 30 which is selected from a bank note, a passport, a check, a voucher, an ID- or transaction card, a stamp and a tax label.

32. The security document according to embodiment 30 or 31 which is part of a rigid or flexible packaging, of a carton board or of a brand or product label.

DETAILED DESCRIPTION OF THE INVENTION

The compounds of the formula (I) can be present in the form of an individual compound or in the form of mixtures comprising at least two different compounds of formula (I). The individual compounds of these mixtures can differ for example as regards the meanings of the substituents $R^1$-$R^{18}$ or the stereochemistry. As a rule, the individual compound of formula (I) as well as mixtures of compounds of the formula (I) are suitable for the uses according to the invention.

Thus, in the context of the present invention, the expression "at least one compound of the formula (I) or mixtures thereof", the expression "at least one compound of the formula (I) or a mixture thereof" and the expression "a compound of formula (I) or a mixture thereof" are understood to include an individual compound of the formula (I) or a mixture of at least two, e.g. two, three or more than three different compounds of formula (I).

In the context of the present invention, the term "phosphor" is also referred to as radiation conversion luminophore. These terms are used interchangeable to describe a material that converts light of a first wavelength into light of a second wavelength. The term "phosphor" encompasses inorganic phosphors and organic phosphors. Organic phosphors are also referred to as organic fluorescent dyes or colorants. The terms organic phosphors, organic fluorescent dye, organic fluorescent colorant and organic radiation conversion luminophore are used interchangeable in the context of the present invention.

In the context of the present invention, a yellow fluorescent dye is understood to mean an organic dye/colorant which emits light in the yellow, yellow-green range or green range of the electromagnetic spectrum. Accordingly, the term "yellow fluorescent dye", "yellow-green fluorescent dye", "green-yellow fluorescent dye" and "green fluorescent dye" are synonymously used.

In the context of the present invention, a red fluorescent dye is understood to mean an organic dye/colorant which emits light in the orange, orange-red or red range of the electromagnetic spectrum. Accordingly, the term "orange fluorescent dye", "orange-red fluorescent dye", "red-orange fluorescent dye" and "red fluorescent dye" are synonymously used.

In the context of the present invention, a "blue LED" is understood to mean an LED which emits light in the blue range of the electromagnetic spectrum with a center wavelength of 420 to 480 nm, preferably 440 to 470 nm, most preferably at 440 to 460 nm. Suitable semiconductor materials are silicon carbide, zinc selenide and nitrides such as aluminum nitride (AlN), gallium nitride (GaN), indium nitride (InN) and indium gallium nitride (InGaN). Standard InGaN-based blue LEDs are fabricated on a sapphire substrate and peak emission wavelength is usually centered at 445-455 nm.

In the context of the present invention, a "green LED" is understood to mean an LED which emits light in the green range of the electromgentic spectrum with a center wavelength wavelength of 501 to 560 nm, preferably 501 to 540 nm and especially 520 to 540 nm. Suitable semiconductor materials are for example based on GaInNAs.

In the context of the present invention, a "white LED" is understood to mean an LED which produces white light. The term "white LED" encompasses a phosphor-converted LED pumped by blue LED, a remote-phosphor LED pumped by blue LED and a hybrid LED pumped by blue LED. White light is generally described by its correlated color temperature CCT, see below.

A quantum dot is a nanocrystal made of semiconductor materials that is small enough to exhibit quantum mechanical properties. The quantum dot has a defined emission wavelength which is not subject to aging and is also photochemical stable. The color output of the dots can be tuned by controlling the size of the crystals. With a smaller size in quantum dots, the quantum dots emit light of a shorter wavelength.

In the context of the present invention, "color converter" is understood to mean all physical devices capable of absorbing light of particular wavelengths and converting it to light of a second wavelength. Color converters are, for example, part of lighting devices, especially those lighting devices which utilize LEDs or OLEDs as a light source, or of fluorescence conversion solar cells. Thus, the blue light may be (at least) partly converted into visible light of longer wavelengths than the excitation wavelengths.

The correlated color temperature (CCT) describes the color appearance of white light emitted from electric light sources and is measured in Kelvin. It is determined according to the CIE international standard. CCT from a white light source usually is in the range from 1,500 K and to 20 000 K, especially 2,000 K to 20 000 K. White light with higher CCT contains relatively higher intensity in the short wavelength region (blue) and relatively lower intensity in the longer wavelength region (red) compared to white light with lower CCT. Accordingly, higher CCTs generally indicate white light having a more significant blue component or a cool tone while lower CCTs generally indicate light having a more significant red tint or a warm tone. A white light having a CCT in the range from 4,500 K to 20 000 K is often referred to as cool white light, a white light having a CCT in the range from 2,700 K to 3,200 K is often referred to as warm-white light and a white light having a CCT in the range between 3,200 K to 4,500 K is often referred to as neutral white.

Color rendering (CRI) is a measure of how a light source makes the color of an object appear to the human eye and how well subtle variations in color shade are revealed. According to CIE 17.4, International Lighting Vocabulary, color rendering (CRI) is defined as "the effect of an illuminant on the color appearance of objects by conscious or unconscious comparison with the color appearance under a reference illuminant". A reference source, such as black body radiation, is defined as having a CRI index ($R_a$) of 100, i.e. a value of 100 indicates that the source renders colors in a manner identical to the reference. Negative values are also possible. The average or general color rendering index $R_a$ is calculated from the differences in the chromaticities of the eight pastel CIE standard (reference) color samples R1 to R8 (CIE 13.3-1995). For many general interior illumination applications, a CRI value ($R_a$) of greater than 80 is acceptable. For general lighting, the color rendering index should be above 85. In applications where accurate color rendering is required, a high CRI of at least 90 is usually highly desirable. For general lighting and various other applications, it is often desirable to provide a lighting source that generates white light having a high CRI (e.g. 90 or more), so that objects illuminated by the lighting source may appear to have more natural coloring to the human eye.

$R_a$ does not include coefficients corresponding to six highly saturated colors (R9-R14). Of these, R9 corresponds to a strong red color, which may affect a red-green contrast that may be beneficial in rendering colors. Often, the ability to reproduce red colors well is essential for accurately rendering colors, as the color red is often found mixed into processed colors. Thus, if a light source cannot render red correctly, things that are reddish will turn dull. Accordingly, light sources with high CRI and with positive R9 value tend to produce the most vivid colors.

According to the CIE 1931 standard colorimetric system, colors are perceived by human eye following specific color curves. The standard luminosity curve LV accounts for the wavelength dependence of the sensitivity of human eye. The luminosity curve has a maximum possible value of 683 lm/W, for the case of monochromatic light at a wavelength of 555 nm (green). Luminous flux is the measure of the perceived power of light.

The word "essentially" in the context of the present invention encompasses the words "completely", "wholly" and "all". The word encompasses a proportion of 90% or more, such as 95% or more, especially 99% or 100%.

The definitions of the variables specified in the above formulae use collective terms which are generally representative of the respective substituents. The definition $C_n$-$C_m$ gives the number of carbon atoms possible in each case in the respective substituent or substituent moiety.

The expression "halogen" denotes in each case fluorine, bromine, chlorine or iodine, particularly chlorine, bromide or iodine.

In the context of the invention, the expression "in each case unsubstituted or substituted alkyl, cycloalkyl and aryl" represents unsubstituted or substituted alkyl, unsubstituted or substituted cycloalkyl and unsubstituted or substituted aryl.

Likewise, in the context of the invention, the expression "in each case unsubstituted or substituted $C_1$-$C_{30}$-alkyl, polyalkyleneoxy, $C_1$-$C_{30}$-alkoxy, $C_1$-$C_{30}$-alkylthio, $C_3$-$C_{20}$-cycloalkyl, $C_3$-$C_{20}$-cycloalkyloxy, $C_6$-$C_{24}$-aryl and $C_6$-$C_{24}$-aryloxy" represents unsubstituted or substituted $C_1$-$C_{30}$-alkyl, unsubstituted or substituted polyalkyleneoxy, unsubstituted or substituted $C_1$-$C_{30}$-alkoxy, unsubstituted or substituted $C_1$-$C_{30}$-alkylthio, unsubstituted or substituted $C_3$-$C_{20}$-cycloalkyl, unsubstituted or substituted $C_3$-$C_{20}$-cycloalkyloxy, unsubstituted or substituted $C_6$-$C_{24}$-aryl and unsubstituted or substituted $C_6$-$C_{24}$-aryloxy.

The term "aliphatic radical" refers to an acyclic saturated or unsaturated, straight-chain or branched hydrocarbon radical. Usually the aliphatic radical has 1 to 100 carbon atoms. Examples for an aliphatic radical are alkyl, alkenyl and alkynyl.

The term "cycloaliphatic radical" refers to a cyclic, non-aromatic saturated or unsaturated hydrocarbon radical having usually 3 to 20 ring carbon atoms. Examples are cycloalkanes, cycloalkenes, and cycloalkynes. The cycloaliphatic radical may also comprise heteroatoms or heteroatom groups selected from N, O, S and $SO_2$.

The term "alkyl" as used herein and in the alkyl moieties of alkoxy, alkylthio, alkylsulfinyl, alkylsulfonyl, alkylamino, dialkylamino, alkylcarbonyl, alkoxycarbonyl and the like refers to saturated straight-chain or branched hydrocarbon radicals having usually 1 to 100 ("$C_1$-$C_{100}$-alkyl"), 1 to 30 ("$C_1$-$C_{30}$-alkyl"), 1 to 18 ("$C_1$-$C_{18}$-alkyl"), 1 to 12 ("$C_1$-$C_{12}$-alkyl"), 1 to 8 ("$C_1$-$C_8$-alkyl") or 1 to 6 ("$C_1$-$C_6$-alkyl") carbon atoms. Alkyl is preferably $C_1$-$C_{30}$-alkyl, more preferably $C_1$-$C_{20}$-alkyl. Examples of alkyl groups are especially methyl, ethyl, n-propyl, isopropyl, n-butyl, isobutyl, sec-butyl, tert-butyl, n-pentyl, 1-methylbutyl, 1-ethylpropyl, neo-pentyl, n-hexyl, 1-methylpentyl, 2-methylpentyl, 1-ethylbutyl, 2-ethylbutyl, n-heptyl, 1-methylhexyl, 2-methylhexyl, 1-ethylpentyl, 1-propylbutyl, 2-ethylpentyl, n-octyl, 1-methylheptyl, 2-methylheptyl, 1-ethylhexyl, 2-ethylhexyl, 1-propylpentyl, 2-propylpentyl, n-nonyl, 1-methyloctyl, 2-methyloctyl, 1-ethylheptyl, 2-ethylheptyl, 1-propylhexyl, 2-propylhexyl, 1-butylpentyl, n-decyl, 2-methyldecyl, 1-methylnonyl, 2-methylnonyl, 1-ethyloctyl, 2-ethyloctyl, 1-propylheptyl, 2-propylheptyl, 1-butylhexyl, 2-butylhexyl, n-undecyl, 2-ethylnonyl, 1-propyloctyl, 2-propyloctyl, 1-butylheptyl, 2-butylheptyl, 1-pentylhexyl, n-dodecyl, 2-ethyldecyl, 2-propylnonyl, 1-butyloctyl, 2-butyloctyl, 1-pentylheptyl, 2-pentylheptyl, 2-propyldecyl, n-tridecyl, 1-pentyloctyl, 2-pentyloctyl, 1-hexylheptyl, 2-butylnonyl, n-tetradecyl, 1-hexyloctyl, 2-hexyloctyl, 2-pentylnonyl, 2-hexylnonyl, 2-pentyldecyl, 2-butyldecyl, n-hexadecyl, 1-heptyloctyl, 2-heptylnonyl, 2-hexyldecyl, 2-heptyldecyl, n-octadecyl, 2-octyldecyl, n-eicosyl, 2-nonylundecyl, 2-octylundecyl, 2-heptylundecyl, 2-hexylundecyl, 2-pentylundecyl, 2-butylundecyl, 2-propylundecyl, 2-ethylundecyl, 2-methylundecyl, 2-decyldodecyl, 2-nonyldodecyl, 2-octyldodecyl, 2-heptyldodecyl, 2-hexyldodecyl, 2-pentyldodecyl, 2-butyldodecyl, 2-propyldodecyl, 2-ethyldodecyl, 2-methyldodecyl, 2-undecyltridecyl, 2-decyltridecyl, 2-nonyltridecyl, 2-octyltridecyl, 2-heptyltridecyl, 2-hexyltridecyl, 2-pentyltridecyl, 2-butyltridecyl, 2-propyltridecyl, 2-ethyltridecyl, 2-methyltridecyl, 2-undecyltetradecyl, 2-decyltetradecyl, 2-nonyltetradecyl, 2-octyltetradecyl, 2-hetyltetradecyl, 2-hexyltetradecyl, 2-pentyltetradecyl, 2-butyltetradecyl, 2-propyltetradecyl, 2-ethyltetradecyl, 2-methyltetradecyl, 2-tetradecylhexadecyl, 2-tridecylhexadecyl, 2-dodecylhexadecyl, 2-undecylhexadecyl, 2-decylhexadecyl, 2-nonylhexadecyl, 2-octylhexadecyl, 2-heptylhexadecyl, 2-hexylhexadecyl, 2-pentylhexadecyl, 2-butylhexadecyl, 2-propylhexadecyl, 2-ethylhexadecyl, 2-methylhexadecyl, 2-dodecyloctadecyl, 2-undecyloctadecyl, 2-decyloctadecyl, 2-nonyloctadecyl, 2-octyloctadecyl, 2-heptyloctadecyl, 2-hexyloctadecyl, 2-pentyloctadecyl, 2-butyloctadecyl, 2-propyloctadecyl, 2-ethyloctadecyl, 2-methyloctadecyl, 2-decyleicosanyl, 2-nonyleicosanyl, 2-octyleicosanyl, 2-heptyleicosanyl, 2-hexyleicosanyl, 2-pentyleicosanyl, 2-butyleicosanyl, 2-propyleicosanyl, 2-ethyleicosanyl, 2-methyleicosanyl, 2-octadecyldocosanyl, 2-heptadecyldocosanyl, 2-hexadecyldocosanyl, 2-pentadecyldocosanyl, 2-tetradecyldocosanyl, 2-tridecyldocosanyl, 2-undecyldocosanyl, 2-decyldocosanyl, 2-nonyldocosanyl, 2-octyldocosanyl, 2-heptyldocosanyl, 2-hexyldocosanyl, 2-pentyldocosanyl, 2-butyldocosanyl, 2-propyldocosanyl, 2-ethyldocosanyl, 2-methyldocosanyl, 2-docosanyltetracosanyl, 2-hexadecyltetracosanyl, 2-pentadecyltetracosanyl, 2-pentadecyltetracosanyl, 2-tetradecyltetracosanyl, 2-tridecyltetracosanyl, 2-dodecyltetracosanyl, 2-undecyltetracosanyl, 2-decyltetracosanyl, 2-nonyltetracosanyl, 2-octyltetracosanyl, 2-heptyltetracosanyl, 2-hexyltetracosanyl, 2-pentyltetracosanyl, 2-butyltetracosanyl, 2-propyltetracosanyl, 2-ethyltetracosanyl, 2-methyltetracosanyl, 2-dodecyloctacosanyl, 2-undecyloctacosanyl, 2-decyloctacosanyl, 2-nonyloctacosanyl, 2-octyloctacosanyl, 2-heptyloctacosanyl, 2-hexyloctacosanyl, 2-pentyloctacosanyl, 2-butyloctacosanyl, 2-propyloctacosanyl, 2-ethyloctacosanyl and 2-methyloctacosanyl.

Substituted alkyl groups, depending on the length of the alkyl chain, have one or more (e.g. 1, 2, 3, 4, 5 or more than 5) substituents. These are preferably each independently of each other selected from unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted hetaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cyclolalkyloxy, unsubstituted or substituted aryloxy, unsubstituted or substituted arylthio, cyano, nitro, unsubstituted or substituted alkylcarbonyloxy, formyl, acyl, COOH, carboxylate, —COOR$^{Ar1}$, NE$^1$E$^2$, —NR$^{Ar1}$COR$^{Ar2}$, —CONR$^{Ar1}$R$^{Ar2}$, —SO$_2$NR$^{Ar1}$R$^{Ar2}$ and —SO$_3$R$^{Ar2}$, where E$^1$ and E$^2$ are hydrogen, unsubstituted or substituted C$_1$-C$_{18}$-alkyl, unsubstituted or substituted C$_2$-C$_{18}$-alkenyl, unsubstituted or substituted C$_2$-C$_{18}$-alkynyl, unsubstituted or substituted C$_3$-C$_{20}$-cycloalkyl or unsubstituted or substituted C$_6$-C$_{10}$-aryl, and R$^{Ar1}$ and R$^{Ar2}$, independently of each other, are hydrogen, unsubstituted or substituted C$_1$-C$_{18}$-alkyl, unsubstituted or substituted C$_3$-C$_{20}$-cycloalkyl, unsubstituted or substituted heterocyclyl, unsubstituted or substituted C$_6$-C$_{20}$-aryl or unsubstituted or substituted heteroaryl. In particular, substituted alkyl groups have one or more, for example 1, 2 or 3 substituent(s) selected from unsubstituted or substituted cycloalkyl, unsubstituted or substituted aryl, fluorine, chlorine, bromine, hydroxyl, alkoxy, polyalkyleneoxy, mercapto, alkylthio, cyano, nitro, NE$^1$E$^2$, —NR$^{Ar1}$COR$^{Ar2}$, —CONR$^{Ar1}$R$^{Ar2}$, —SO$_2$NR$^{Ar1}$R$^{Ar2}$, and —SO$_3$R$^{Ar2}$, where E$^1$, E$^2$, independently of each other, are hydrogen, unsubstituted or substituted C$_1$-C$_{18}$-alkyl, unsubstituted or substituted C$_2$-C$_{18}$-alkenyl, unsubstituted or substituted C$_2$-C$_{18}$-alkynyl, unsubstituted or substituted C$_3$-C$_{20}$-cycloalkyl or unsubstituted or substituted C$_6$-C$_{10}$-aryl, and R$^{Ar1}$ and R$^{Ar2}$, each independently of each, are hydrogen, unsubstituted or substituted C$_1$-C$_{18}$-alkyl, unsubstituted or substituted C$_3$-C$_{20}$-cycloalkyl, unsubstituted or substituted heterocyclyl, unsubstituted or substituted C$_6$-C$_{20}$-aryl or unsubstituted or substituted heteroaryl.

Special embodiments of substituted alkyl groups are alkyl groups, wherein one hydrogen atom has been replaced by an aryl radical ("aralkyl", also referred to hereinafter as arylalkyl or arylalkylene), in particular a phenyl radical. The aryl radical in turn may be unsubstituted or substituted, suitable substituents are the substituents mentioned below for aryl. Particular examples of aryl-C$_1$-C$_4$-alkyl include benzyl, 1-phenethyl, 2-phenetyl, 1-phenylpropyl, 2-phenylpropyl, 3-phenyl-1-propyl, 2-phenyl-2-propyl, naphthylmethyl, naphthylethyl etc.

Further special embodiments of substituted alkyl groups are alkyl groups where some or all of the hydrogen atoms in these groups may be replaced by halogen atoms as mentioned above, for example C$_1$-C$_4$-haloalkyl.

The term "alkenyl" as used herein refers to straight-chain or branched hydrocarbon groups having usually 2 to 100 ("C$_2$-C$_{100}$-alkenyl"), 2 to 18 ("C$_2$-C$_{18}$-alkenyl"), 2 to 10 ("C$_2$-C$_{10}$-alkenyl"), 2 to 8 ("C$_2$-C$_8$-alkenyl"), or 2 to 6 ("C$_2$-C$_6$-alkenyl") carbon atoms and one or more, e.g. 2 or 3, double bonds in any position. Substituted alkenyl groups, depending on the length of the alkenyl chain, have one or more (e.g. 1, 2, 3, 4, 5 or more than 5) substituents. These are preferably each independently of each other selected from unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted hetaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cyclolalkyloxy, unsubstituted or substituted aryloxy, unsubstituted or substituted arylthio, cyano, nitro, unsubstituted or substituted alkylcarbonyloxy, formyl, acyl, COOH, carboxylate, —COOR$^{Ar1}$, NE$^1$E$^2$, —NR$^{Ar1}$COR$^{Ar2}$, —CONR$^{Ar1}$R$^{Ar2}$, —SO$_2$NR$^{Ar2}$ and —SO$_3$R$^{Ar2}$, where E$^1$ and E$^2$ are hydrogen, unsubstituted or substituted C$_1$-C$_{18}$-alkyl, unsubstituted or substituted C$_2$-C$_{18}$-alkenyl, unsubstituted or substituted C$_2$-C$_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, independently of each other, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl. In particular, substituted alkenyl groups have one or more, for example 1, 2 or 3 substituent(s) selected from unsubstituted or substituted cycloalkyl, unsubstituted or substituted aryl, fluorine, chlorine, bromine, hydroxyl, alkoxy, polyalkyleneoxy, mercapto, alkylthio, cyano, nitro, $NE^1E^2$, —$NR^{Ar1}COR^{Ar2}$, —$CONR^{Ar1}R^{Ar2}$, —$SO_2NR^{Ar1}R^{Ar2}$, and —$SO_3R^{Ar2}$, where $E^1$, $E^2$, independently of each other, are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, each independently of each, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl.

The term "alkynyl" as used herein (also referred to as alkyl whose carbon chain may comprise one or more triple bonds) refers to straight-chain or branched hydrocarbon groups having usually 2 to 100 ("$C_2$-$C_{100}$-alkynyl"), 2 to 18 ("$C_2$-$C_{18}$-alknyl"), 2 to 10 ("$C_2$-$C_{10}$-alkynyl"), 2 to 8 ("$C_2$-$C_8$-alkynyl"), or 2 to 6 ("$C_2$-$C_6$-alkynyl") carbon atoms and one or more, e.g. 2 or 3, triple bonds in any position. Substituted alkynyl groups, depending on the length of the alkynyl chain, have one or more (e.g. 1, 2, 3, 4, 5 or more than 5) substituents. These are preferably each independently of each other selected from unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted hetaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cyclolalkyloxy, unsubstituted or substituted aryloxy, unsubstituted or substituted arylthio, cyano, nitro, alkylcarbonyloxy, formyl, acyl, COOH, carboxylate, —$COOR^{Ar1}$, $NE^1E^2$, —$NR^{Ar1}COR^{Ar2}$, —$CONR^{Ar1}R^{Ar2}$, —$SO_2NR^{Ar1}R^{Ar2}$ and —$SO_3R^{Ar2}$, where $E^1$ and $E^2$ are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, independently of each other, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl. In particular, substituted alkynyl groups have one or more, for example 1, 2 or 3 substituent(s) selected from unsubstituted or substituted cycloalkyl, unsubstituted or substituted aryl, fluorine, chlorine, bromine, hydroxyl, alkoxy, polyalkyleneoxy, mercapto, alkylthio, cyano, nitro, $NE^1E^2$, —$NR^{Ar1}COR^{Ar2}$, —$CONR^{Ar1}R^{Ar2}$, —$SO_2NR^{Ar1}R^{Ar2}$, and —$SO_3R^{Ar2}$, where $E^1$, $E^2$, independently of each other, are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, each independently of each, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl.

The term "alkoxy" as used herein refers to an alkyl group bound through an oxygen atom, that is, an "alkoxy" group may be represented as —O-alkyl where alkyl is as defined above. $C_1$-$C_2$-Alkoxy is methoxy or ethoxy. $C_1$-$C_4$-Alkoxy is, for example, methoxy, ethoxy, n-propoxy, 1-methylethoxy (isopropoxy), butoxy, 1-methylpropoxy (sec-butoxy), 2-methylpropoxy (isobutoxy) or 1,1-dimethylethoxy (tert-butoxy).

Accordingly, the term "unsubstituted or substituted alkoxy" as used herein refers to —O-alkyl where alkyl is unsubstituted or substituted as defined above.

The term "polyoxyalkylene" as used herein refers to an alkyl group bound through an oxygen atom to the remainder of the molecule, where alkyl is interrupted by one or more non-adjacent oxygen atoms and alkyl is as defined above.

Accordingly, the term "unsubstituted or substituted polyalkyleneoxy" as used herein refers to —O-alkyl where alkyl is interrupted by one or more non-adjacent oxygen atoms and alkyl is unsubstituted or substituted as defined above.

The term "alkylthio" as used herein refers to an alkyl group bound through a sulfur atom, that is, an "alkylthio" group may be represented as —S-alkyl where alkyl is as defined above. $C_1$-$C_2$-Alkylthio is methylthio or ethylthio. $C_1$-$C_4$-Alkylthio is, for example, methylthio, ethylthio, n-propylthio, 1-methylethylthio (isopropylthio), butylthio, 1-methylpropylthio (sec-butylthio), 2-methylpropylthio (isobutylthio) or 1,1-dimethylethylthio (tert-butylthio).

Accordingly, the term "unsubstituted or substituted alkylthio" as used herein refers to —S-alkyl where alkyl is unsubstituted or substituted as defined above.

The term "cycloalkyl" as used herein refers to mono- or bi- or polycyclic saturated hydrocarbon radicals having usually 3 to 24 ($C_3$-$C_{24}$-cycloalkyl), 3 to 20 ("$C_3$-$C_{20}$-cycloalkyl") atoms, preferably 3 to 8 ("$C_3$-$C_8$-cycloalkyl") or 3 to 6 carbon atoms ("$C_3$-$C_6$-cycloalkyl"). Examples of monocyclic radicals having 3 to 6 carbon atoms comprise cyclopropyl, cyclobutyl, cyclopentyl and cyclohexyl. Examples of monocyclic radicals having 3 to 8 carbon atoms comprise cyclopropyl, cyclobutyl, cyclopentyl, cyclohexyl, cycloheptyl and cyclooctyl. Examples of bicyclic radicals having 7 to 12 carbon atoms comprise bicyclo[2.2.1]heptyl, bicyclo[3.1.1]heptyl, bicyclo[2.2.2]octyl, bicyclo[3.3.0]octyl, bicyclo[3.2.1]octyl, bicyclo[3.3.1]nonyl, bicyclo[4.2.1]nonyl, bicyclo[4.3.1]decyl, bicyclo[3.3.2]decyl, bicyclo[4.4.0]decyl, bicyclo[4.2.2]decyl, bicyclo[4.3.2] undecyl, bicyclo[3.3.3]undecyl, bicyclo[4.3.3]dodecyl, and perhydronaphthyl. Examples of polycyclic rings are perhydroanthracyl, perhydrofluorenyl, perhydrochrysenyl, perhydropicenyl, and adamantyl.

Substituted cycloalkyl groups may, depending on the ring size, have one or more (e.g. 1, 2, 3, 4, 5 or more than 5) substituents. These are preferably each independently of each other selected from unsubstituted or substituted alkyl, unsubstituted or substituted alkenyl, unsubstituted or substituted alkynyl, unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted hetaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cyclolalkyloxy, unsubstituted or substituted aryloxy, unsubstituted or substituted arylthio, cyano, nitro, unsubstituted or substituted alkylcarbonyloxy, formyl, acyl, COOH, carboxylate, —COOR$^{Ar1}$, —NE$^1$E$^2$, —NR$^{Ar1}$COR$^{Ar2}$, —CONR$^{Ar1}$R$^{Ar2}$, —SO$_2$NR$^{Ar1}$R$^{Ar2}$ and —SO$_3$R$^{Ar2}$, where E$^1$ and E$^2$ are hydrogen, unsubstituted or substituted C$_1$-C$_{18}$-alkyl, unsubstituted or substituted C$_2$-C$_{18}$-alkenyl, unsubstituted or substituted C$_2$-C$_{18}$-alkynyl, unsubstituted or substituted C$_3$-C$_{20}$-cycloalkyl or unsubstituted or substituted C$_6$-C$_{10}$-aryl, and R$^{Ar1}$ and R$^{Ar2}$, independently of each other, are hydrogen, unsubstituted or substituted C$_1$-C$_{18}$-alkyl, unsubstituted or substituted C$_3$-C$_{20}$-cycloalkyl, unsubstituted or substituted heterocyclyl, unsubstituted or substituted C$_6$-C$_{20}$-aryl or unsubstituted or substituted heteroaryl. In particular, substituted cycloalkyl groups have one or more, for example 1, 2 or 3 substituent(s) selected from unsubstituted or substituted alkyl, unsubstituted or substituted cycloalkyl, unsubstituted or substituted aryl, fluorine, chlorine, bromine, hydroxyl, alkoxy, polyalkyleneoxy, mercapto, alkylthio, cyano, nitro, NE$^1$E$^2$, —NR$^{Ar1}$COR$^{Ar2}$, —CONR$^{Ar1}$R$^{Ar2}$, —SO$_2$NR$^{Ar1}$R$^{Ar2}$, and —SO$_3$R$^{Ar2}$, where E$^1$, E$^2$, independently of each other, are hydrogen, unsubstituted or substituted C$_1$-C$_{18}$-alkyl, unsubstituted or substituted C$_2$-C$_{18}$-alkenyl, unsubstituted or substituted C$_2$-C$_{18}$-alkynyl, unsubstituted or substituted C$_3$-C$_{20}$-cycloalkyl or unsubstituted or substituted C$_6$-C$_{10}$-aryl, and R$^{Ar1}$ and R$^{Ar2}$, each independently of each, are hydrogen, unsubstituted or substituted C$_1$-C$_{18}$-alkyl, unsubstituted or substituted C$_3$-C$_{20}$-cycloalkyl, unsubstituted or substituted heterocyclyl, unsubstituted or substituted C$_6$-C$_{20}$-aryl or unsubstituted or substituted heteroaryl.

The term "cycloalkyloxy" as used herein refers to a cycloalkyl group bound through an oxygen atom, that is, a "cycloalkyloxy" group may be represented as —O-cycloalkyl where cycloalkyl is as defined above.

Accordingly, the term "unsubstituted or substituted cycloalkyloxy" as used herein refers to —O-cycloalkyl where cycloalkyl is unsubstituted or substituted as defined above.

The term "cycloalkylthio" as used herein refers to a cycloalkyl group bound through a sulfur atom, that is, a "cycloalkylthio" group may be represented as —S-cycloalkyl where cycloalkyl is as defined above.

Accordingly, the term "unsubstituted or substituted cycloalkylthio" as used herein refers to —S-cycloalkyl where cycloalkyl is unsubstituted or substituted as defined above.

The term heterocycloalkyl refers to nonaromatic, partially unsaturated or fully saturated, heterocyclic rings having generally 5 to 8 ring members, preferably 5 or 6 ring members, comprising besides carbon atoms as ring members, one, two, three or four heteroatoms or heteroatom-containing groups selected from O, N, NR$^{cc}$, S, SO and S(O)$_2$ as ring members, wherein R$^{cc}$ is hydrogen, C$_1$-C$_{20}$-alkyl, C$_3$-C$_{24}$-cycloalkyl, heterocycloalkyl, C$_6$-C$_{24}$-aryl or heteroaryl. Examples of heterocycloalkyl groups are especially pyrrolidinyl, piperidinyl, imidazolidinyl, pyrazolidinyl, oxazolidinyl, morpholinyl, thiazolidinyl, isothiazolidinyl, isoxazolidinyl, piperazinyl, tetrahydrothiophenyl, dihydrothien-2-yl, tetrahydrofuranyl, dihydrofuran-2-yl, tetrahydropyranyl, 2-oxazolinyl, 3-oxazolinyl, 4-oxazolinyl and dioxanyl. Substituted heterocycloalkyl groups may, depending on the ring size, have one or more (e.g. 1, 2, 3, 4, 5 or more than 5) substituents. These are preferably each independently of each other selected from unsubstituted or substituted alkyl, unsubstituted or substituted alkenyl, unsubstituted or substituted alkynyl, unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted hetaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cyclolalkyloxy, unsubstituted or substituted aryloxy, unsubstituted or substituted arylthio, cyano, nitro, unsubstituted or substituted alkylcarbonyloxy, formyl, acyl, COOH, carboxylate, —COOR$^{Ar1}$, —NE$^1$E$^2$, —NR$^{Ar1}$COR$^{Ar2}$, —CONR$^{Ar1}$R$^{Ar2}$, —SO$_2$NR$^{Ar1}$R$^{Ar2}$ and —SO$_3$R$^{Ar2}$, where E$^1$ and E$^2$ are hydrogen, unsubstituted or substituted C$_1$-C$_{18}$-alkyl, unsubstituted or substituted C$_2$-C$_{18}$-alkenyl, unsubstituted or substituted C$_2$-C$_{18}$-alkynyl, unsubstituted or substituted C$_3$-C$_{20}$-cycloalkyl or unsubstituted or substituted C$_6$-C$_{10}$-aryl, and R$^{Ar1}$ and R$^{Ar2}$, independently of each other, are hydrogen, unsubstituted or substituted C$_1$-C$_{18}$-alkyl, unsubstituted or substituted C$_3$-C$_{20}$-cycloalkyl, unsubstituted or substituted heterocyclyl, unsubstituted or substituted C$_6$-C$_{20}$-aryl or unsubstituted or substituted heteroaryl. In particular, substituted heterocycloalkyl groups have one or more, for example 1, 2 or 3 substituent(s) selected from unsubstituted or substituted alkyl, unsubstituted or substituted cycloalkyl, unsubstituted or substituted aryl, fluorine, chlorine, bromine, hydroxyl, alkoxy, polyalkyleneoxy, mercapto, alkylthio, cyano, nitro, NE$^1$E$^2$, —NR$^{Ar1}$COR$^{Ar2}$, —CONR$^{Ar1}$R$^{Ar2}$, —SO$_2$NR$^{Ar1}$R$^{Ar2}$, and —SO$_3$R$^{Ar2}$, where E$^1$, E$^2$, independently of each other, are hydrogen, unsubstituted or substituted C$_1$-C$_{18}$-alkyl, unsubstituted or substituted C$_2$-C$_{18}$-alkenyl, unsubstituted or substituted C$_2$-C$_{18}$-alkynyl, unsubstituted or substituted C$_3$-C$_{20}$-cycloalkyl or unsubstituted or substituted C$_6$-C$_{10}$-aryl, and R$^{Ar1}$ and R$^{Ar2}$, each independently of each, are hydrogen, unsubstituted or substituted C$_1$-C$_{18}$-alkyl, unsubstituted or substituted C$_3$-C$_{20}$-cycloalkyl, unsubstituted or substituted heterocyclyl, unsubstituted or substituted C$_6$-C$_{20}$-aryl or unsubstituted or substituted heteroaryl.

In the context of the present invention, the term "aryl" refers to phenyl or fused bi-, tri- or polycyclic aromatic radicals having at least one fused phenyl ring and ordinarily a total number of ring members of 9 to 24 carbon atoms. If it is not phenyl, the term includes for the fused ring(s) the saturated form (perhydro form), the partly unsaturated form (for example the dihydro form or tetrahydro form) or the aromatic form. The term "aryl" includes, for example bicyclic aromatic radicals in which both rings are aromatic and bicyclic aromatic radicals in which only one ring is aromatic. Examples of bi- or tricyclic aromatic carbocycles include naphthyl, 1,2-dihydronaphthyl, 1,4-dihydronaphthyl, 1,2,3,4-tetrahydronaphthyl, indanyl, indenyl, anthracenyl, fluorenyl etc. Preferably, the term "aryl" denotes phenyl and naphthyl.

Substituted aryls may, depending on the number and size of their ring systems, have one or more (e.g. 1, 2, 3, 4, 5 or more than 5) substituents. These are preferably each independently of each other selected from unsubstituted or substituted alkyl, unsubstituted or substituted alkenyl, unsubstituted or substituted alkynyl, unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted hetaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cyclolalkyloxy, unsubstituted or substituted aryloxy, unsubstituted or substituted arylthio, cyano, nitro, unsubstituted or substituted alkylcarbonyloxy, formyl, acyl, COOH, carboxylate, —CO$OR^{Ar1}$, —$NE^1E^2$, —$NR^{Ar1}COR^{Ar2}$, —$CONR^{Ar1}R^{Ar2}$, —$SO_2NR^{Ar1}R^{Ar2}$ and —$SO_3R^{Ar2}$, where $E^1$ and $E^2$ are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, independently of each other, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl. In particular, substituted aryl groups have one or more, for example 1, 2 or 3 substituent(s) selected from unsubstituted or substituted alkyl, unsubstituted or substituted cycloalkyl, unsubstituted or substituted aryl, fluorine, chlorine, bromine, hydroxyl, alkoxy, polyalkyleneoxy, mercapto, alkylthio, cyano, nitro, $NE^1E^2$, —$NR^{Ar1}COR^{Ar2}$, —$CONR^{Ar1}R^{Ar2}$, —$SO_2NR^{Ar1}R^{Ar2}$, and —$SO_3R^{Ar2}$, where $E^1$, $E^2$, independently of each other, are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl, and $R^{Ar1}$ and $R^{Ar2}$, each independently of each, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl.

Substituted aryl is preferably aryl substituted by at least one alkyl group ("alkaryl", also referred to hereinafter as alkylaryl). Alkaryl groups may, depending on the size of the aromatic ring system, have one or more (e.g. 1, 2, 3, 4, 5, 6, 7, 8, 9 or more than 9) alkyl substituents. The alkyl substituents may be unsubstituted or substituted. In this regard, reference is made to the above statements regarding unsubstituted and substituted alkyl. A special embodiment relates to alkaryl groups, wherein alkyl is unsubstituted. Alkaryl is preferably phenyl which bears 1, 2, 3, 4 or 5, preferably 1, 2 or 3, more preferably 1 or 2 alkyl substituents. Aryl which bears one or more alkyl radicals, is, for example, 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-n-propylphenyl, 2-, 3- and 4-iso-propylphenyl, 2,4-, 2,5-, 3,5- and 2,6-di-n-propylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl and 2,4,6-tri-tert-butylphenyl.

$C_6$-$C_{24}$-aryloxy: $C_6$-$C_{24}$-aryl as defined above, which is bonded to the skeleton via an oxygen atom (—O—). Preference is given to phenoxy and naphthyloxy.

Accordingly, the term "unsubstituted or substituted aryloxy" as used herein refers to —O-aryl where aryl is unsubstituted or substituted as defined above.

$C_6$-$C_{24}$-arylthio: $C_6$-$C_{24}$-aryl as defined above, which is bonded to the skeleton via a sulfur atom (—S—). Preference is given to phenylthio and naphthylthio.

Accordingly, the term "unsubstituted or substituted arylthio" as used herein refers to —S-aryl where aryl is unsubstituted or substituted as defined above.

In the context of the present invention, the expression "hetaryl" (also referred to as heteroaryl) comprises heteroaromatic, mono- or polycyclic groups. In addition to the ring carbon atoms, these have 1, 2, 3, 4 or more than 4 heteroatoms as ring members. The heteroatoms are preferably selected from oxygen, nitrogen, selenium and sulfur. The hetaryl groups have preferably 5 to 18, e.g. 5, 6, 8, 9, 10, 11, 12, 13 or 14, ring atoms.

Monocyclic hetaryl groups are preferably 5- or 6-membered hetaryl groups, such as 2-furyl (furan-2-yl), 3-furyl (furan-3-yl), 2-thienyl (thiophen-2-yl), 3-thienyl (thiophen-3-yl), selenophen-2-yl, selenophen-3-yl, 1H-pyrrol-2-yl, 1H-pyrrol-3-yl, pyrrol-1-yl, imidazol-2-yl, imidazol-1-yl, imidazol-4-yl, pyrazol-1-yl, pyrazol-3-yl, pyrazol-4-yl, pyrazol-5-yl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 4H-[1,2,4]-triazol-3-yl, 1,3,4-triazol-2-yl, 1,2,3-triazol-1-yl, 1,2,4-triazol-1-yl, pyridin-2-yl, pyridin-3-yl, pyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Polycyclic hetaryl groups have 2, 3, 4 or more than 4 fused rings. The fused-on rings may be aromatic, saturated or partly unsaturated. Examples of polycyclic hetaryl groups are quinolinyl, isoquinolinyl, indolyl, isoindolyl, indolizinyl, benzofuranyl, isobenzofuranyl, benzothiophenyl, benzoxazolyl, benzisoxazolyl, benzthiazolyl, benzoxadiazolyl, benzothiadiazolyl, benzoxazinyl, benzopyrazolyl, benzimidazolyl, benzotriazolyl, benzotriazinyl, benzoselenophenyl, thienothiophenyl, thienopyrimidyl, thiazolothiazolyl, dibenzopyrrolyl (carbazolyl), dibenzofuranyl, dibenzothiophenyl, naphtho[2,3-b]thiophenyl, naphtha[2,3-b]furyl, dihydroindolyl, dihydroindolizinyl, dihydroisoindolyl, dihydroquinolinyl and dihydroisoquinolinyl.

Substituted hetaryl groups may, depending on the number and size of their ring systems, have one or more (e.g. 1, 2, 3, 4, 5 or more than 5) substituents. These are preferably each independently of each other selected from unsubstituted or substituted alkyl, unsubstituted or substituted alkenyl, unsubstituted or substituted alkynyl, unsubstituted or substituted cycloalkyl, unsubstituted or substituted cycloalkyloxy, unsubstituted or substituted cycloalkylthio, unsubstituted or substituted heterocycloalkyl, unsubstituted or substituted aryl, unsubstituted or substituted aryloxy, unsubstituted or substituted arylthio, unsubstituted or substituted hetaryl, fluorine, chlorine, bromine, iodine, hydroxyl, mercapto, unsubstituted or substituted alkoxy, unsubstituted or substituted polyalkyleneoxy, unsubstituted or substituted alkylthio, unsubstituted or substituted cyclolalkyloxy, unsubstituted or substituted aryloxy, unsubstituted or substituted arylthio, cyano, nitro, unsubstituted or substituted alkylcarbonyloxy, formyl, acyl, COOH, carboxylate, —CO$OR^{Ar1}$, —$NE^1E^2$, —$NR^{Ar11}COR^{Ar2}$, —$CONR^{Ar1}R^{Ar2}$, —$SO_2NR^{Ar1}R^{Ar2}$ and —$SO_3R^{Ar2}$, where $E^1$ and $E^2$ are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$- aryl, and $R^{Ar1}$ and $R^{Ar2}$, independently of each other, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl. In particular, substituted hetaryl groups have one or more, for example 1, 2 or 3 substituent(s) selected from unsubstituted or substituted alkyl, unsubstituted or substituted cycloalkyl, unsubstituted or substituted aryl, fluorine, chlorine, bromine, hydroxyl, alkoxy, polyalkyleneoxy, mercapto, alkylthio, cyano, nitro, $NE^1E^2$, —$NR^{Ar1}COR^{Ar2}$, —$CONR^{Ar1}R^{Ar2}$, —$SO_2NR^{Ar1}R^{Ar2}$, and —$SO_3R^{Ar2}$, where $E^1$, $E^2$, $R^{Ar1}$ and $R^{Ar2}$ are as defined above.

Fused ring systems can comprise alicyclic, aliphatic heterocyclic, aromatic and heteroaromatic rings and combinations thereof, hydroaromatic joined by fusion. Fused ring systems comprise two, three or more (e.g. 4, 5, 6, 7 or 8) rings. Depending on the way in which the rings in fused ring systems are joined, a distinction is made between ortho-fusion, i.e. each ring shares at least one edge or two atoms with each adjacent ring, and peri-fusion in which a carbon atom belongs to more than two rings. Preferred fused ring systems are ortho-fused ring systems.

When # or * appear in a formula showing a substructure of a compound of the present invention, it denotes the attachment bond in the remainder molecule.

With a view to the use of the compound of the formula (I) according to the invention, the remarks made below concerning the variables $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R^{18}$, are valid both on their own and, in particular, in every possible combination with each other.

In the compounds of the formula (I), $R^1$ and $R^2$ may have the same or different meaning.

Preferably, $R^1$ and $R^2$, independently of each other are selected from $C_1$-$C_{10}$-alkyl, $C_3$-$C_8$-cycloalkyl and $C_6$-$C_{10}$-aryl, wherein the carbon atoms of the aforementioned aliphatic, cycloaliphatic and aromatic radicals may optionally be substituted.

More preferably, $R^1$ and $R^2$, independently of each other, are selected from $C_1$-$C_{10}$-alkyl, which is unsubstituted;

$C_1$-$C_{10}$-alkyl which is substituted by $C_6$-$C_{10}$-aryl which in turn is unsubstituted or substituted by 1, 2 or 3 $C_1$-$C_{10}$-alkyl;

$C_3$-$C_8$-cycloalkyl, which is unsubstituted;

$C_3$-$C_8$-cycloalkyl, which is substituted by 1, 2 or 3 $C_1$-$C_{10}$-alkyl;

$C_6$-$C_{10}$-aryl which is unsubstituted;

$C_6$-$C_{10}$-aryl which is substituted by 1, 2 or 3 $C_1$-$C_{10}$-alkyl.

More preferably, $R^1$ and $R^2$, independently of each other, are selected from $C_1$-$C_8$-alkyl; $C_3$-$C_8$-cycloalkyl; $C_3$-$C_8$-cycloalkyl which carries 1, 2 or 3 $C_1$-$C_6$-alkyl substituents; $C_6$-$C_{10}$-aryl; and $C_6$-$C_{10}$-aryl which carries 1, 2 or 3 $C_1$-$C_6$-alkyl substituents. $R^1$ and $R^2$, independently of each other, are typically selected from methyl, ethyl, n-propyl, n-butyl, n-pentyl, n-hexyl, n-heptyl or n-octyl, isopropyl, sec-butyl, iso-butyl, tert-butyl, isopentyl, 2-pentyl, tert-pentyl, 2-ethylhexyl, cyclopentyl, cyclohexyl, cycloheptyl, 2-methylcyclohexyl, 2,4-dimethylcyclohexyl, 2,6-dimethylcyclohexyl, 2-ethylcyclohexyl, 2,4-diethylcyclohexyl, 2,6-diethylcyclohexyl, 2-isopropylcyclohexyl, 2,4-diisopropylcyclohexyl, 2,6-diisopropylcyclohexyl, phenyl, naphthyl, 2-methylphenyl, 2,4-dimethylphenyl, 2,6-dimethylphenyl, 2-ethylphenyl, 2,4-diethylphenyl, 2,6-diethylphenyl, 2-n-propylphenyl, 2,4-di-n-propylphenyl 2,6-di-(n-propyl)phenyl, 2-isopropylphenyl, 2,4-diisopropylphenyl and 2,6-diisopropylphenyl.

In a more particularly preferred embodiment, $R^1$ and $R^2$ have the same meaning and are phenyl, which carries 1, 2 or 3 $C_1$-$C_6$-alkyl substituents, especially $C_1$-$C_6$-alkyl substituents. If phenyl carries 2 or 3 $C_1$-$C_6$-alkyl substituents, the alkyl substituents preferably have the same meaning. Compounds of formula (I), where $R^1$ and $R^2$ have the same meaning and are phenyl which carries 2 $C_1$-$C_6$-alkyl substituents are especially preferred. In particular, $R^1$ and $R^2$ have the same meaning and are phenyl which carries 2 $C_1$-$C_6$-alkyl substituents in ortho, ortho'-position.

Preferably, the radicals $R^3$, $R^{10}$, $R^{11}$ and $R^{18}$ are phenyl or phenyl which carries one, two, three, four or five identical or different substitutents L. Preferred substituents L are $C_1$-$C_6$-alkyl, $C_1$-$C_6$-alkoxy-$C_1$-$C_6$-alkyl and $C_1$-$C_6$-alkoxy. Preferably, $R^3$, $R^{10}$, $R^{11}$ and $R^{18}$, independently of each other, are phenyl or phenyl which is substituted by 1 or 2 $C_1$-$C_6$-alkyl. Compounds of formula (I), wherein $R^3$, $R^{10}$, $R^{11}$ and $R^{18}$ are each phenyl are most preferred.

$R^4$, $R^5$, $R^6$, $R^7$, $R^8$, $R^9$, $R^{12}$, $R^{13}$, $R^{14}$, $R^{15}$, $R^{16}$ and $R^{17}$, independently of each other, are preferably selected from hydrogen, halogen, $C_1$-$C_{18}$-alkyl, $C_6$-$C_{10}$-aryl, $C_6$-$C_{10}$-aryl-$C_1$-$C_{10}$-alkylene, $C_6$-$C_{10}$-aryloxy and $C_6$-$C_{10}$-arylthio, where the aryl moiety of $C_6$-$C_{10}$-aryl, $C_6$-$C_{10}$-aryl-$C_1$-$C_{10}$-alkylene, $C_6$-$C_{10}$-aryloxy and $C_6$-$C_{10}$-arylthio is unsubstituted or substituted by one or more, such as 1, 2, 3 or 4 $C_1$-$C_{10}$-alkyl. Typically, $R^4$, $R^5$, $R^6$, $R^7$, $R^8$, $R^9$, $R^{12}$, $R^{13}$, $R^{14}$, $R^{15}$, $R^{16}$, and $R^{17}$, independently of each other, are selected from hydrogen, fluorine, chlorine, bromine, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl, decyl, phenyl, naphthyl, benzyl, 1-phenethyl, 2-phenethyl, 1-naphthylmethyl, 2-naphthylmethyl, phenyloxy, naphthyloxy, phenylthio, naphthylthio, where the aromatic moiety of the last eleven mentioned radicals is unsubstituted or substituted by one or more $C_1$-$C_{10}$-alkyl. More preferably, $R^4$, $R^5$, $R^6$, $R^7$, $R^8$, $R^9$, $R^{12}$, $R^{13}$, $R^{14}$, $R^{15}$, $R^{16}$ and $R^{17}$, independently of each other, are selected from hydrogen, $C_1$-$C_6$-alkyl and phenyl. Especially, $R^4$, $R^5$, $R^6$, $R^7$, $R^8$, $R^9$, $R^{12}$, $R^{13}$, $R^{14}$, $R^{15}$, $R^{16}$ and $R^{17}$ have the same meaning and are each hydrogen. Likewise especially, two of the radicals $R^4$, $R^5$, $R^6$ are hydrogen and one of the radicals $R^4$, $R^5$, $R^6$ is phenyl; two of the radicals $R^7$, $R^8$, $R^9$ are hydrogen and one of the radicals $R^7$, $R^8$, $R^9$ is phenyl, two of the radicals $R^{12}$, $R^{13}$, $R^{14}$ are hydrogen and one of the radicals $R^{12}$, $R^{13}$, $R^{14}$ is phenyl; two of the radicals $R^{15}$, $R^{16}$, $R^{17}$ are hydrogen and one of the radicals $R^{15}$, $R^{16}$, $R^{17}$ is phenyl. Likewise especially, two of the radicals $R^4$, $R^5$, $R^6$ are hydrogen and one of the radicals $R^4$, $R^5$, $R^6$ is $C_1$-$C_6$-alkyl; two of the radicals $R^7$, $R^8$, $R^9$ are hydrogen and one of the radicals $R^7$, $R^8$, $R^9$ is $C_1$-$C_6$-alkyl, two of the radicals $R^{12}$, $R^{13}$, $R^{14}$ are hydrogen and one of the radicals $R^{12}$, $R^{13}$, $R^{14}$ is $C_1$-$C_6$-alkyl; two of the radicals $R^{15}$, $R^{16}$, $R^{17}$ are hydrogen and one of the radicals $R^{15}$, $R^{16}$, $R^{17}$ is $C_1$-$C_6$-alkyl.

In another embodiment $R^4$, $R^5$, $R^6$, $R^7$, $R^8$, $R^9$, $R^{12}$, $R^{13}$, $R^{14}$, $R^{15}$, $R^{16}$ and $R^{17}$, independently of each other, are selected from hydrogen, halogen, $C_1$-$C_{18}$-alkyl, $C_6$-$C_{10}$-aryl, $C_6$-$C_{10}$-aryl-$C_1$-$C_{10}$-alkylene, $C_6$-$C_{10}$-aryloxy and $C_6$-$C_{10}$-arylthio, where the aryl moiety of $C_6$-$C_{10}$-aryl, $C_6$-$C_{10}$-aryl-$C_1$-$C_{10}$-alkylene, $C_6$-$C_{10}$-aryloxy, $C_6$-$C_{10}$-arylthio is unsubstituted or substituted by one or more $C_1$-$C_{10}$-alkyl, or where $R^5$ and $R^6$, $R^7$ and $R^8$, $R^{13}$ and $R^{14}$ and/or $R^{15}$ and $R^{16}$, together with the carbon atoms to which they are bonded, form a fused benzene ring wherein the fused benzene ring is unsubstituted or substituted. In case $R^5$ and $R^6$, $R^7$ and $R^8$, $R^{13}$ and $R^{14}$ and/or $R^{15}$ and $R^{16}$, together with the carbon atoms to which they are bonded, form a fused benzene ring, the benzene ring is preferably unsubstituted.

In particular preferred are compounds of formula (I), wherein $R^1$ and $R^2$ have the same meaning and are phenyl which carries 1, 2 or 3 $C_1$-$C_6$-alkyl substituents; $R^3$, $R^{10}$, $R^{11}$, and $R^{18}$ have the same meaning and are phenyl, which is unsubstituted or phenyl which is substituted by 1 or 2 $C_1$-$C_4$-alkyl; and $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R^{18}$ are each hydrogen. In particular, $R^3$, $R^{10}$, $R^{11}$, and $R^{18}$ are each phenyl.

Compounds of formula (I) can be prepared by reacting the appropriate chlorinated or brominated perylene bisimide of formula (1)

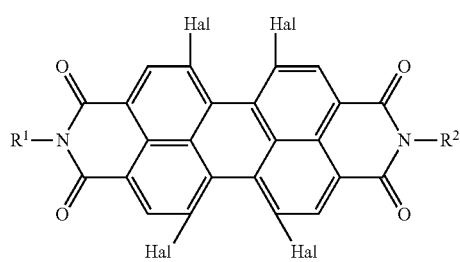

(1)

where
Hal is in each case bromine or in each case chlorine; and $R^1$ and $R^2$ are as defined above
with a 2-phenylphenol compound of formula (2) and, if appropriate, a 2-phenylphenol compound of formulae (3), (4) and/or (5)

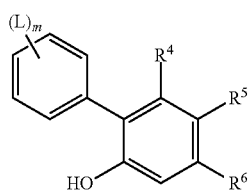

(2)

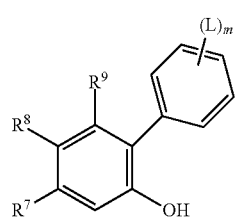

(3)

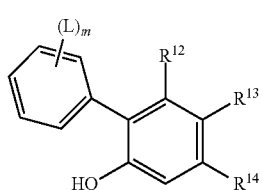

(4)

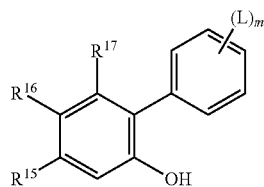

(5)

where
m is 0, 1, 2, 3, 4 or 5;
L is as defined above; and $R^4$, $R^5$, $R^6$, $R^7$, $R^8$, $R^9$, $R^{12}$, $R^{13}$, $R^{14}$, $R^{15}$, $R^{16}$ and $R^{17}$ are as defined above.

The 2-phenylbiphenol of formulae (3) (4), and/or (5) may also be as defined for the 2-phenylphenol of formula (2) (if only one, two, three or four 2-phenylphenol of the formula (2) is/are used for halogen replacement reaction).

The reaction is usually carried out in the presence of a base. Suitable bases are in particular inorganic alkali metal or alkaline earth metal bases, the alkali metal bases being particularly suitable. Examples of inorganic bases are the carbonates and hydrogencarbonates, hydroxides, hydrides and amides of alkali metals and alkaline earth metals. Preferred bases are the carbonates and hydrogencarbonates, particular preference being given to the carbonates. Preferred alkali metals are lithium, sodium, potassium and cesium; particularly suitable alkaline earth metals are magnesium and calcium. It will be appreciated that it is also possible to use base mixtures. Very particularly preferred bases are lithium carbonate, sodium carbonate, potassium carbonate and cesium carbonate.

The reaction is usually carried out in the presence of a polar, aprotic solvent. Suitable solvents are especially aliphatic carboxamides, preferably N,N-di-$C_1$-$C_4$-alkyl-$C_1$-$C_4$-carboxamides, lactams such as dimethylformamide, diethylformamide, dimethylacetamide, dimethylbutyramide and N-methyl-2-pyrrolidone (NMP), nitriles such as acetonitrile. It is also possible to use mixtures of polar, aprotic solvents. Particular preference is given to NMP.

The reaction temperature is generally within the range from room temperature to the boiling point of the solvent, preferably room temperature to 160° C.

Compounds of formula (1) can be prepared according to literature methods, for example from 1,6,7,12-tetrachloroperylene tetracarboxylic acid dianhydride or 1,6,7,12-tetrabromoperylene tetracarboxylic acid dianhydride of formula (6)

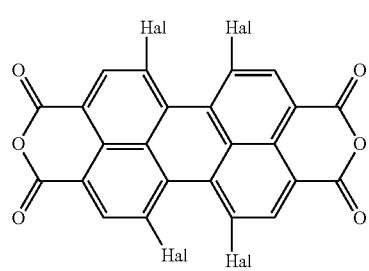

(6)

where
Hal is in each case bromine or in each case chlorine;
by condensation with a primary amine of formula $R^1$—$NH_2$ and, if appropriate a primary amine of formula $R^2$—$NH_2$, where $R^1$ and $R^2$ are as defined above, where $R^2$ may also be as defined for $R^1$ (if only one amine of the formula $R^1$—$NH_2$ is used for the imidation). The imidation reaction is carried out according to standard methods, e.g. as described by Bartholomew et al., in Chem. Commun., 2008, 6594-6596 including Supplementary Material (ESI) for Chemical Communications. 1,6,7,12-tetrachloroperylene tetracarboxylic acid dianhydride is commercially available; 1,6,7,12-tetrabromoperylene tetracarboxylic acid dianhydride can be prepared as described by Bartholomew et al., in Chem. Commun., 2008, 6594-6596 including Supplementary Material (ESI).

Compounds of formulae (2), (3), (4) and (5) are commercially available or can be prepared according to literature methods.

The compound of the formula (I) or mixtures thereof as defined above can be used for a whole series of end uses for example as fluorescent dye/colorant in color converters. Thus, it is possible to convert light produced by a white LED having a CCT between 6000 K to 20000 K to light having a lower CCT (i.e. warmer white light) by passing light generated by said white LED through a color converter comprising the compound of formula (I). Accordingly, it is possible to convert light produced by a white LED having a CCT between 6,000 K to 20 000 K to light having a CCT below 6,000 K, for example in a range from 2,000 K to 5,000 K or 2500 K to 4000 K. Likewise, it is possible to convert light produced by a blue LED with a center wavelength of emission between 420 nm and 480 nm to light of a second longer wavelength by passing light generated by said LED through a color converter comprising the compound of formula (I).

Thus, in a second aspect, the invention provides a color converter comprising at least one compound of the formula (I) or mixtures thereof as fluorescent dye/colorant as defined above and at least one polymer as a matrix, wherein the polymer is selected from the group consisting of polystyrene (PS), polycarbonate (PC), polymethyl methacrylate (PMMA), polyvinylpyrrolidone, polymethacrylate, polyvinyl acetate, polyvinyl chloride, polybutene, silicone, polyacrylate, epoxy resin, polyvinyl alcohol, poly(ethylene vinylalcohol)-copolymer (EVA, EVOH), polyacrylonitrile, polyvinylidene chloride, poly(styrene-)acrylonitrile (SAN), polybutylene terephthalate (PBT), polyethylene terephthalate (PET), polyvinyl butyrate (PVB), polyvinyl chloride (PVC), polyamides (PA), polyoxymethylenes, polyimides, polyetherimides and mixtures thereof.

The following polymers are preferred: polystyrene, polycarbonate, polymethyl methacrylate, polyvinylpyrrolidone, polymethacrylate, polyvinyl acetate, polyvinyl chloride, polybutene, silicone, polyacrylate, epoxy resin, polyvinyl alcohol, poly(ethylene vinylalcohol)-copolymer, polyacrylonitrile, polyvinylidene chloride, poly(styrene-acrylonitrile), polybutylene terephthalate, polyethylene terephthalate, polyvinyl butyrate, polyvinyl chloride, polyamides, polyoxymethylenes, polyimides, polyetherimides and mixtures thereof.

Especially, the at least one polymer consists essentially of polystyrene, polycarbonate, polyethylene terephthalate or mixtures thereof.

Polystyrene is understood here to mean, inter alia, all homo- or copolymers which result from polymerization of styrene and/or derivatives of styrene. Derivatives of styrene are, for example, alkylstyrenes such as alpha-methylstyrene, ortho-, meta-, para-methylstyrene, para-butylstyrene, especially para-tert-butylstyrene, alkoxystyrene such as para-methoxystyrene, para-butoxystyrene, para-tert-butoxystyrene. In general, suitable polystyrenes have a mean molar mass $M_n$ of 10,000 to 1,000,000 g/mol (determined by GPC), preferably 20,000 to 750 000 g/mol, more preferably 30,000 to 500 000 g/mol.

In a preferred embodiment, the matrix of the color converter consists essentially or completely of a homopolymer of styrene or styrene derivatives. More particularly, the polymer consists of polystyrene.

In a further preferred embodiments of the invention, the matrix consists essentially or completely of a styrene copolymer, which are likewise regarded as polystyrene in the context of this application. Styrene copolymers may comprise, as further constituents, for example, butadiene, acrylonitrile, maleic anhydride, vinylcarbazole or esters of acrylic, methacrylic or itaconic acid as monomers. Suitable styrene copolymers generally comprise at least 20% by weight of styrene, preferably at least 40% and more preferably at least 60% by weight of styrene. In another embodiment, they comprise at least 90% by weight of styrene.

Preferred styrene copolymers are styrene-acrylonitrile copolymers (SAN) and acrylonitrile-butadiene-styrene copolymers (ABS), styrene-1,1'-diphenylethene copolymers, acrylic ester-styrene-acrylonitrile copolymers (ASA), methyl methacrylate-acrylonitrile-butadiene-styrene copolymers (MABS). A further preferred polymer is alpha-methylstyrene-acrylonitrile copolymer (AMSAN). The styrene homo- or copolymers can be prepared, for example, by free-radical polymerization, cationic polymerization, anionic polymerization or under the influence of organometallic catalysts (for example Ziegler-Natta catalysis). This can lead to isotactic, syndiotactic or atactic polystyrene or copolymers. They are preferably prepared by free-radical polymerization. The polymerization can be performed as a suspension polymerization, emulsion polymerization, solution polymerization or bulk polymerization. The preparation of suitable polystyrenes is described, for example, in Oscar Nuyken, Polystyrenes and Other Aromatic Polyvinyl Compounds, in Kricheldorf, Nuyken, Swift, N.Y. 2005, p. 73-150 and references cited therein; and in Elias, Macromolecules, Weinheim 2007, p. 269-275.

In another preferred embodiment, the polymer consists of polyethylene terephthalate. Polyethylene terephthalate is obtainable by condensation of ethylene glycol with terephthalic acid.

Likewise more particularly, the polymer consists of polycarbonate. Polycarbonates are polyesters of carbonic acid with aromatic or aliphatic dihydroxyl compounds. Preferred dihydroxyl compounds are, for example, methylenediphenylenedihydroxyl compounds, for example bisphenol A. One means of preparing polycarbonates is the reaction of suitable dihydroxyl compounds with phosgene in an interfacial polymerization. Another means is the reaction with diesters of carbonic acid such as diphenyl carbonate in a condensation polymerization. The preparation of suitable polycarbonates is described, for example, in Elias, Macromolecules, Weinheim 2007, p. 343-347.

In a preferred embodiment, polymers which have been polymerized with exclusion of oxygen are used. Preferably, the monomers during the polymerization comprised a total of not more than 1000 ppm of oxygen, more preferably not more than 100 ppm and especially preferably not more than 10 ppm.

Suitable polymers may comprise, as further constituents, additives such as flame retardants, antioxidants, light stabilizers, UV absorbers, free-radical scavengers, antistats. Stabilizers of this kind are known to those skilled in the art.

Suitable antioxidants or free-radical scavengers are, for example, phenols, especially sterically hindered phenols such as butylhydroxyanisole (BHA) or butylhydroxytoluene (BHT), or sterically hindered amines (HALS). Stabilizers of this kind are sold, for example, by BASF under the Irganox® trade name. In some cases, antioxidants and free-radical scavengers can be supplemented by secondary stabilizers such as phosphites or phosphonites, as sold, for example, by BASF under the Irgafos® trade name.

Suitable UV absorbers are, for example, benzotriazoles such as 2-(2-hydroxyphenyl)-2H-benzotriazole (BTZ), triazines such as (2-hydroxyphenyl)-s-triazine (HPT), hydroxybenzophenones (BP) or oxalanilides. UV absorbers of this kind are sold, for example, by BASF under the Uvinul® trade name.

In a preferred embodiment of the invention, suitable polymers do not comprise any antioxidants or free-radical scavengers.

In one embodiment of the invention, suitable polymers are transparent polymers.

In another embodiment, suitable polymers are opaque polymers.

The polymers mentioned above serve as a matrix material for the compound of formula (I) or mixtures thereof. The inventive fluorescent dye(s), i.e. the compound of the formula (I) or a mixture thereof, i.e. a mixture comprising at least two different compounds of formula (I), may either be dissolved in the polymer or may be in the form of a homogeneously distributed mixture. In a preferred embodiment, the fluorescent dye of formula (I) or a mixture therof is dissolved in the polymer. The compound of the formula (I) is a red-fluorescing dye.

A skilled person will readily appreciate that the specific concentration of inventive compound of formula (I) needed for effective wavelength conversion depends on the type of LED chosen to generate light. A higher concentration of dye(s) is usually required for the conversion of light generated by a blue LED in comparison to a white LED to achieve the same color temperature of white light.

According to a first embodiment, the color converter does not comprise an organic fluorescent dye different from the compound of formula (I). In this case, the concentration of the red organic fluorescent dye of formula (I) and, if appropriate, mixtures thereof, is typically 0.0001 to 0.5% by weight, for example 0.001 to 0.1% by weight, or 0.002 to 0.1% by weight, based on the amount of polymer used.

In further embodiments, there is provided a fluorescent dye blend comprising mandatorily the compound of the formula (I) or a mixture comprising at least two different compounds of formula (I) and at least one further organic fluorescent dye which may be used in the above described color converter.

Suitable further organic fluorescent dyes may be any organic fluorescent dye that absorbs light in the wavelength range from 400 to 500 nm and emits light having a longer wavelength than that of the absorbed light, especially in the wavelength range above 450 nm, for example in the wavelength range from 450 to 600 nm or 450 to 650 nm.

According to a second embodiment, the color converter comprises, in addition to the at least one organic red-fluorescent dye of formula (I) or mixtures thereof, one further organic fluorescent dye or mixtures of said further fluorescent dye.

According to a third embodiment, the color converter comprises, in addition to the at least one organic red-fluorescent dye of formula (I) or mixtures thereof, two or more further organic fluorescent dyes.

Suitable further organic fluorescent dyes are green-fluorescent dyes, yellow-green fluorescent dyes, yellow-fluorescent dyes, orange-fluorescent dyes and red-fluorescent dyes. Preferably, fluorescent dyes are combined with one another such that color converters are provided for use to make white light sources with low CCT (<6000K) and high color rendering (e.g. 90 or higher).

In particularly, the at least one further organic fluorescent dye is selected from
(i) a cyanated naphthoylbenzimidazole compound of the formula (II)

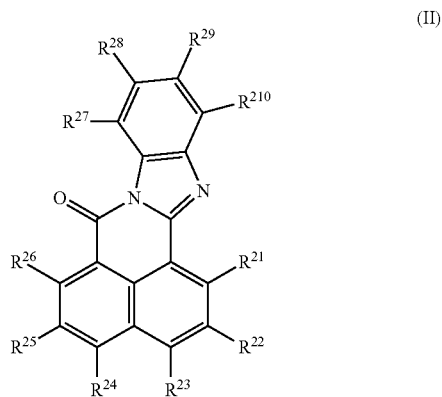

(II)

and mixtures thereof,
wherein
R21, R22, R23, R24, R25, R26, R27, R28, R29 and R210 are each independently hydrogen, cyano or aryl which is unsubstituted or has one or more identical or different substituents R2Ar,
where
each $R^{2Ar}$ is independently selected from cyano, hydroxyl, mercapto, halogen, $C_1$-$C_{20}$-alkoxy, $C_1$-$C_{20}$-alkylthio, nitro, $-NR^{2Ar2}R^{2Ar3}$, $-NR^{2Ar2}COR^{2Ar3}$, $-CONR^{2Ar2}R^{2Ar3}$, $-SO_2NR^{2Ar2}R^{2Ar3}$, $-COOR^{2Ar2}$, $-SO_3R^{2Ar2}$,
$C_1$-$C_{30}$-alkyl, $C_2$-$C_{30}$-alkenyl, $C_2$-$C_{30}$-alkynyl, where the three latter radicals are unsubstituted or bear one or more $R^{2a}$ groups,
$C_3$-$C_8$-cycloalkyl, 3- to 8-membered heterocyclyl, where the two latter radicals are unsubstituted or bear one or more $R^{2b}$ groups, aryl, U-aryl, heteroaryl and U-heteroaryl, where the four latter radicals are unsubstituted or bear one or more $R^{2b}$ groups,
where
each $R^{2a}$ is independently selected from cyano, hydroxyl, oxo, mercapto, halogen, $C_1$-$C_{20}$-alkoxy, $C_1$-$C_{20}$-alkylthio, nitro, $-NR^{2Ar2}R^{2Ar3}$, $-NR^{2Ar2}COR^{2Ar3}$, $-CONR^{2Ar2}R^{2Ar3}$, $-SO_2NR^{2Ar2}R^{2Ar3}$, $-COOR^{2Ar2}$, $-SO_3R^{2Ar2}$, $C_3$-$C_8$-cycloalkyl, 3- to 8-membered heterocyclyl, aryl and heteroaryl, where the cycloalkyl, heterocyclyl, aryl and heteroaryl radicals are unsubstituted or bear one or more $R^{2b}$ groups;
each $R^{2b}$ is independently selected from cyano, hydroxyl, oxo, mercapto, halogen, $C_1$-$C_{20}$-alkoxy, $C_1$-$C_{20}$-alkylthio, nitro, $-NR^{2Ar2}R^{2Ar3}$, $-NR^{2Ar2}COR^{2Ar3}$, $-CONR^{2Ar2}R^{2Ar3}$, $-SO_2NR^{2Ar2}R^{2Ar3}$, $-COOR^{2Ar2}$, $-SO_3R^{2Ar2}$, $C_1$-$C_{18}$-alkyl, $C_2$-$C_{18}$-alkenyl, $C_2$-$C_{18}$-alkynyl, $C_3$-$C_8$-cycloalkyl, 3- to 8-membered heterocyclyl, aryl and heteroaryl, where the four latter radicals are unsubstituted or bear one or more $R^{2b1}$ groups, each $R^{2b1}$ is independently selected from cyano, hydroxyl, mercapto, oxo, nitro, halogen, $-NR^{2Ar2}R^{2Ar3}$, $-NR^{2Ar2}COR^{2Ar3}$, $-CONR^{2Ar2}R^{2Ar3}$, $-SO_2NR^{2Ar2}R^{2Ar3}$, $-COOR^{2Ar2}$, $-SO_3R^{2Ar2}$, $-SO_3R^{2Ar2}$, $C_1$-$C_{18}$-alkyl, $C_2$-$C_{18}$-alkenyl, $C_2$-$C_{18}$-alkynyl, $C_1$-$C_{12}$-alkoxy, and $C_1$-$C_{12}$-alkylthio, U is an $-O-$, $-S-$, $-NR^{2Ar1}-$, $-CO-$, $-SO-$ or $-SO_2-$ moiety;

$R^{2Ar1}$, $R^{2Ar2}$, $R^{2Ar3}$ are each independently hydrogen, $C_1$-$C_{18}$-alkyl, 3- to 8-membered cycloalkyl, 3- to 8-membered heterocyclyl, aryl or heteroaryl, where alkyl is unsubstituted or bears one or more $R^{2a}$ groups, where 3- to 8-membered cycloalkyl, 3- to 8-membered heterocyclyl, aryl and heteroaryl are unsubstituted or bear one or more $R^{2b}$ groups;

with the proviso that the compound of the formula (II) comprises at least one cyano group;

(ii) a cyanated perylene compound of the formula (III)

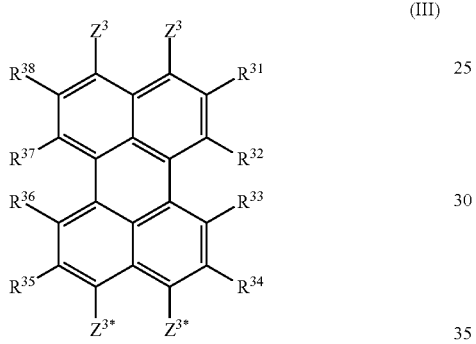

(III)

and mixtures thereof,
in which
one of the $Z^3$ substituents is cyano and the other $Z^3$ substituent is $CO_2R^{39}$, $CONR^{310}R^{311}$, $C_1$-$C_{18}$-alkyl, $C_2$-$C_{18}$-alkenyl, $C_2$-$C_{18}$-alkynyl, $C_3$-$C_{12}$-cycloalkyl or $C_6$-$C_{14}$-aryl, where
$C_1$-$C_{18}$-alkyl, $C_2$-$C_{18}$-alkenyl, $C_2$-$C_{18}$-alkynyl are unsubstituted or bear one or more identical or different $Z^{3a}$ substituents,
$C_3$-$C_{12}$-cycloalkyl is unsubstituted or bears one or more identical or different $Z^{3b}$ substituents, and
$C_6$-$C_{14}$-aryl is unsubstituted or bears one or more identical or different $Z^{3Ar}$ substituents;

one of the $Z^{3*}$ substituents is cyano and the other $Z^{3*}$ substituent is $CO_2R^{39}$, $CONR^{310}R^{311}$, $C_1$-$C_{18}$-alkyl, $C_2$-$C_{18}$-alkenyl, $C_2$-$C_{18}$-alkynyl, $C_3$-$C_{12}$-cycloalkyl or $C_6$-$C_{14}$-aryl, where
$C_1$-$C_{18}$-alkyl, $C_2$-$C_{18}$-alkenyl, $C_2$-$C_{18}$-alkynyl are unsubstituted or bear one or more identical or different $Z^{3a}$ substituents,
$C_3$-$C_{12}$-cycloalkyl is unsubstituted or bears one or more identical or different $Z^{3b}$ substituents, and
$C_6$-$C_{14}$-aryl is unsubstituted or bears one or more identical or different $Z^{3Ar}$ substituents;

$R^{31}$, $R^{32}$, $R^{33}$, $R^{34}$, $R^{35}$, $R^{36}$, $R^{37}$ and $R^{38}$ are each independently selected from hydrogen, cyano, bromine and chlorine,
with the proviso that 1, 2, 3, 4, 5, 6, 7 or 8 of the $R^{31}$, $R^{32}$, $R^{33}$, $R^{34}$, $R^{35}$, $R^{36}$, $R^{37}$ or $R^{38}$ substituents are cyano;

where
$R^{39}$ is hydrogen, $C_1$-$C_{10}$-alkyl, $C_2$-$C_{10}$-alkenyl, $C_2$-$C_{10}$-alkynyl, $C_3$-$C_{12}$-cycloalkyl or $C_6$-$C_{14}$-aryl, where
$C_1$-$C_{10}$-alkyl, $C_2$-$C_{10}$-alkenyl, $C_2$-$C_{10}$-alkynyl are unsubstituted or bear one or more identical or different $R^{3a}$ substituents,
$C_3$-$C_{12}$-cycloalkyl is unsubstituted or bears one or more identical or different $R^{3b}$ substituents and
$C_6$-$C_{14}$-aryl is unsubstituted or bears one or more identical or different $R^{3Ar}$ substituents;

$R^{310}$ and $R^{311}$ are each independently hydrogen, $C_1$-$C_{10}$-alkyl, $C_2$-$C_{10}$-alkenyl, $C_2$-$C_{10}$-alkynyl, $C_3$-$C_{12}$-cycloalkyl or $C_6$-$C_{14}$-aryl, where
$C_1$-$C_{10}$-alkyl, $C_2$-$C_{10}$-alkenyl, $C_2$-$C_{10}$-alkynyl are unsubstituted or bear one or more identical or different $R^{3a}$ substituents,
$C_3$-$C_{12}$-cycloalkyl is unsubstituted or bears one or more identical or different $R^{3b}$ substituents and
$C_6$-$C_{14}$-aryl is unsubstituted or bears one or more identical or different $R^{3Ar}$ substituents;

each $Z^{3a}$ is independently halogen, hydroxyl, $NR^{310a}R^{311a}$, $C_1$-$C_{10}$-alkoxy, $C_1$-$C_{10}$-haloalkoxy, $C_1$-$C_{10}$-alkylthio, $C_3$-$C_{12}$-cycloalkyl, $C_6$-$C_{14}$-aryl, $C(=O)R^{39a}$; $C(=O)OR^{39a}$ or $C(O)NR^{310a}R^{311a}$, where
$C_3$-$C_{12}$-cycloalkyl is unsubstituted or bears one or more identical or different $R^{3b}$ substituents and
$C_6$-$C_{14}$-aryl is unsubstituted or bears one or more identical or different $R^{3Ar}$ substituents;

each $Z^{3b}$ and each $Z^{3Ar}$ is independently halogen, hydroxyl, $NR^{310a}R^{311a}$, $C_1$-$C_{10}$-alkyl, $C_1$-$C_{10}$-alkoxy, $C_1$-$C_{10}$-haloalkoxy, $C_1$-$C_{10}$-alkylthio, $C(=O)R^{39a}$; $C(=O)OR^{39a}$ or $C(O)NR^{310a}R^{311a}$;

each $R^{3a}$ is independently halogen, hydroxyl, $C_1$-$C_{10}$-alkoxy, $C_3$-$C_{12}$-cycloalkyl or $C_6$-$C_{14}$-aryl;

each $R^{3b}$ is independently halogen, hydroxyl, $C_1$-$C_{10}$-alkyl, $C_1$-$C_{10}$-alkoxy, $C_1$-$C_{10}$-haloalkoxy, $C_1$-$C_{10}$-alkylthio, $C_2$-$C_{10}$-alkenyl, $C_2$-$C_{10}$-alkynyl, $C_3$-$C_{12}$-cycloalkyl or $C_6$-$C_{14}$-aryl;

each $R^{3Ar}$ is independently halogen, hydroxyl, $C_1$-$C_{10}$-alkyl, $C_1$-$C_{10}$-alkoxy, $C_1$-$C_{10}$-haloalkoxy, $C_1$-$C_{10}$-alkylthio, $C_2$-$C_{10}$-alkenyl, $C_2$-$C_{10}$-alkynyl, $C_3$-$C_{12}$-cycloalkyl or $C_6$-$C_{14}$-aryl;

$R^{39a}$ is hydrogen, $C_1$-$C_{10}$-alkyl, $C_2$-$C_{10}$-alkenyl, $C_2$-$C_{10}$-alkynyl, $C_3$-$C_{12}$-cycloalkyl or $C_6$-$C_{14}$-aryl; and $R^{310a}$, $R^{311a}$ are each independently hydrogen, $C_1$-$C_{10}$-alkyl, $C_2$-$C_{10}$-alkenyl, $C_2$-$C_{10}$-alkynyl, $C_3$-$C_{12}$-cycloalkyl or $C_6$-$C_{14}$-aryl;

(iii) a cyanated compound of the formula (IV)

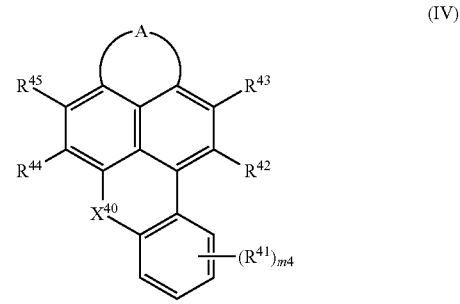

(IV)

and mixtures thereof, wherein m4 is 0, 1, 2, 3 or 4;

each $R^{41}$ independently from each other is selected from bromine, chlorine, cyano, —$NR^{4a}R^{4b}$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, $C_6$-$C_{24}$-aryl-$C_1$-$C_{10}$-alkylene, where the rings of cycloalkyl, heterocycloalkyl, heteroaryl, aryl, aryloxy in the six last-mentioned radicals are unsubstituted or substituted with 1, 2, 3, 4 or 5 identical or different radicals $R^{41a}$ and where $C_1$-$C_{24}$-alkyl, $C_1$-$C_{24}$-haloalkyl, $C_1$-$C_{24}$-alkoxy, and the alkylene moiety of $C_6$-$C_{24}$-aryl-$C_1$-$C_{10}$-alkylene may be interrupted by one or more groups selected from O, S and $NR^{4c}$;

at least one of the radicals $R^{42}$, $R^{43}$, $R^{44}$ and $R^{45}$ is CN, and the remaining radicals, independently from each other, are selected from hydrogen, chlorine and bromine;

$X^{40}$ is O, S, SO or $SO_2$;

A is a diradical selected from diradicals of the general formulae (A.1), (A.2), (A.3), and (A.4)

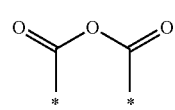
(A.1)

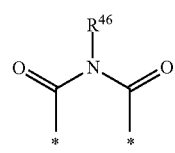
(A.2)

(A.3)

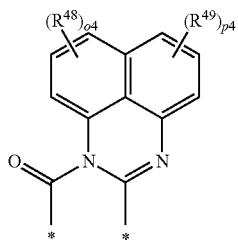
(A.4)

wherein

* in each case denotes the point of attachments to the remainder of the molecule;

n4 is 0, 1, 2, 3 or 4;

o4 is 0, 1, 2 or 3;

p4 is 0, 1, 2 or 3;

$R^{46}$ is hydrogen, $C_1$-$C_{24}$-alkyl, $C_1$-$C_{24}$-haloalkyl, $C_3$-$C_{24}$-cycloalkyl, $C_6$-$C_{24}$-aryl or $C_6$-$C_{24}$-aryl-$C_1$-$C_{10}$-alkylene, where the rings of cycloalkyl, aryl, and aryl-alkylene in the three last-mentioned radicals are unsubstituted or substituted with 1, 2, 3, 4 or 5 identical or different radicals $R^{46a}$, and where $C_1$-$C_{24}$-alkyl, $C_1$-$C_{24}$-haloalkyl and the alkylene moiety of $C_6$-$C_{24}$-aryl-$C_1$-$C_{10}$-alkylene may be interrupted by one or more heteroatoms or heteroatomic groups selected from O, S and $NR^{4c}$;

each $R^{47}$ independently from each other is selected from bromine, chlorine, cyano, —$NR^{4a}R^{4b}$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, $C_6$-$C_{24}$-aryl-$C_1$-$C_{10}$-alkylene, where the rings of cycloalkyl, heterocycloalkyl, heteroaryl, aryl and aryl-alkylene in the six last-mentioned radicals are unsubstituted or substituted with 1, 2, 3, 4 or 5 identical or different radicals $R^{47a}$ and where $C_1$-$C_{24}$-alkyl, $C_1$-$C_{24}$-haloalkyl, $C_1$-$C_{24}$-alkoxy, $C_1$-$C_{24}$-haloalkoxy, and the alkylene moiety of $C_6$-$C_{24}$-aryl-$C_1$-$C_{10}$-alkylene may be interrupted by one or more groups selected from O, S and $NR^{4c}$;

each $R^{48}$ independently from each other is selected from bromine, chlorine, cyano, $NR^{4a}R^{4b}$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, $C_6$-$C_{24}$-aryl-$C_1$-$C_{10}$-alkylene, where the rings of cycloalkyl, heterocycloalkyl, heteroaryl, aryl and aryl-alkylene in the six last-mentioned radicals are unsubstituted or substituted with 1, 2, 3, 4 or 5 identical or different radicals $R^{48a}$ and where $C_1$-$C_{24}$-alkyl, $C_1$-$C_{24}$-haloalkyl, $C_1$-$C_{24}$-alkoxy, $C_1$-$C_{24}$-haloalkoxy, and the alkylene moiety of $C_6$-$C_{24}$-aryl-$C_1$-$C_{10}$-alkylene may be interrupted by one or more groups selected from O, S and $NR^{4c}$;

each $R^{49}$ independently from each other is selected from bromine, chlorine, cyano, $NR^{4a}R^{4b}$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, $C_6$-$C_{24}$-aryl-$C_1$-$C_{10}$-alkylene, where the rings of cycloalkyl, heterocycloalkyl, heteroaryl, aryl and aryl-alkylene in the six last-mentioned radicals are unsubstituted or substituted with 1, 2, 3, 4 or 5 identical or different radicals $R^{49a}$ and where $C_1$-$C_{24}$-alkyl, $C_1$-$C_{24}$-haloalkyl, $C_1$-$C_{24}$-alkoxy, $C_1$-$C_{24}$-haloalkoxy, and the alkylene moiety of $C_6$-$C_{24}$-aryl-$C_1$-$C_{10}$-alkylene may be interrupted by one or more groups selected from O, S and $NR^{4c}$;

$R^{41a}$, $R^{46a}$, $R^{47a}$, $R^{48a}$, $R^{49a}$ are independently of one another selected from $C_1$-$C_{24}$-alkyl, $C_1$-$C_{24}$-fluoroalkyl, $C_1$-$C_{24}$-alkoxy, fluorine, chlorine and bromine;

$R^{4a}$, $R^{4b}$, $R^{4c}$ are independently of one another are selected from hydrogen, $C_1$-$C_{20}$-alkyl, $C_3$-$C_{24}$-cycloalkyl, heterocycloalkyl, heteroaryl and $C_6$-$C_{24}$-aryl;

(iv) a benzoxanthene compound of the formula (V)

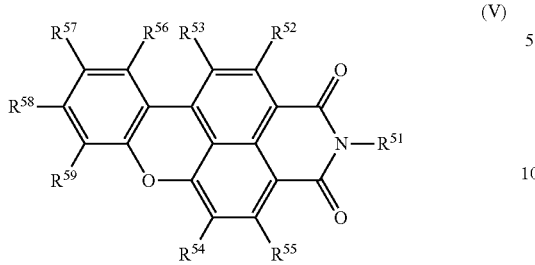

and mixtures thereof,
wherein
$R^{51}$ is phenyl which is unsubstituted or carries 1, 2, 3, 4, or 5 substituents selected from halogen, $R^{511}$, $OR^{552}$, $NHR^{552}$ and $NR^{552}R^{557}$;
$R^{52}$, $R^{53}$, $R^{54}$, $R^{55}$, $R^{56}$, $R^{57}$, $R^{58}$ and $R^{59}$ are independently of each other selected from hydrogen, halogen, $R^{553}$, $OR^{553}$, $NHR^{553}$ and $NR^{553}R^{554}$, wherein
$R^{511}$ is selected from $C_2$-$C_{18}$-alkyl, $C_6$-$C_{24}$-aryl and heteroaryl;
$R^{552}$ and $R^{557}$ are independently of each other selected from $C_1$-$C_{18}$-alkyl, $C_6$-$C_{24}$-aryl and heteroaryl; and
$R^{553}$ and $R^{554}$ are independently of each other selected from $C_1$-$C_{18}$-alkyl, $C_6$-$C_{24}$-aryl and heteroaryl;
(v) a fluorescent compound comprising at least one structural unit of formula (VI)

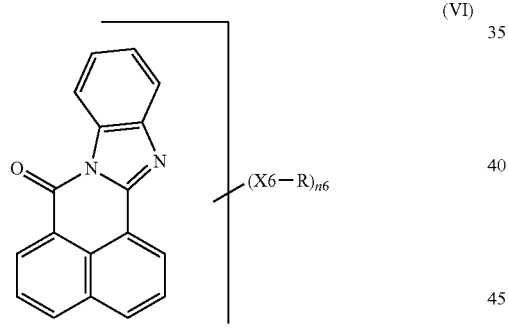

where one or more CH groups of the six-membered ring of the benzimidazole structure shown may be replaced by nitrogen and where the symbols are each defined as follows:
n6 is a number from 0 to (10-p6) for each structural unit of the formula (VI); where p6 is the number of CH units which have been replaced by nitrogen in the six-membered ring of the benzimidazole structure shown;
X6 is a chemical bond, O, S, SO, $SO_2$, $NR^{61}$; and
R is an aliphatic radical, cycloaliphatic radical, aryl, heteroaryl, each of which may bear substituents, an aromatic or heteroaromatic ring or ring system, each of which is fused to other aromatic rings of the structural unit of the formula (VI) is F, $C_1$, Br, CN, H when X6 is not a chemical bond;
where two R radicals may be joined to give one cyclic radical and
where X6 and R, when n6>one, may be the same or different;

$R^{61}$ is each independently hydrogen, $C_1$-$C_{18}$-alkyl or cycloalkyl, the carbon chain of which may comprise one or more —O—, —S—, —CO—, —SO— and/or —$SO_2$— moieties and which may be mono- or polysubstituted;
aryl or heteroaryl which may be mono- or polysubstituted;
and mixtures thereof;
(vi) a perylene compound of the formulae (VII), (VIII), (IX) or (X)

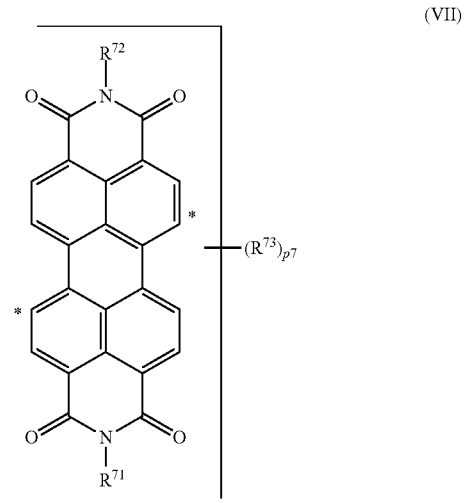

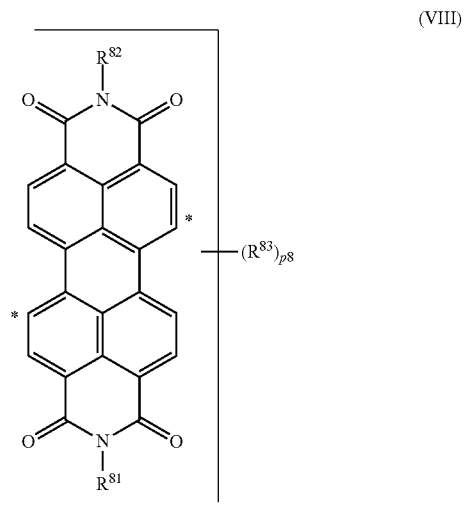

-continued

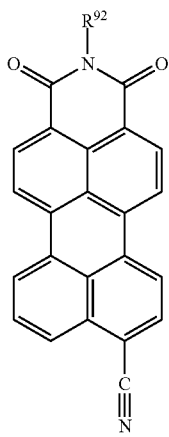

(IX)

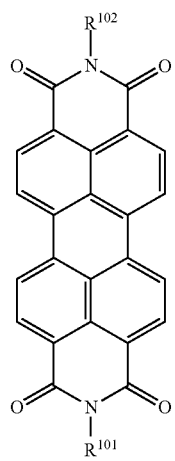

(X)

and mixtures thereof,
where
p7 is 2,
$R^{71}$, $R^{72}$ are each independently $C_1$-$C_{30}$-alkyl, $C_3$-$C_8$-cycloalkyl, aryl, heteroaryl, aryl-$C_1$-$C_{10}$-alkylene, where the aromatic ring in the three latter radicals is unsubstituted or mono- or polysubstituted by $C_1$-$C_{10}$-alkyl;
$R^{73}$ is aryloxy which is unsubstituted or mono- or polysubstituted by $C_1$-$C_{10}$-alkyl or $C_6$-$C_{10}$-aryl, where the $R^{73}$ radicals are at the positions indicated by *;
p8 is 2;
$R^{81}$, $R^{82}$ are each independently $C_1$-$C_{30}$-alkyl, $C_3$-$C_8$-cycloalkyl, aryl, heteroaryl, aryl-$C_1$-$C_{10}$-alkylene, where the aromatic ring in the three latter radicals is unsubstituted or mono- or polysubstituted by $C_1$-$C_{10}$-alkyl;
$R^{83}$ is aryloxy which is unsubstituted or mono- or polysubstituted by $C_1$-$C_{10}$-alkyl or $C_6$-$C_{10}$-aryl, where the $R^{83}$ radicals are at the positions indicated by *;
$R^{92}$ is $C_1$-$C_{30}$-alkyl, $C_3$-$C_8$-cycloalkyl, aryl, heteroaryl, aryl-$C_1$-$C_{10}$-alkylene, where the aromatic ring in the three latter radicals is unsubstituted or mono- or polysubstituted by $C_1$-$C_{10}$-alkyl;
$R^{101}$, $R^{102}$ are each independently $C_1$-$C_{30}$-alkyl, $C_3$-$C_8$-cycloalkyl, aryl, heteroaryl, aryl-$C_1$-$C_{10}$-alkylene, where the aromatic ring in the three latter radicals is unsubstituted or mono- or polysubstituted by $C_1$-$C_{10}$-alkyl;

(vii) a perylene bisimide compound of the formula (XI)

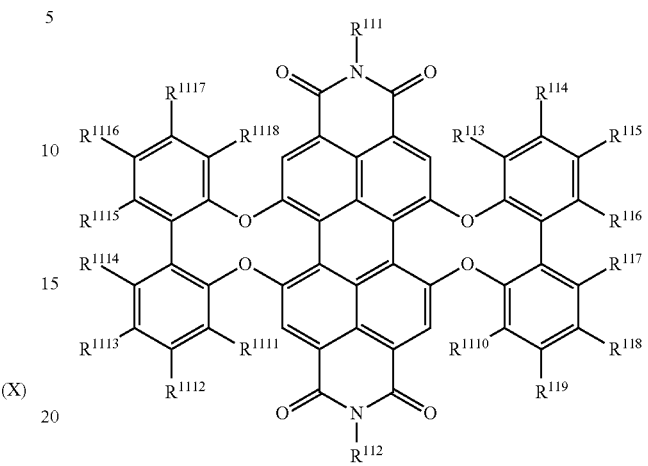

(XI)

and mixtures thereof,
wherein
$R^{111}$ and $R^{112}$, independently of each other, are selected from hydrogen, in each case unsubstituted or substituted $C_1$-$C_{30}$-alkyl, polyalkyleneoxy, $C_1$-$C_{30}$-alkoxy, $C_1$-$C_{30}$-alkylthio, $C_3$-$C_{20}$-cycloalkyl, $C_3$-$C_{20}$-cycloalkyloxy, $C_6$-$C_{24}$-aryl and $C_6$-$C_{24}$-aryloxy;
$R^{113}$, $R^{114}$, $R^{115}$, $R^{116}$, $R^{117}$, $R^{118}$, $R^{119}$, $R^{1110}$, $R^{1111}$, $R^{1112}$, $R^{1113}$, $R^{1114}$, $R^{1115}$, $R^{1116}$, $R^{1117}$ and $R^{1118}$ independently of each other, are selected from hydrogen, halogen, cyano, hydroxyl, mercapto, nitro, —$NE^{111}E^{112}$, —$NR^{Ar111}COR^{Ar112}$, —$CONR^{Ar111}R^{Ar112}$, —$SO_2NR^{Ar111}R^{Ar112}$, —$COOR^{Ar111}$, —$SO_3R^{Ar112}$,
in each case unsubstituted or substituted $C_1$-$C_{30}$-alkyl, polyalkyleneoxy, $C_1$-$C_{30}$-alkoxy, $C_1$-$C_{30}$-alkylthio, $C_3$-$C_{20}$-cycloalkyl, $C_3$-$C_{20}$-cycloalkoxy, $C_6$-$C_{24}$-aryl, $C_6$-$C_{24}$-aryloxy and $C_6$-$C_{24}$-arylthio,
where $R^{113}$ and $R^{114}$, $R^{114}$ and $R^{115}$, $R^{115}$ and $R^{116}$, $R^{116}$ and $R^{117}$, $R^{117}$ and $R^{118}$, $R^{118}$ and $R^{119}$, $R^{119}$ and $R^{1110}$, $R^{1111}$ and $R^{1112}$, $R^{1112}$ and $R^{1113}$, $R^{1113}$ and $R^{1114}$, $R^{1114}$ and $R^{1115}$, $R^{1115}$ and $R^{1116}$, $R^{1116}$ and $R^{1117}$ and/or $R^{1117}$ and $R^{1118}$ together with the carbon atoms of the biphenylyl moiety to which they are bonded, may also form a further fused aromatic or non-aromatic ring system wherein the fused ring system is unsubstituted or substituted; where
$E^{111}$ and $E^{112}$, independently of each other, are hydrogen, unsubstituted or substituted $C_1$-$C_{18}$-alkyl, unsubstituted or substituted $C_2$-$C_{18}$-alkenyl, unsubstituted or substituted $C_2$-$C_{18}$-alkynyl, unsubstituted or substituted $C_3$-$C_{20}$-cycloalkyl or unsubstituted or substituted $C_6$-$C_{10}$-aryl;
$R^{Ar111}$ and $R^{Ar112}$, each independently of each, are hydrogen, unsubstituted or substituted $C_1$-$C_{18}$-alkyl, unsubstituted or substituted $C_3$-$C_{20}$-cycloalkyl, unsubstituted or substituted heterocyclyl, unsubstituted or substituted $C_6$-$C_{20}$-aryl or unsubstituted or substituted heteroaryl;
and mixtures thereof.

Fluorescent dyes of the formula (II) are known from WO 2015/019270. With regard to the use in the color converter of the present invention, the compound (II) is preferably selected from a compound of formula (II-A)

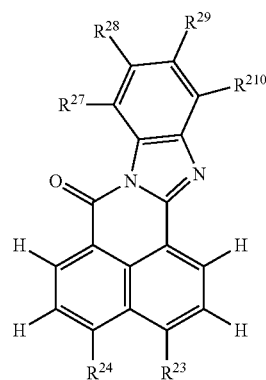
(II-A)

and mixtures comprising at least two different compounds of formula (II-A), in which $R^{23}$ and $R^{24}$ are each independently cyano, phenyl, 4-cyanophenyl or phenyl which carries 1, 2 or 3 substituents selected from $C_1$-$C_{10}$-alkyl, especially cyano, phenyl or 4-cyanophenyl; and $R^{27}$, $R^{28}$, $R^{29}$ and $R^{210}$ are each independently hydrogen, cyano, phenyl, 4-cyanophenyl or phenyl which carries 1, 2 or 3 substituents selected from $C_1$-$C_{10}$-alkyl, especially hydrogen, cyano, phenyl or 4-cyanophenyl.

More preferred are the compounds specified in WO 2015/019270 on page 16, 2$^{nd}$ paragraph to page 20, 3$^{rd}$ paragraph.

With regard to the use in the color converter of the present invention, especially preferred are compounds of formula (II) selected from compounds of the formulae (II-1), (II-2), (II-3), (II-4), (II-5), (II-6), (II-7), (II-8), (II-9), (II-10), (II-11), (II-12), (II-13), (II-14), (II-15), (II-16), (II-17), (II-18), (II-19), (II-20), (II-21), (II-22), (II-23), (II-24), (II-25), (II-26), (II-27), (II-28), (II-29), (II-30), (II-31), (II-32), (II-33), (II-34), (II-35), (II-36), (II-37), (II-38), (II-39), (II-40), (II-41), (II-42), (II-43), (II-44), (II-45), (II-46), (II-47), (II-48), (II-49), and (II-50) and mixtures thereof

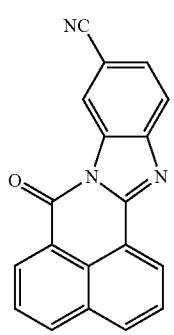
(II-1)

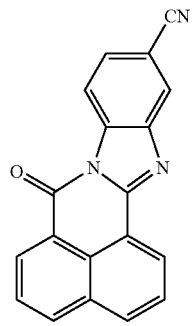
(II-2)

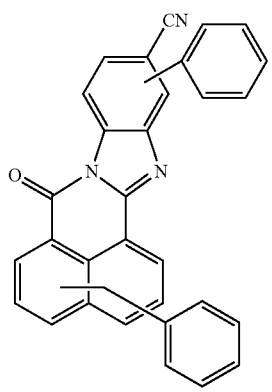
(II-3)

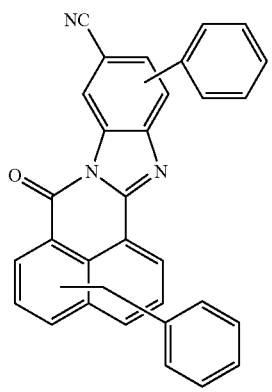
(II-4)

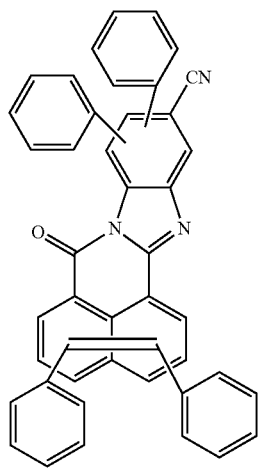
(II-5)

(II-6)
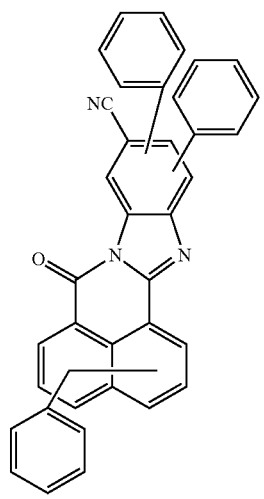
(II-7)
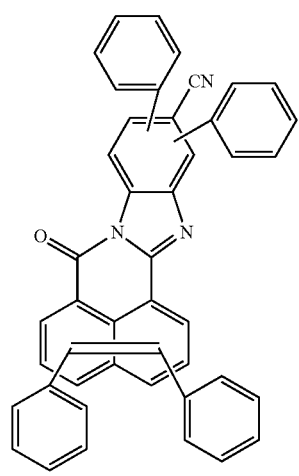
(II-8)
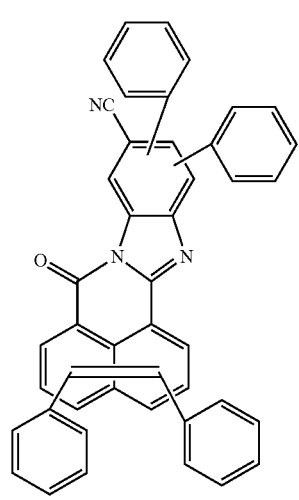
(II-9)
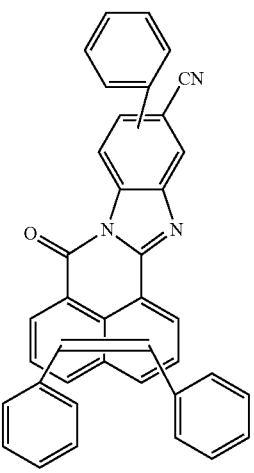
(II-10)
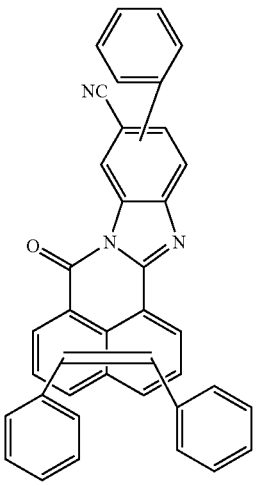
(II-11)
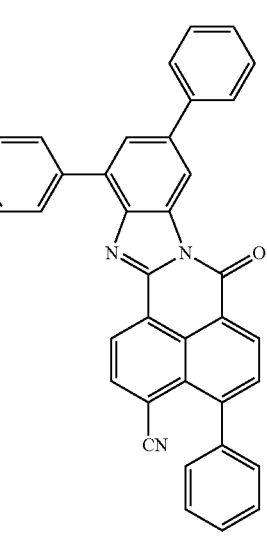

-continued
(II-12)
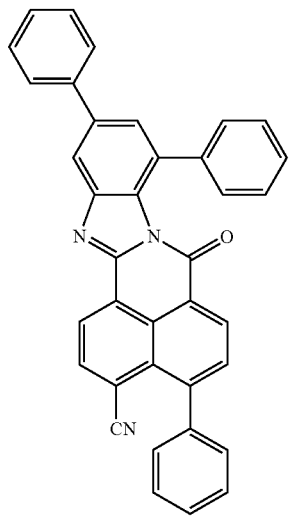
(II-13)
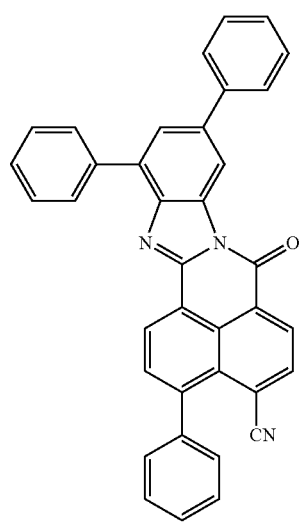
(II-14)
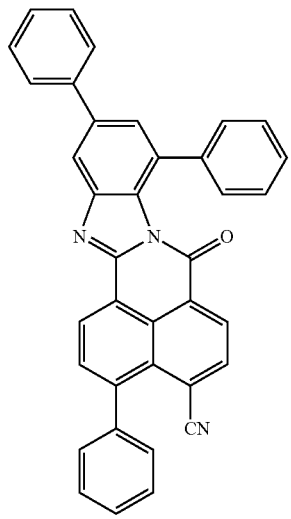
(II-15)
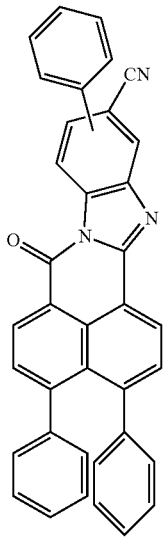
(II-16)
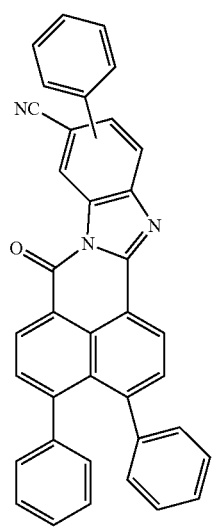
(II-17)
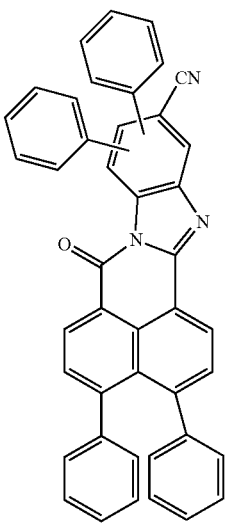

(II-18)
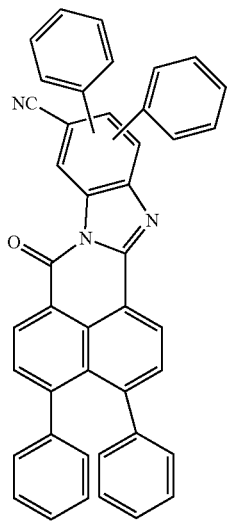
(II-19)
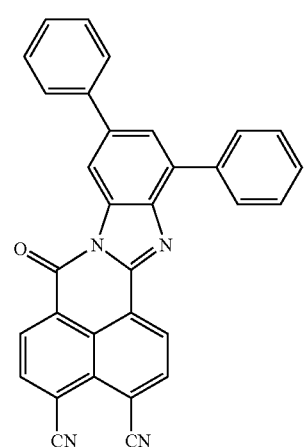
(II-20)
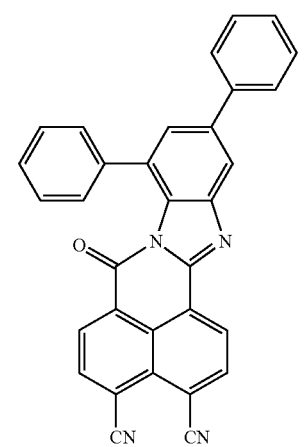
(II-21)
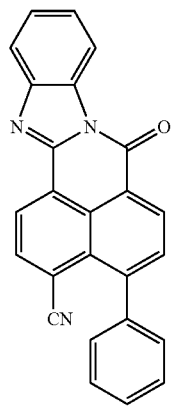
(II-22)
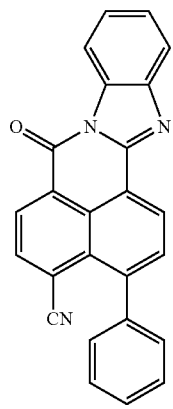
(II-23)
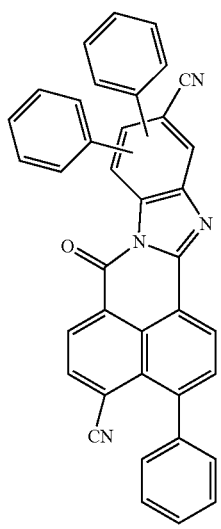

(II-24)
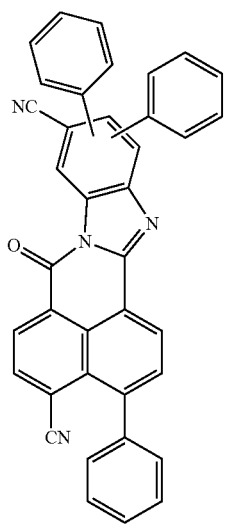
(II-25)
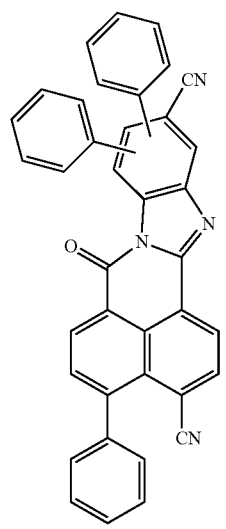
(II-26)
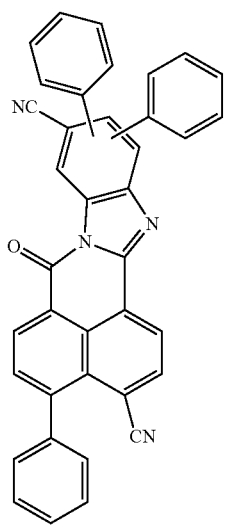
(II-27)
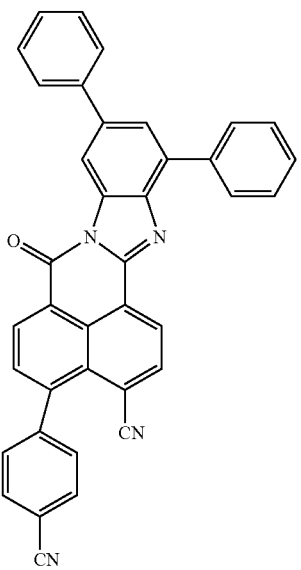
(II-28)
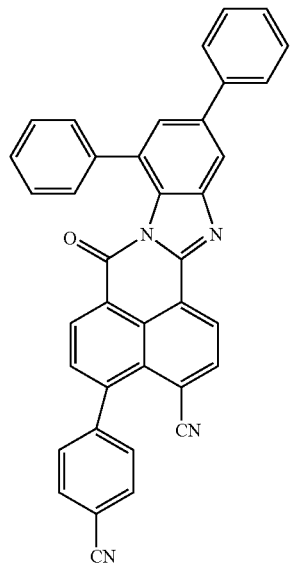

-continued
(II-29)
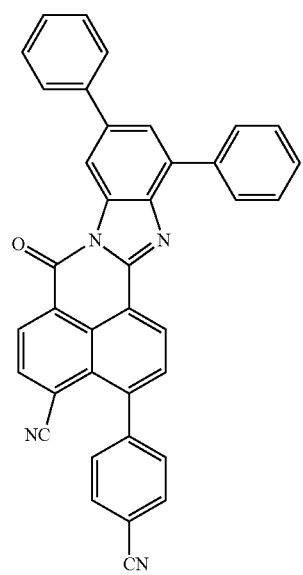
(II-30)
(II-31)
(II-32)
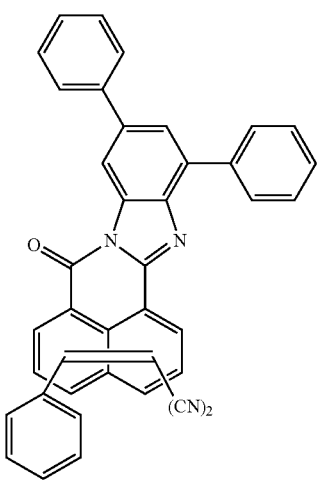
(II-33)
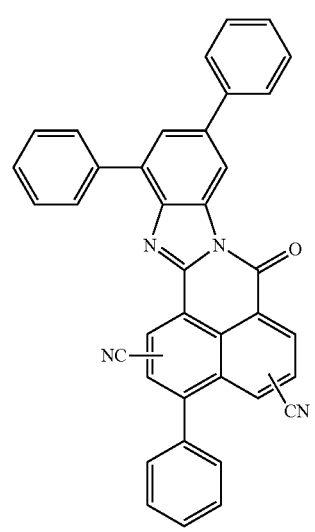
(II-34)
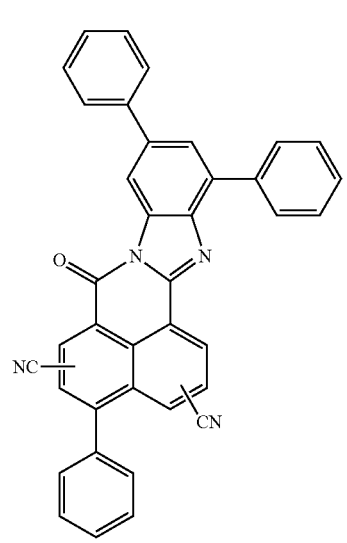

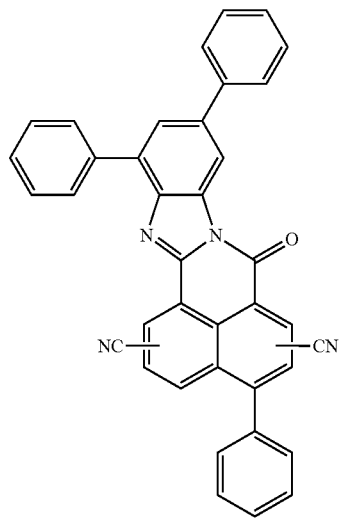
(II-35)
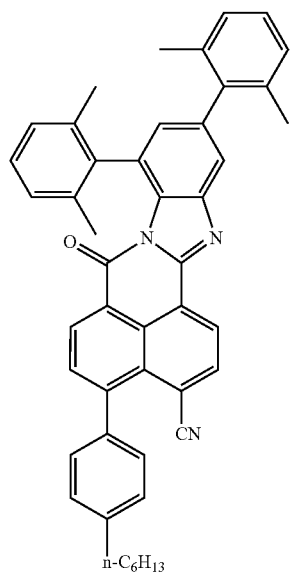
(II-38)
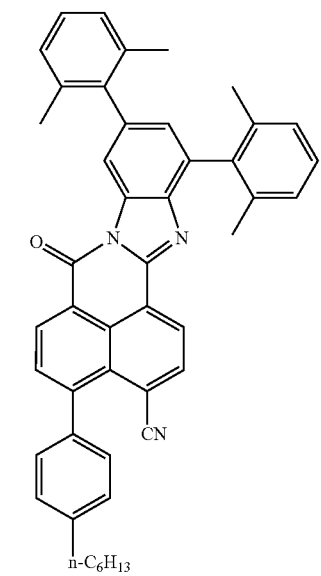
(II-36)
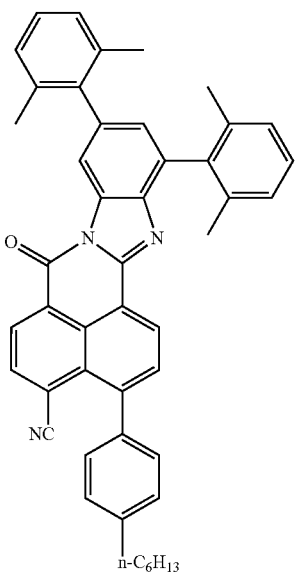
(II-39)
(II-37)

-continued (II-40)

(II-41)

(II-42)

(II-43)

(II-44)

(II-45)

(II-46)
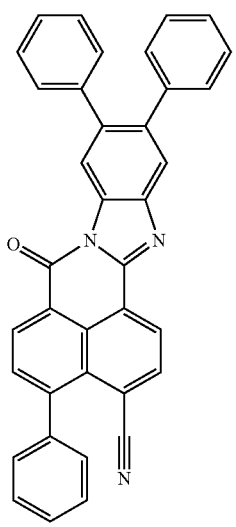
(II-47)
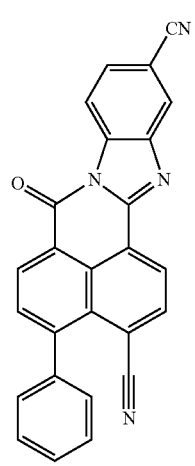
(II-48)
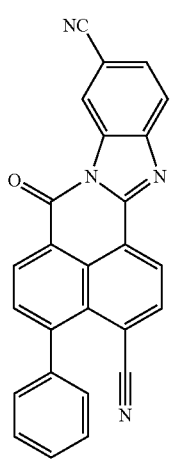
(II-49)
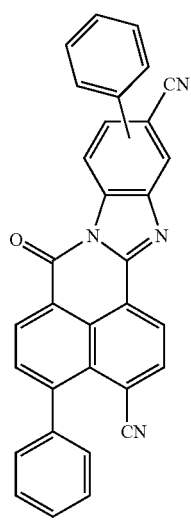
(II-50)
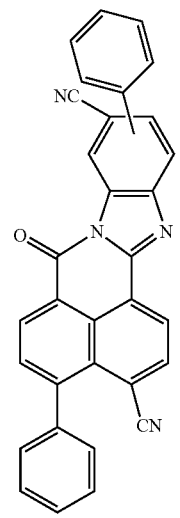
Compounds of the formula (II) are usually green, yellow-green or yellow fluorescent dyes.
Compounds of formula (III) are known from WO 2015/169935. With regard to the use in the color converter of the present invention, the compound of formula (III) encompasses the following compounds of the formulae (III-a) and (III-b) as well as compounds of formulae (III-c) and (IIII-d):
(III-a)
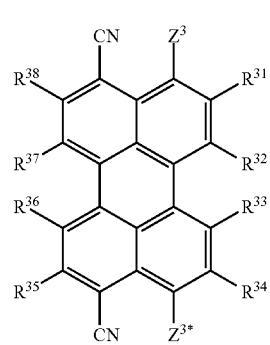

(III-b)

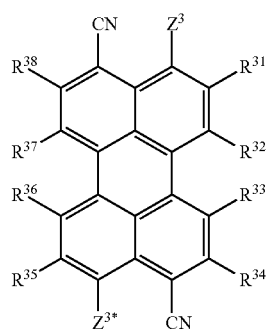

(III-c)

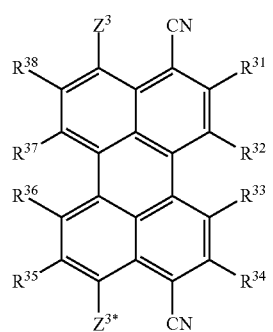

(III-d)

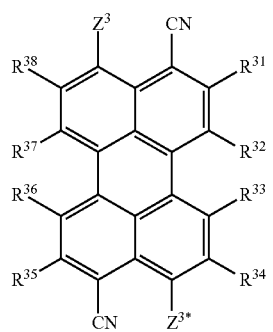

individually and mixtures thereof,
in which $R^{31}$, $R^{32}$, $R^{33}$, $R^{34}$, $R^{35}$, $R^{36}$, $R^{37}$, $R^{38}$, $Z^3$ and $Z^{3*}$ are each as defined above.

In particular, preference is given to the compounds specified in WO 2015/169935 on page 12, line 9 to page 13, line 31. With regard to the use in the color converter of the present invention, preferred are compounds of formula (III) selected from compounds of the formulae (III-1), (III-2), (III-3), (III-4), (III-5), (III-6), (III-7), (III-8), (III-9), (III-10), (III-11), (III-12), (III-13), (III-14), (III-15), (III-16), (III-17), (III-18), (III-19), (III-20)

(III-1)

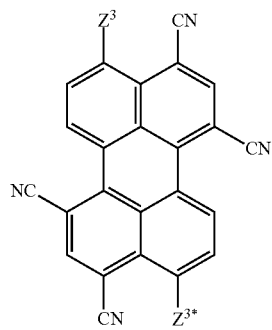

(III-2)

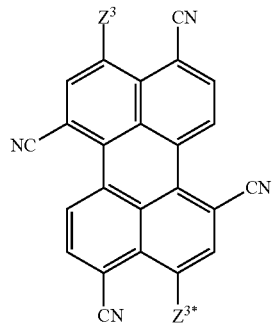

(III-3)

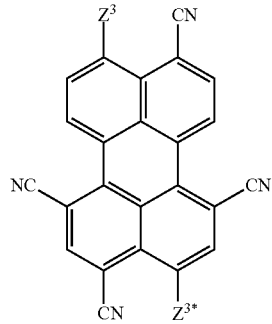

(III-4)

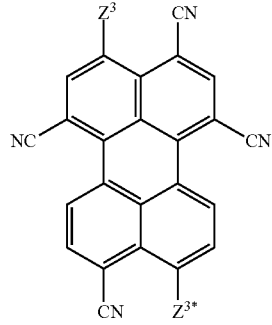

(III-5)

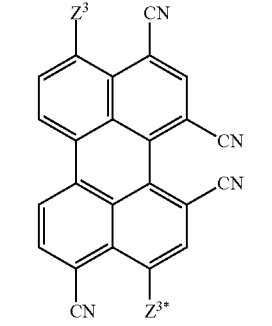

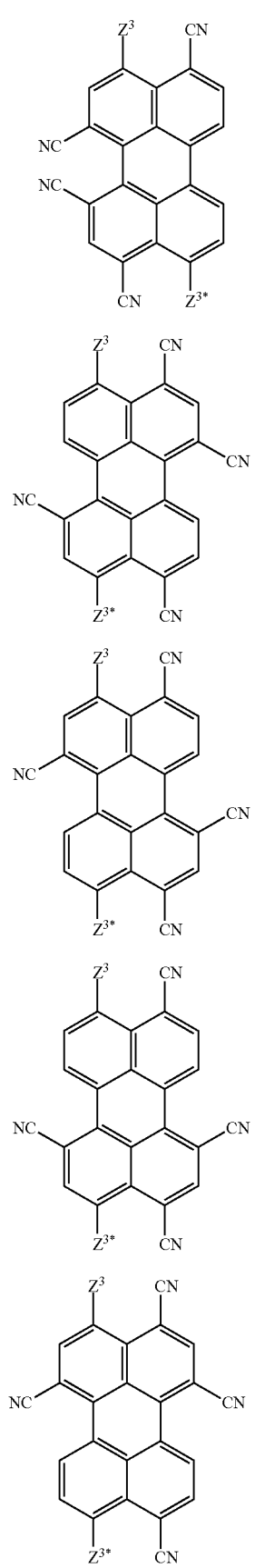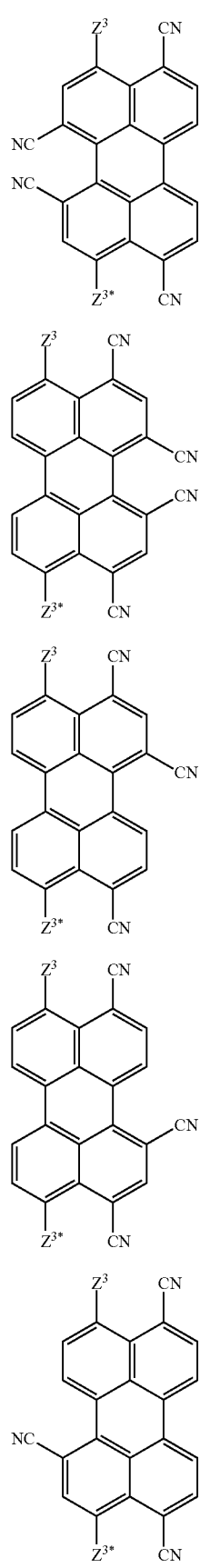

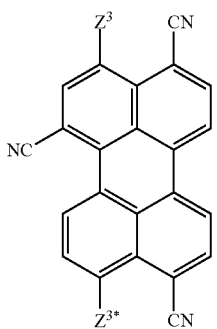
(III-16)

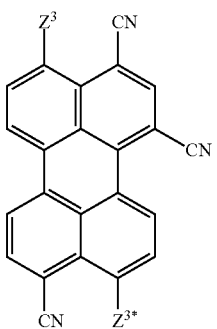
(III-17)

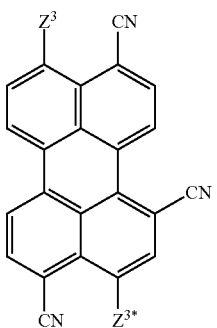
(III-18)

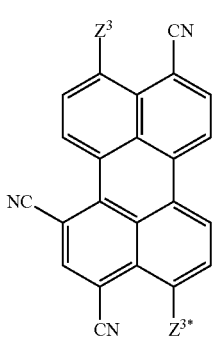
(III-19)

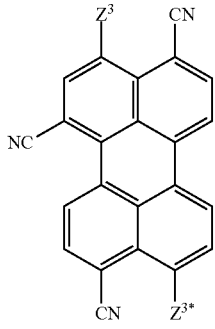
(III-20)

and mixtures thereof,
in which
$Z^3$ is selected from $C_1$-$C_6$-alkyl, $C_1$-$C_6$-alkoxycarbonyl, phenyl, and phenyl bearing 1, 2 or 3 $C_1$-$C_4$-alkyl groups; and
$Z^{3*}$ is selected from $C_1$-$C_6$-alkyl, $C_1$-$C_6$-alkoxycarbonyl, phenyl, and phenyl bearing 1, 2 or 3 $C_1$-$C_4$-alkyl groups.

Among these, specific preference is given to perylene compounds of the formulae (III-1), (III-2), (III-3), (III-4), (III-5), (III-6), (III-7), (III-8), (III-9), (III-10), (III-11), (III-12), (III-13), (III-14), (III-15), (III-16), (III-17), (III-18), (III-19), (III-20) in which Z and Z* have the same definition.

Compounds of the formula (III) are usually yellow or yellow-green fluorescent dyes.

Cyanated compounds of the formula (IV) are subject-matter of WO 2016/151068. With regard to the use in the color converter of the present invention, the compound of formula (IV) is preferably a compound, wherein $X^{40}$ is O. Also preferred are compounds of the formula (IV), wherein $X^{40}$ is S. Preference is given to the compounds specified in WO 2016/151068 on page 24, line 10 to page 34, line 4.

Among these, compounds of the formula (IV) are especially preferred, wherein A is a radical of the formula (A.2). Compounds of the formula (IV), where A is a radical of the formula (A.2) are also referred to as compounds of formula (IV-A.2),

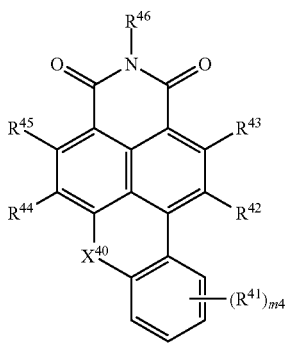
(IV-A.2)

wherein
m4, $X^{40}$, $R^{41}$, $R^{42}$, $R^{43}$, $R^{44}$, $R^{45}$ and $R^{46}$ are as defined above. In particular, m4, $X^{40}$, $R^{41}$, $R^{42}$, $R^{43}$, $R^{44}$ and $R^{45}$ have one of the preferred meanings mentioned above.

In the compounds of the formula (I-A.2), $R^{46}$ is preferably selected from hydrogen, linear $C_1$-$C_{24}$-alkyl, branched $C_3$-$C_{24}$-alkyl, $C_6$-$C_{10}$-aryl and $C_6$-$C_{10}$-aryl-$C_1$-$C_{10}$-alkylene, where the aryl ring in the two last mentioned moieties is unsubstituted or substituted with 1, 2, 3, 4 or 5 identical or different radicals $R^{46a}$. Especially, $R^{46}$ is selected from linear $C_1$-$C_{24}$-alkyl, a radical of the formula (B.1) and a radical of the formula (B.2)

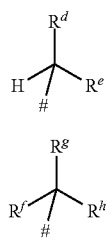

in which
# is the bonding site to the nitrogen atom;
$R^d$ and $R^e$, in the formula (B.1), independently from each other are selected from $C_1$-$C_{23}$-alkyl, where the sum of the carbon atoms of the $R^d$ and $R^e$ radicals is an integer from 2 to 23;
$R^f$, $R^g$ and $R^h$, in the formula (B.2) are independently selected from $C_1$- to $C_{20}$-alkyl, where the sum of the carbon atoms of the $R^f$, $R^g$ and $R^h$ radicals is an integer from 3 to 23.

Preferred radicals of the formula (B.1) are: 1-methylethyl, 1-methylpropyl, 1-methylbutyl, 1-methylpentyl, 1-methylhexyl, 1-methylheptyl, 1-methyloctyl, 1-ethylpropyl, 1-ethylbutyl, 1-ethylpentyl, 1-ethylhexyl, 1-ethylheptyl, 1-ethyloctyl, 1-propylbutyl, 1-propylpentyl, 1-propylhexyl, 1-propylheptyl, 1-propyloctyl, 1-butylpentyl, 1-butylhexyl, 1-butylheptyl, 1-butyloctyl, 1-pentylhexyl, 1-pentylheptyl, 1-pentyloctyl, 1-hexylheptyl, 1-hexyloctyl, 1-heptyloctyl.

A particularly preferred radical of the formula (B.2) is tert.-butyl.

Likewise especially, $R^{46}$ is a radical of the formula (C.1), a radical of the formula (C.2) or a radical of the formula (C.3)

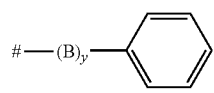

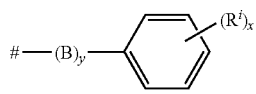

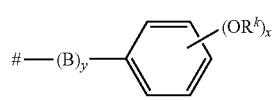

where
# represents the bonding side to the nitrogen atom, B where present, is a $C_1$-$C_{10}$-alkylene group which may be interrupted by one or more nonadjacent groups selected from —O— and —S—,
y is 0 or 1,
$R^i$ is independently of one another selected from $C_1$-$C_{24}$-alkyl, $C_1$-$C_{24}$-fluoroalkyl, fluorine, chlorine or bromine,
$R^k$ is independently of one another selected from $C_1$-$C_{24}$-alkyl,
x in formulae C.2 and C.3 is 1, 2, 3, 4 or 5.

Preferably, y is 0, i.e. the variable B is absent.

Irrespectively of its occurrence, $R^i$ is preferably selected from $C_1$-$C_{24}$-alkyl, more preferably linear $C_1$-$C_{10}$-alkyl or branched $C_3$-$C_{10}$-alkyl, especially isopropyl. Irrespectively of its occurrence, $R^k$ is preferably selected from $C_1$-$C_{30}$-alkyl, more preferably linear $C_1$-$C_{10}$-alkyl or branched $C_3$-$C_{10}$-alkyl. The variable x in formulae C.2 and C.3 is preferably 1, 2 or 3.

A special group of embodiments relates to compounds of formula (IV-A.2), wherein the variables m4, $X^{40}$, $R^{41}$, $R^{42}$, $R^{43}$, $R^{44}$, and $R^{45}$ independently of each other or in particular in combination, have the following meanings:

$X^{40}$ is O or S;

$R^{42}$ and $R^{44}$ are each cyano;

$R^{43}$ and $R^{45}$ are each hydrogen or one of $R^{43}$ and $R^{45}$ is bromine and the other of $R^{43}$ and $R^{45}$ is hydrogen;

$R^{41}$ is selected from cyano, bromine, and phenyl which is unsubstituted or carries 1 or 2 radicals selected from $C_1$-$C_4$-alkyl;

$R^{46}$ is selected from hydrogen, $C_1$-$C_{24}$-linear alkyl, branched $C_3$-$C_{24}$-alkyl, a radical of the formula (C.1), a radical of the formula (C.2) and a radical of the formula (C.3); m4 is 0 or 1.

Even more preferably, $X^{40}$ is O or S;

$R^{42}$ and $R^{44}$ are each cyano;

$R^{43}$ and $R^{45}$ are each hydrogen;

$R^{41}$ is selected from cyano, bromine, and phenyl which is unsubstituted or carries 1 or 2 radicals selected from $C_1$-$C_4$-alkyl; especially cyano;

$R^{46}$ is selected from linear $C_1$-$C_{24}$-alkyl, branched $C_3$-$C_{24}$-alkyl, a radical of the formula (C.1), a radical of the formula (C.2) and a radical of the formula (C.3); especially linear $C_1$-$C_{24}$-alkyl, branched $C_3$-$C_{24}$-alkyl, or phenyl which carries 1 or 2 radicals selected from $C_1$-$C_4$-alkyl such as 2,6-diisopropylphenyl;

m4 is 0 or 1.

Examples for preferred compounds of formula (IV-A.2) are shown below:

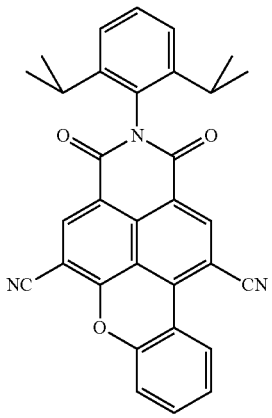

(I-A.2-1)

-continued
(I-A.2-2)
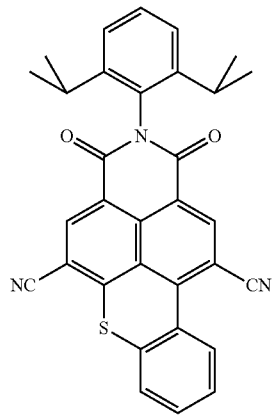
(I-A.2-3)
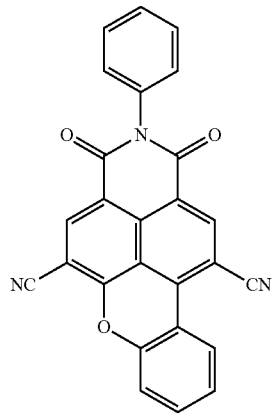
(I-A.2-4)
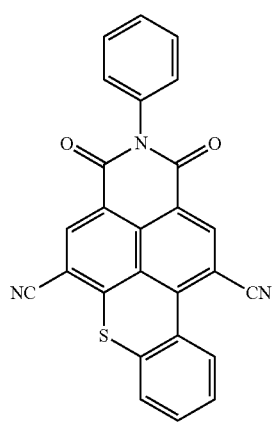
(I-A.2-5)
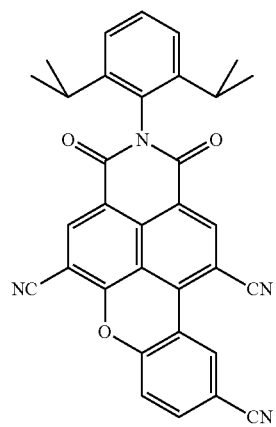
(I-A.2-6)
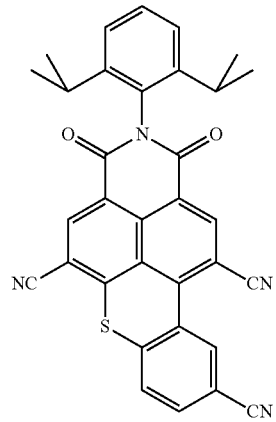
(I-A.2-7)
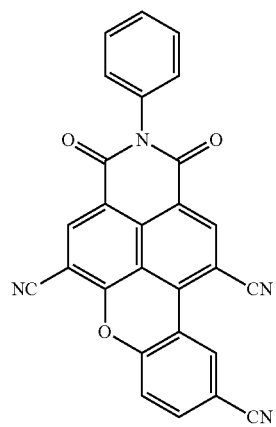

(I-A.2-8)
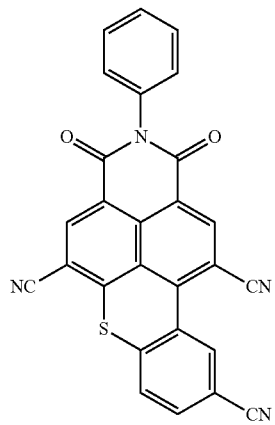
(IV-A.2-9)
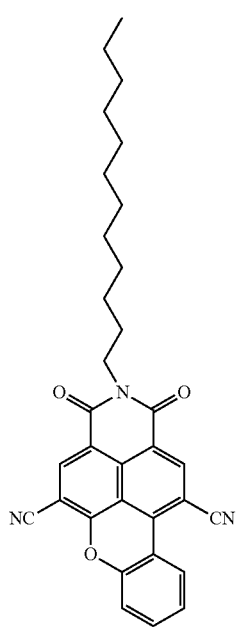
(IV-A.2-10)
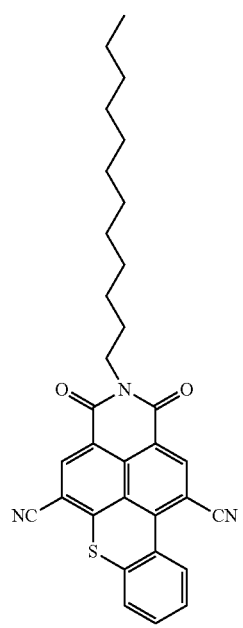
(IV-A.2-11)
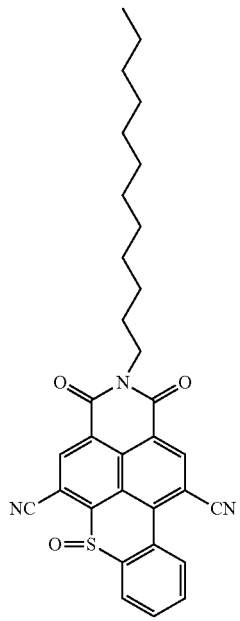
(IV-A.2-12)
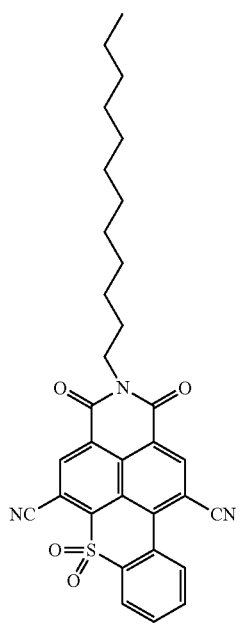

(IV-A.2-13)

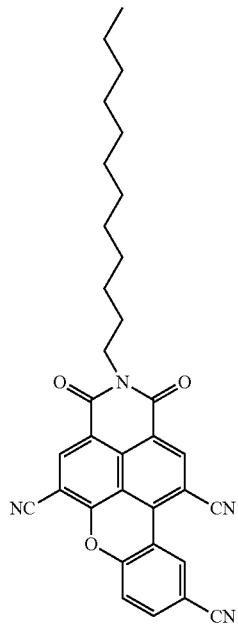

(IV-A.2-14)

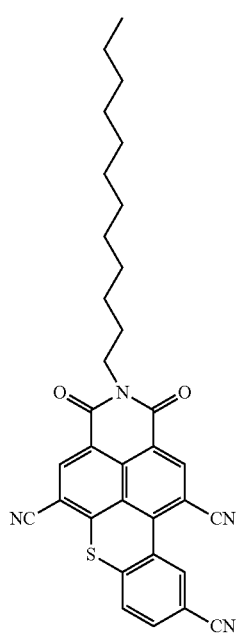

(IV-A.2-15)

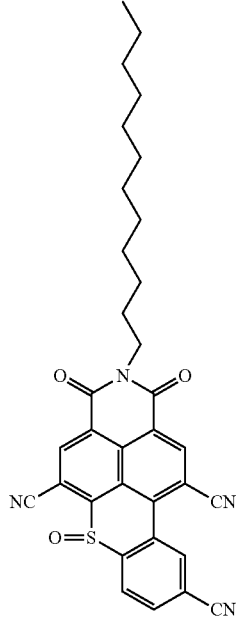

(IV-A.2-16)

Benzoxanthene compounds of the formula (V) are known from WO 2014/131628. They are usually yellow or yellow-green fluorescent dyes.

Compounds having a structural unit of the formula (VI) are known from WO 2012/168395. With regard to the use in the color converter of the present invention, the compound having a structural unit of formula (VI) is preferably a compound as specified in WO 2012/168395, at page 28, line 14 to page 32, line 5.

With regard to the use in the color converter of the present invention, the compound having a structural unit of formula (VI) is more preferably selected from compounds of formulae (VI-1), (VI-2), (VI-3), (VI-4), (VI-5), (VI-6), (VI-7), (VI-8), (VI-9), (VI-20), (VI-21), (VI-22), (VI-23), (VI-24), (VI-25), (VI-26), (VI-27), (VI-28), (VI-29), (VI-30), (VI-31), (VI-32), (VI-33), (VI-34), (VI-35), (VI-36), (VI-37), (VI-38), (VI-39), (VI-40), (VI-41), (VI-42), (VI-43), (VI-44), (VI-45), (VI-46), (VI-47), (VI-48), (VI-49), (VI-50), (VI-51), (VI-52), (VI-53), (VI-54), (VI-55), and mixtures thereof
-continued
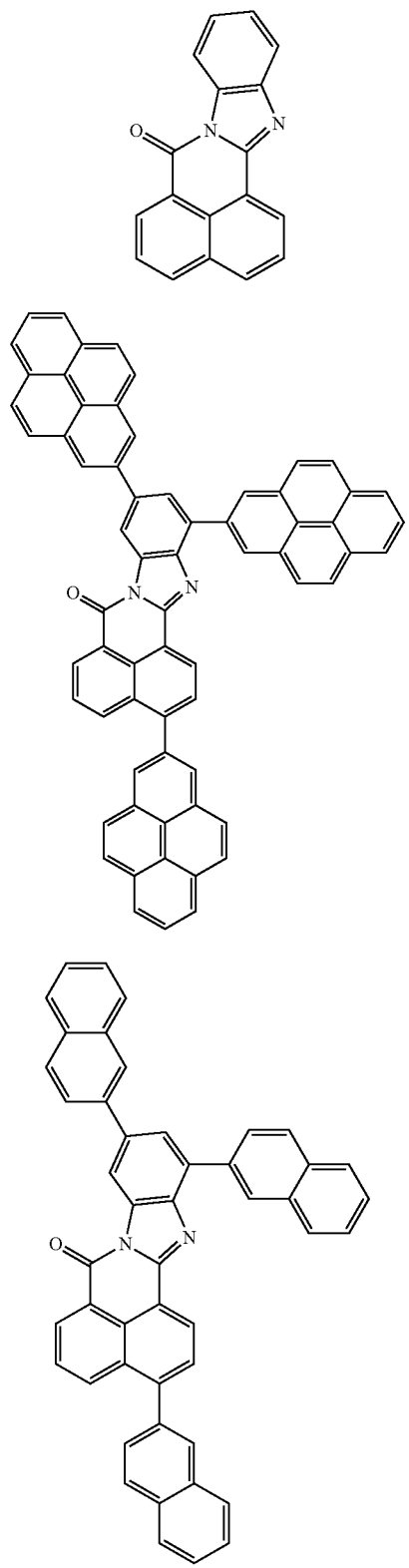
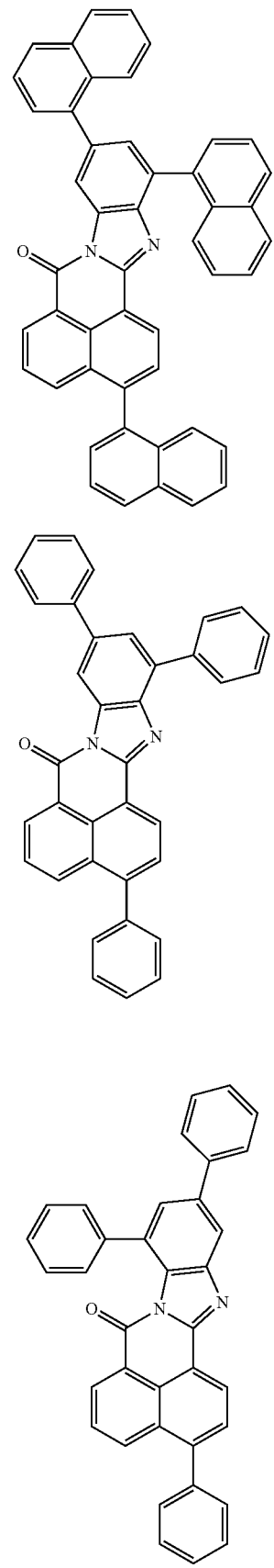

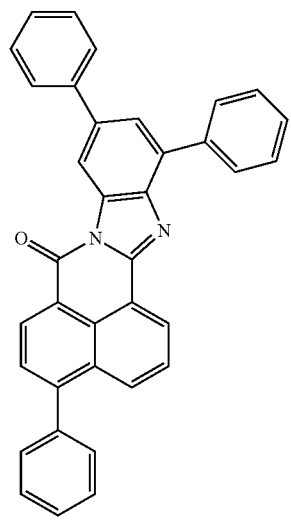 (VI-7)
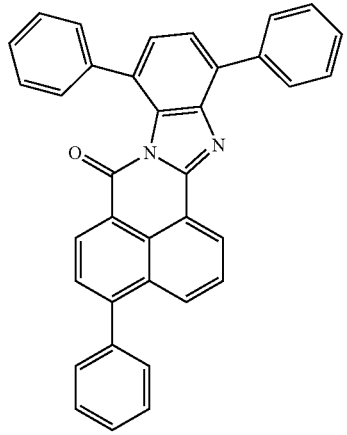 (VI-10)
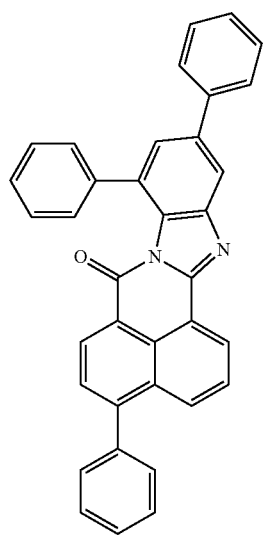 (VI-8)
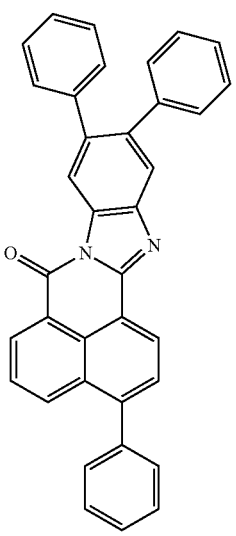 (VI-11)
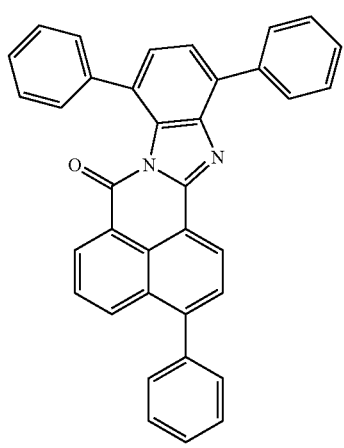 (VI-9)
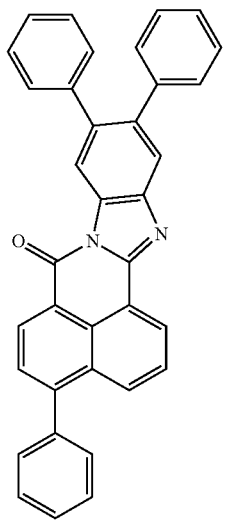 (VI-12)

(VI-13)
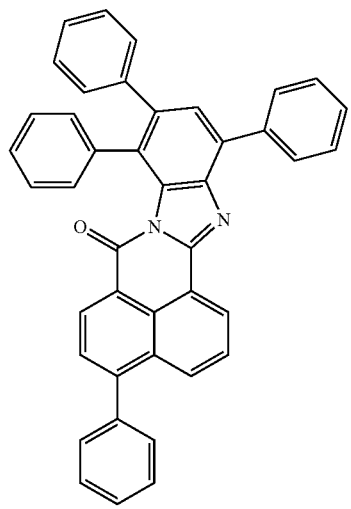
(VI-14)
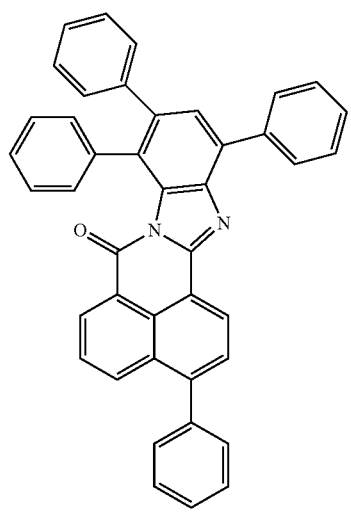
(VI-15)
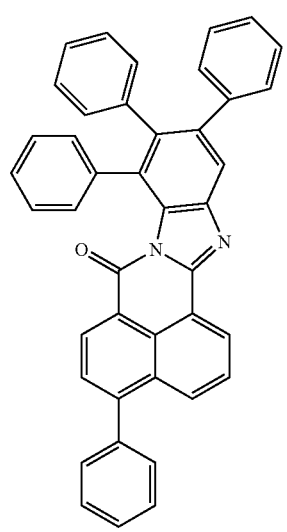
(VI-16)
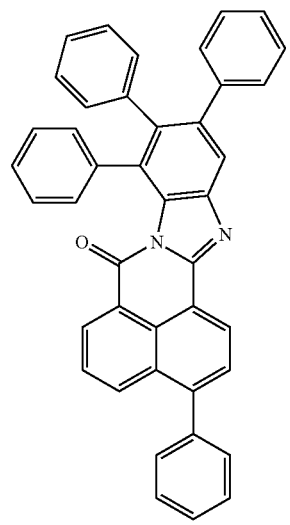
(VI-17)
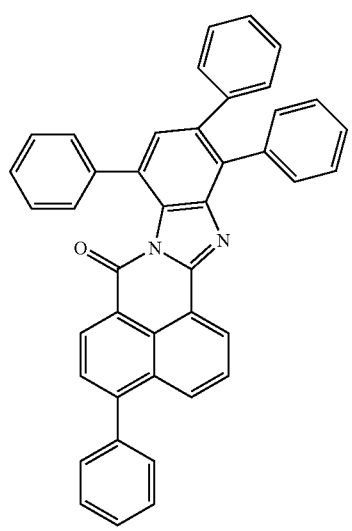
(VI-18)
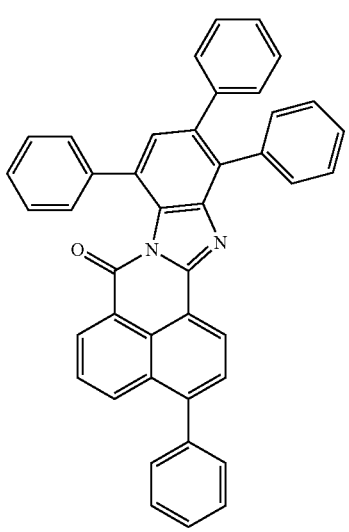

(VI-19)
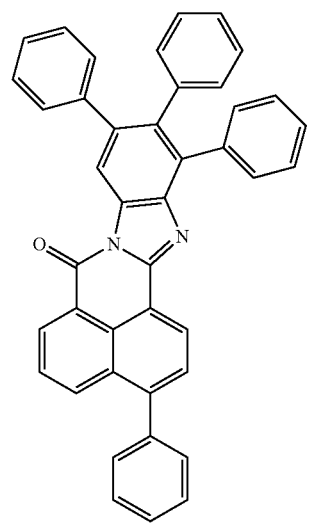
(VI-20)
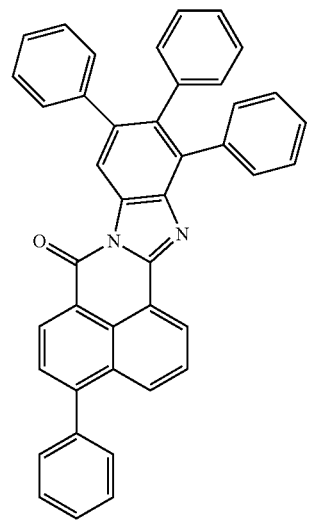
(VI-21)
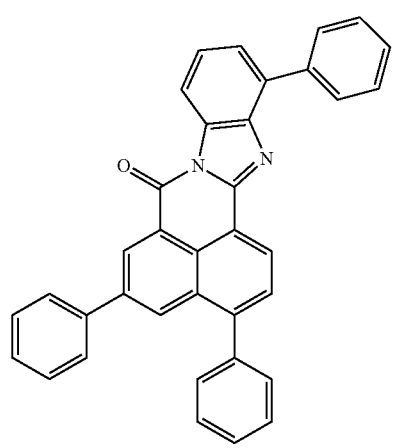
(VI-22)
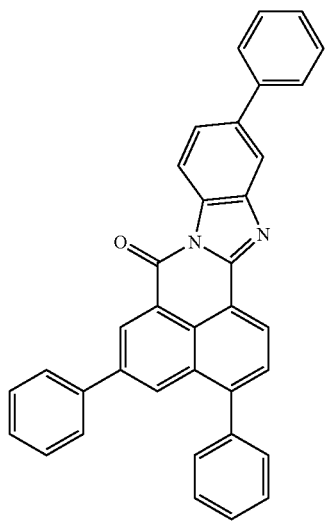
(VI-23)
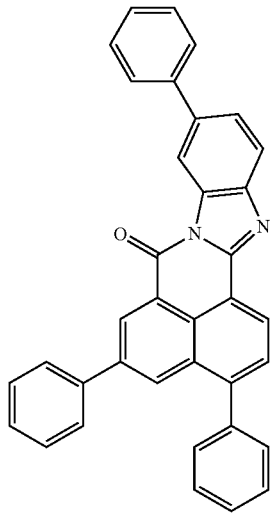
(VI-24)
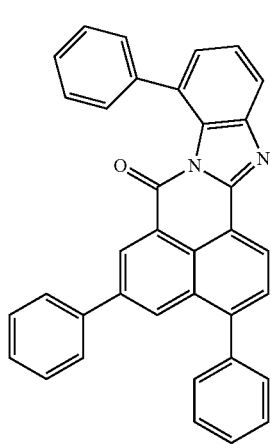

(VI-25)
(VI-26)
(VI-27)
(VI-28)
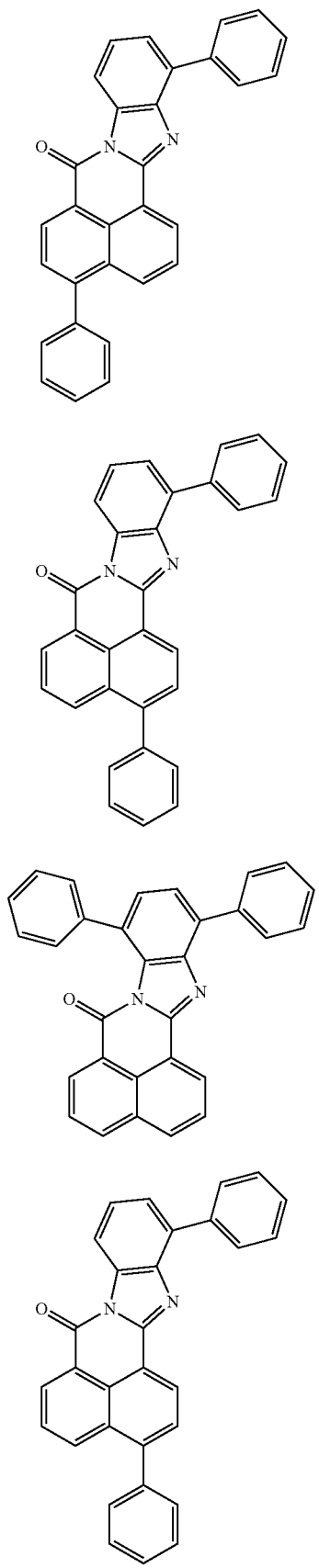
(VI-29)
(VI-30)
(VI-31)
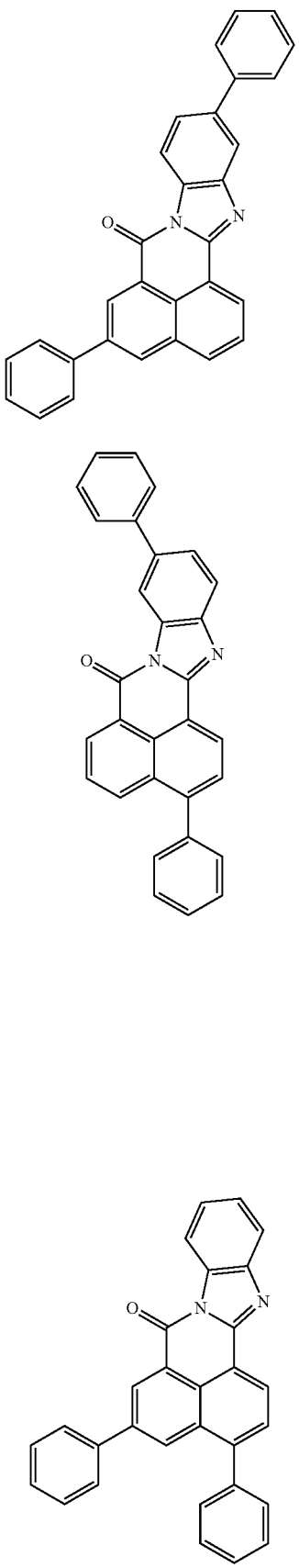

(VI-32)
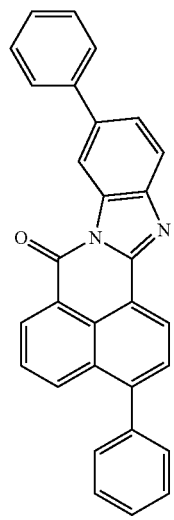
(VI-33)
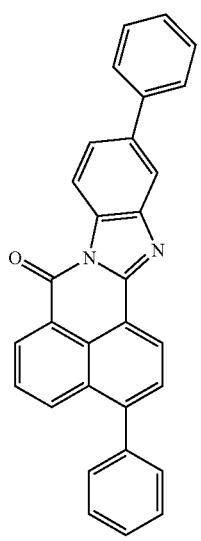
(VI-34)
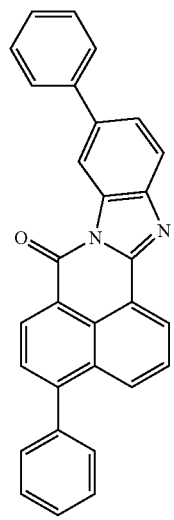
(VI-35)
(VI-36)
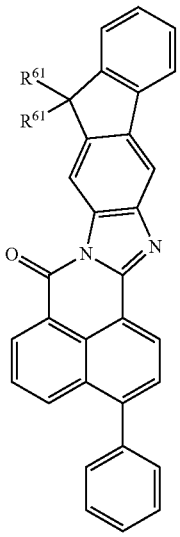
(VI-37)
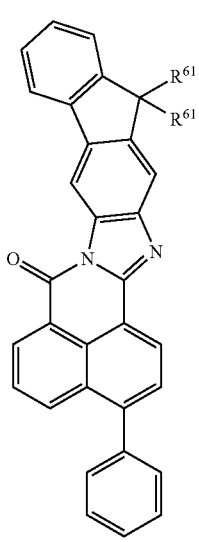

(VI-38)
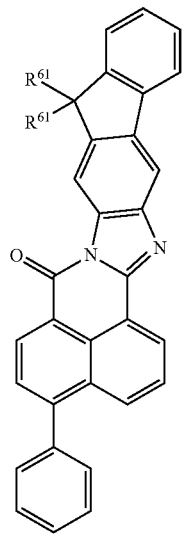
(VI-39)
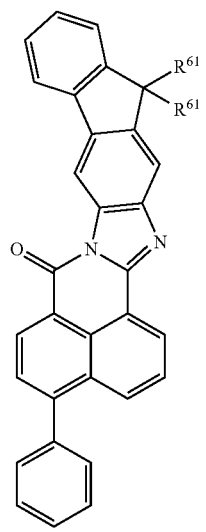
(VI-40)
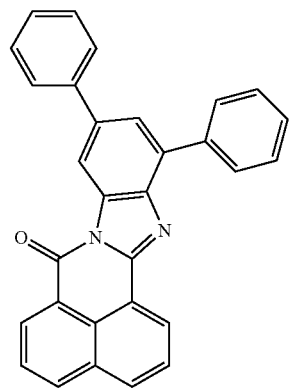
(VI-41)
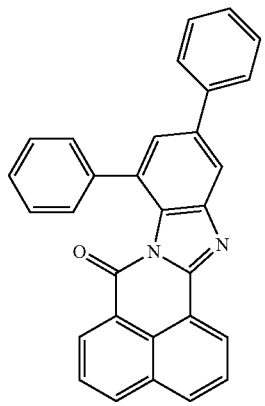
(VI-42)
(VI-43)
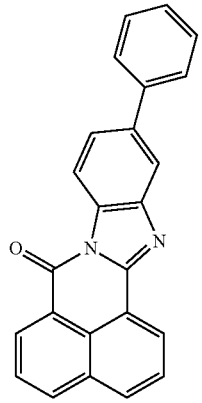
(VI-44)
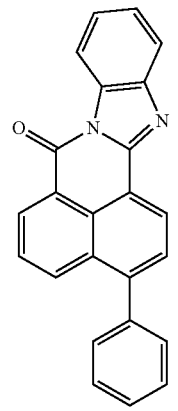

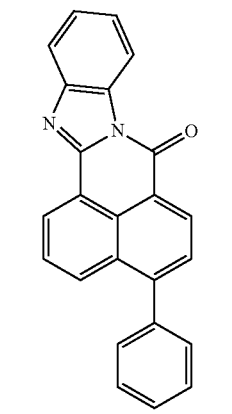
(VI-45)
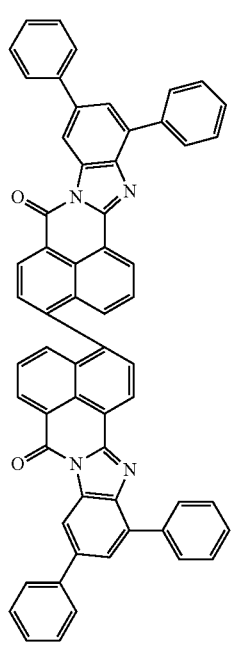
(VI-46)
(VI-47)
(VI-48)
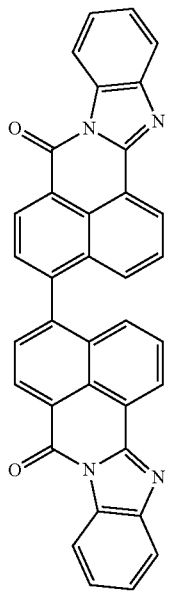
(VI-49)

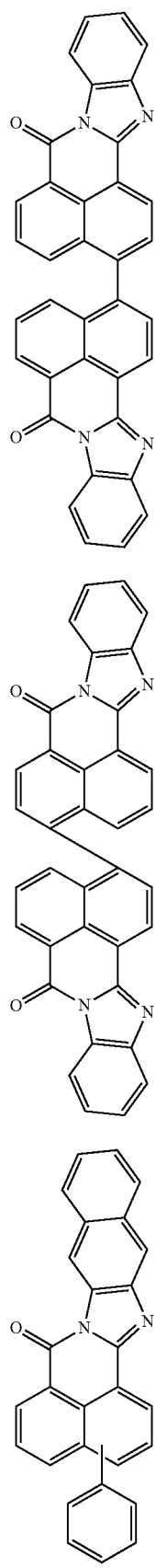
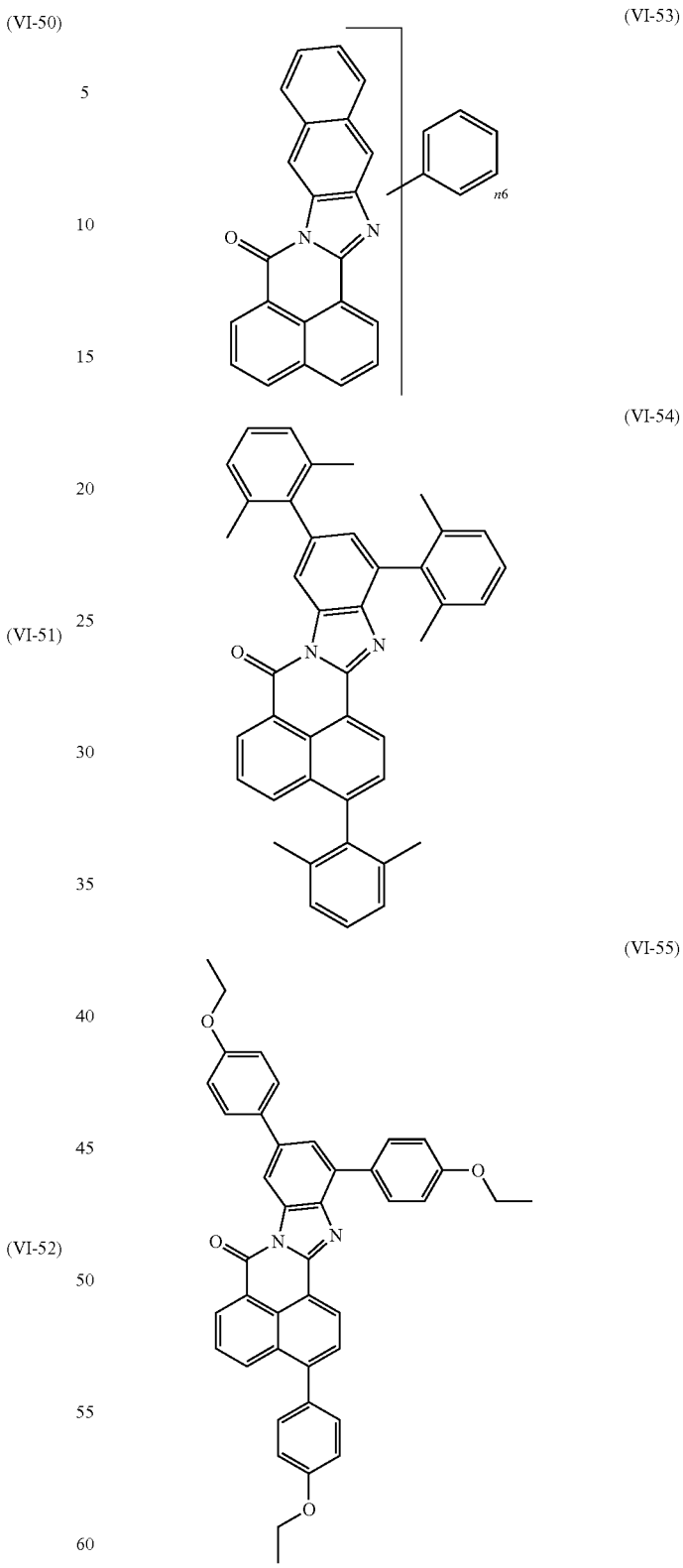
and mixtures thereof,
where n6 is a number from 0, 1, 2, 3, 4, 5, 6, 7, 8, 9 or 10;
$R^{61}$ is independently hydrogen, $C_1$-$C_{18}$-alkyl or cycloalkyl, the carbon chain of which may comprise one or more —O—, —S—, —CO—, —SO— and/or —SO$_2$— moieties and which may be mono- or polysubstituted;

aryl or heteroaryl which may be mono- or polysubstituted.

The use of the inventive red-fluorescent dye of formula (I) in combination with a compound having at least one structural unit of formula (VI) is particularly well suited for color converters. Especially preferred are the compounds of formulae (VI-5), (VI-6), (VI-7) and (VI-8) and mixtures thereof.

Compounds having at least one structural unit of the formula (VI) are usually yellow or yellow-green fluorescent dyes.

With regard to the use in the color converter of the present invention, preference is given to compounds of formula (VII), wherein $R^{71}$ and $R^{72}$ are each independently selected from $C_1$-$C_{10}$-alkyl, 2,6-di($C_1$-$C_{10}$-alkyl)aryl and 2,4-di($C_1$-$C_{10}$-alkyl)aryl. More preferably, $R^{71}$ and $R^{72}$ are identical. Very particularly, $R^{71}$ and $R^{72}$ are each 2,6-diisopropylphenyl or 2,4-di-tert-butylphenyl.

$R^{73}$ is preferably phenoxy, or ($C_1$-$C_{10}$-alkyl)phenoxy, more preferably 2,6-(dialkyl)phenoxy or 2,4-(dialkyl)phenoxy. Especially preferably $R^{73}$ is phenoxy, 2,6-diisopropylphenoxy, 2,4-di-tert-butylphenoxy or 4-tert-octylphenoxy. Preferred compounds of formula (VII) are N,N'-bis(2,6-diisopropylphenyl)-1,7-di(2,6-diisopropyl-phenoxy)perylene-3,4;9,10-tetracarboximide, N,N'-bis(2,6-diisopropylphenyl)-1,7-di(p-tert-octylphenoxy)perylene-3,4;9,10-tetracarboximide and N,N'-bis(2,6-diisopropylphenyl)-1,7-diphenoxyperylene-3,4;9,10-tetracarboximide.

With regard to the use in the color converter of the present invention, preference is given to compounds of formula (VIII), wherein $R^{81}$ and $R^{82}$ are each independently selected from $C_1$-$C_{10}$-alkyl, 2,6-di($C_1$-$C_{10}$-alkyl)aryl and 2,4-di($C_1$-$C_{10}$-alkyl)aryl. More preferably, $R^{81}$ and $R^{82}$ are identical. Very particularly, $R^{81}$ and $R^{82}$ are each 2,6-diisopropylphenyl or 2,4-di-tert-butylphenyl.

$R^{83}$ is preferably phenoxy, or ($C_1$-$C_{10}$-alkyl)phenoxy, more preferably 2,6-(dialkyl)phenoxy or 2,4-(dialkyl)phenoxy. Especially preferably $R^{83}$ is phenoxy, 2,6-diisopropylphenoxy, 2,4-di-tert-butylphenoxy or 4-tert-octylphenoxy. Preferred embodiments of compounds of formula (VIII) are N,N'-bis(2,6-diisopropylphenyl)-1,6-di(2,6-diisopropylphenoxy)perylene-3,4;9,10-tetracarboximide, N,N'-bis(2,6-diisopropylphenyl)-1,6-di(p-tert-octylphenoxy)perylene-3,4; 9,10-tetracarboximide and N,N'-bis(2,6-diisopropylphenyl)-1,6-diphenoxyperylene-3,4;9,10-tetracarboximide.

With regard to the use in the color converter of the present invention, further suitable examples of compounds of formulae (VII) and (VIII) are the perylene derivatives specified in WO 2007/006717 at page 1, line 5 to page 22, line 6. Fluorescent dyes of formulae (VII) and (VIII) are usually red-fluorescent dyes.

With regard to the use in the color converter of the present invention, preference is given to compounds of formula (IX), where $R^{91}$ and $R^{92}$ are each independently selected from $C_1$-$C_{10}$-alkyl, 2,6-di($C_1$-$C_{10}$-alkyl)aryl and 2,4-di($C_1$-$C_{10}$-alkyl)aryl. More preferably, $R^{91}$ and $R^{92}$ have the same meaning. Very particularly, $R^{91}$ and $R^{92}$ are each 2,6-diisopropylphenyl or 2,4-di-tert-butylphenyl.

With regard to the use in the color converter of the present invention, preference is given to compounds of formula (X), wherein $R^{102}$ is $C_1$-$C_{10}$-alkyl, 2,6-di($C_1$-$C_{10}$-alkyl)-aryl or 2,4-di($C_1$-$C_{10}$-alkyl)aryl, in particular $R^{102}$ is 2,6-diisopropylphenyl or 2,4-di-tert-butylphenyl.

Compounds of the formula (X) are usually yellow-orange fluorescent dyes.

Compounds of the formula (XI) are subject matter of unpublished EP 16151228.0 (post-published WO 2017/121833). With regard to the use in the color converter of the present invention, preference is given to compounds of formula (XI), where $R^{111}$ and $R^{112}$ are, independently of each other, selected from phenyl which is unsubstituted or substituted by 1, 2 or 3 $C_1$-$C_6$-alkyl; and $R^{113}$, $R^{114}$, $R^{115}$, $R^{116}$, $R^{117}$, $R^{118}$, $R^{119}$, $R^{1110}$, $R^{1111}$, $R^{1112}$, $R^{1113}$, $R^{1114}$, $R^{1115}$, $R^{1116}$, $R^{1117}$ and $R^{1118}$ are each hydrogen. The compound of formula (XI) as defined above is preferably

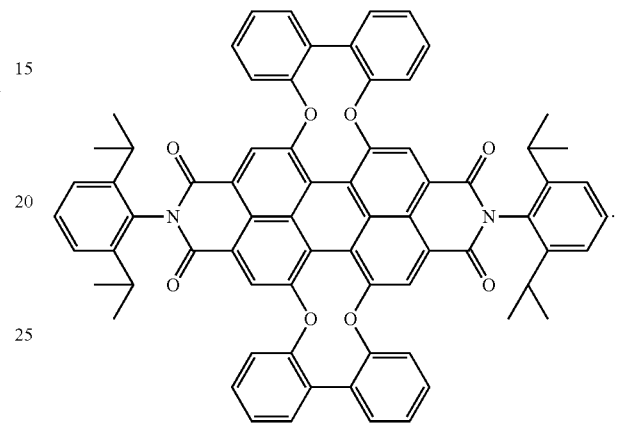

The compound of formula (XI) can be prepared by reacting the appropriate chlorinated or brominated perylene bisimide of formula (XII)

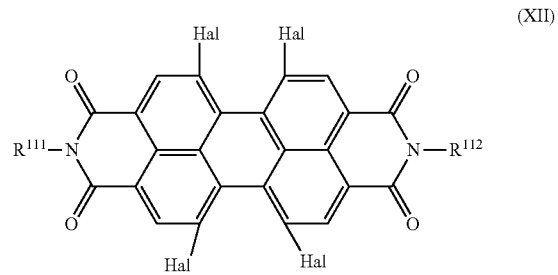

where

Hal is in each case bromine or in each case chlorine; and $R^{111}$ and $R^{112}$ are as defined above;

with a 2,2'-biphenol compound of formula (XIII) and, if appropriate, an 2,2'-biphenol compound of formula (XIV)

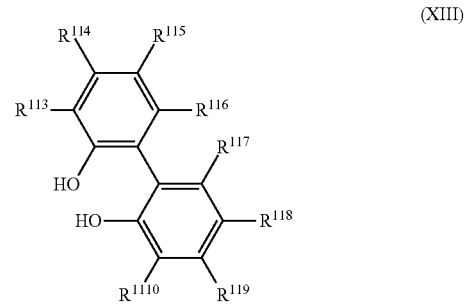

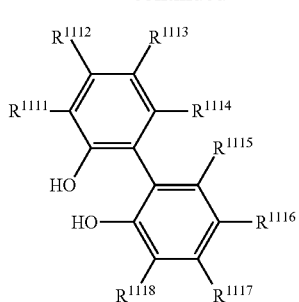

(XIV)

where
$R^{113}, R^{114}, R^{115}, R^{116}, R^{117}, R^{118}, R^{119}, R^{1110}, R^{1111}, R^{1112}, R^{1113}, R^{1114}, R^{1115}, R^{1116}, R^{1117}$ and $R^{1118}$ are as defined above.

The 2,2'-biphenol of formula (XIV) may also be as defined for the 2,2'-biphenol of formula (XIII) (if only one 2,2'-biphenol of the formula (XIII) is used for halogen replacement reaction).

The reaction is usually carried out in the presence of a base. Suitable bases are in particular inorganic alkali metal or alkaline earth metal bases, the alkali metal bases being particularly suitable. Examples of inorganic bases are the carbonates and hydrogencarbonates, hydroxides, hydrides and amides of alkali metals and alkaline earth metals. Preferred bases are the carbonates and hydrogencarbonates, particular preference being given to the carbonates. Preferred alkali metals are lithium, sodium, potassium and cesium; particularly suitable alkaline earth metals are magnesium and calcium. It will be appreciated that it is also possible to use base mixtures. Very particularly preferred bases are lithium carbonate, sodium carbonate, potassium carbonate and cesium carbonate.

The reaction is usually carried out in the presence of a polar, aprotic solvent. Suitable solvents are especially aliphatic carboxamides, preferably N,N-di-$C_1$-$C_4$-alkyl-$C_1$-$C_4$-carboxamides, lactams such as dimethylformamide, diethylformamide, dimethylacetamide, dimethylbutyramide and N-methyl-2-pyrrolidone (NMP), nitriles such as acetonitrile. It is also possible to use mixtures of polar, aprotic solvents. Particular preference is given to NMP.

The reaction temperature is generally within the range from room temperature to the boiling point of the solvent, preferably 40 to 160° C.

Compounds of formula (XII) can be prepared in analogy to the methods described above for compounds of formula (I).

Compounds of formula (XIII) and (XIV) are commercially available or can be prepared according to literature methods.

According to a preferred embodiment, the color converter comprises, in addition to the red-fluorescent dye of formula (I) or a mixture comprising at least two different compounds of formula (I), one further organic fluorescent dye or a mixture comprising at least two different fluorescent dyes from an individual group of further fluorescent dyes (i) to (vii) as defined above.

According to a further preferred embodiment, the color converter comprises, in addition to the at least one red-fluorescent dye of formula (I) or a mixture comprising at least two different compounds of formula (I), two or more further organic fluorescent dyes from different groups of further fluorescent dyes (i) to (vii) as defined above.

Preferably, the color converter comprises at least one compound selected from compounds of formulae (II), (III), (IV), (V), (VII), (VIII), (IX), (X), (XI), compounds comprising at least one structural unit of formula (VI) and mixtures thereof, in order to generate white light having a chromaticity coordinate close at Plank's curve and with a desired CCT and high average color rendering characteristics. Preferably, the color converter comprises 1 or 2 compounds selected from compounds of formulae (II), (III), (IV), (V), (VII), (VIII), (IX), (X), (XI), compounds comprising at least one structural unit of formula (VI) and mixtures thereof.

In a preferred embodiment, the color converter according to the present invention comprises at least one further organic fluorescent dye selected from
compounds of formula (II) and mixtures thereof,
compounds of formula (IV) and mixtures thereof,
compounds comprising at least one structural unit of formula (VI) and mixtures thereof,
compounds of formula (VII),
compounds of formula (VIII),
compounds of formula (XI) and mixtures thereof,
and mixtures thereof.

Amongst these, especially preferred are color converters, comprising a compound of formulae (VI-1), (VI-2), (VI-3), (VI-4), (VI-5), (VI-6), (VI-7), (VI-8), (VI-9), (VI-10), (VI-11), (VI-12), (VI-13), (VI-14), (VI-15), (VI-16), (VI-17), (VI-18), (VI-19), (VI-20), (VI-21), (VI-22), (VI-23), (VI-24), (VI-25), (VI-26), (VI-27), (VI-28), (VI-29), (VI-30), (VI-31), (VI-32), (VI-33), (VI-34), (VI-35), (VI-36), (VI-37), (VI-38), (VI-39), (VI-40), (VI-41), (VI-42), (VI-43), (VI-44), (VI-45), (VI-46), (VI-47), (VI-48), (VI-49), (VI-50), (VI-51), (VI-52), (VI-53), (VI-54), (VI-55) and mixtures thereof as compound comprising at least one structural unit of formula (VI). More especially preferred are color converters comprising a compound of formulae (VI-5), (VI-6), (VI-7), (VI-8) and mixtures thereof as compound comprising at least one structural unit of formula (VI).

According to a special embodiment, the color converter comprises
at least one compound of the formula (I), wherein $R^1$ and $R^2$ have the same meaning and are phenyl which carries 1, 2 or 3 $C_1$-$C_6$-alkyl substituents; $R^3, R^{10}, R^{11}$, and $R^{18}$ have the same meaning and are phenyl, which is unsubstituted or phenyl which is substituted by 1 or 2 $C_1$-$C_4$-alkyl; and $R^4, R^5, R^6, R^7, R^8, R^9, R^{10}, R^{11}, R^{12}, R^{13}, R^{14}, R^{15}, R^{16}, R^{17}$ and $R^{18}$ are each hydrogen or two of the radicals $R^4, R^5, R^6$ are hydrogen and one of the radicals $R^4, R^5, R^6$ is phenyl; two of the radicals $R^7, R^8, R^9$ are hydrogen and one of the radicals $R^7, R^8, R^9$ is phenyl, two of the radicals $R^{12}, R^{13}, R^{14}$ are hydrogen and one of the radicals $R^{12}, R^{13}, R^{14}$ is phenyl; two of the radicals $R^{15}, R^{16}, R^{17}$ are hydrogen and one of the radicals $R^{15}, R^{16}, R^{17}$ is phenyl.
a compound of formulae (VI-5), (VI-6), (VI-7), or (VI-8) or a mixture thereof as compound comprising at least one structural unit of formula (VI).

In this specific embodiment, the polymer matrix consists of polycarbonate. In a further specific embodiment, the polymer matrix consists of polystyrene. In a further specific embodiment, the polymer matrix consists of polyethylene terephthalate.

The concentration of the organic fluorescent dyes in the polymer matrix is set as a function of the thickness of the color converter and the type of polymer. If a thin polymer layer is used, the concentration of the organic fluorescent dye(s) is generally higher than in the case of a thick polymer layer.

Typically, the amount of organic fluorescent dyes in the polymer also depends on the correlated color temperature CCT to be achieved. A skilled person will appreciate that by increasing the concentration of yellow fluorescent dye(s) and red fluorescent dye(s), the light emitted from the LED is tuned to longer wavelength to obtain white light with a required CCT.

Typically, the concentration of the red organic fluorescent dye of formula (I) according to the present invention is usually in the range from 0.0001 to 0.5% by weight, preferably 0.001 to 0.1% by weight, based on the amount of polymer used. The concentration of a further yellow or yellow-green organic fluorescent dyes typically is 0.002 to 0.5% by weight, preferably 0.003 to 0.4% by weight, based on the amount of the polymer used.

The ratio of the further yellow or yellow-green emitting organic fluorescent dye to the at least one red organic fluorescent dye of the formula (I) is typically in the range from 1:1 to 25:1, preferably 2:1 to 20:1, more preferably 2:1 to 15:1, such as 10:1 or 3:1 or 4:1. A skilled person will readily appreciate that the ratio of the dyes depends on the chosen light source. For a desired CCT, the ratio of yellow dye/red dye is much greater, if the light is generated by a blue LED with a center wavelength of emission between 420 nm and 480 nm in comparison to the ratio of yellow dye/red dye if the light is generated by a white LED having a CCT between 6,000 to 20 000 K.

According to a specific embodiment, the red fluorescent dye of formula (I) according to the invention is used in combination with one further organic fluorescent dye as defined above, especially a yellow fluorescent dye. According to a further specific embodiment, the red fluorescent dye of formula (I) according to the invention is used in combination with two further organic fluorescent dye, especially a yellow or yellow-green fluorescent dye and a further red fluorescent dye different from the dye of formula (I) according to the present invention or an orange organic fluorescent dye.

The color converter may further comprise at least one inorganic phosphor material. The inorganic phosphor material is preferably selected from garnets, silicates, sulfides, nitrides and oxynitrides. Particularly preferred among these are those selected from garnets, silicates, sulfides, nitrides and oxynitrides. Suitable examples of garnets, silicates, sulfides, nitrides and oxynitrides are compiled in table 1 below:

TABLE 1

| Class | Compounds | Excitation Peak nm | Emission Peak nm | Reference |
|---|---|---|---|---|
| Garnets | YAG:Ce ($Y_3Al_5O_{12}$:Ce) (Y, Gd, Tb, Lu)$_3$Al$_5$O$_{12}$:Ce | 460-470 | 550 | U.S. Pat. No. 5,998,925 |
|  | TAG:Ce (Tb$_3$Al$_5$O$_{12}$:Ce) | 460-470 | 575 | U.S. Pat. No. 6,669,866, U.S. Pat. No. 6,812,500, U.S. Pat. No. 6,576,930, U.S. Pat. No. 6,060,861, U.S. Pat. No. 6,245,259, U.S. Pat. No. 6,765,237 |
| Silicates | Eu-doped Silicates A$_2$Si(OD)$_4$:Eu with A = Sr, Ba, Ca, Mg, Zn and D = F, Cl, S, N, Br | <460 | 510 to 610 | U.S. Pat. No. 7,311,858, U.S. Pat. No. 7,267,787 |
|  | (SrBaCa)$_2$SiO$_4$:Eu |  |  | U.S. Pat. No. 6,809,347, U.S. Pat. No. 6,943,380 |
|  | Sr$_3$SiO$_5$ Ba$_2$MgSi$_2$O$_7$:Eu$^{2+}$; Ba$_2$SiO$_4$:Eu$^{2+}$ (Ca,Ce)$_3$(Sc,Mg)$_2$Si$_3$O$_{12}$ |  |  | U.S. Pat. No. 6,429,583 WO 02/11214 |
| Sulfides | (Ca, Sr)S:Eu | <460 | 615-660 |  |
| Nitrides | (CaAlSiN$_3$:Eu$^2$) (Sr,Ca)AlSiN$_3$:Eu$^{2+}$ | 455 | red orange | WO 2005052087 |
| Oxy-nitrides | SiAlON:Ce β-SiAlON:Eu Ca-alpha-SiAlON:Eu (Ba$_3$Si$_6$O$_{12}$N$_2$:Eu) General formula Ca$_x$Eu$_y$(Si,Al)$_{12}$(O,N)$_{16}$ | 300-580 | 490 540 585-595 |  |

The inventive color converter may further comprise at least one quantum dot. Quantum dots are nanocrystals of a semiconductor material having a diameter of about 20 nm or less. The quantum dot may include one of a Si-based nanocrystal, a group II-VI compound semiconductor nanocrystal, a group III-V compound semiconductor nanocrystal, a group IV-VI compound nanocrystal and a mixture thereof. The group II-VI compound semiconductor nanocrystal may include one selected from a group consisting of CdS, CdSe, CdTe, ZnS, ZnSe, ZnTe, HgS, HgSe, HgTe, CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HggZnTe, CdZnSeS, CdZnSeTe, CdZnSTe, CdHgSeS, CdHgSeTe, CdHgSTe, HgZnSeS, HgZnSeTe and HgZnSTe. The group III-V compound semiconductor nanocrystal may include one selected from a group consisting of GaN, GaP, GaAs, AlN, AlP, AlAs, InN, InP, InAs, GaNP, GaNAs, GaPAs, AlNP, AlNAs, AlPAs, InNP, InNAs, InPAs, GaAlNP, GaAlNAs, GaAlPAs, GaInNP, GaInNAs, GaInPAs, InAlNP, InAlNAs, and InAlPAs. The IV-VI compound semiconductor nano crystal may be SnTe.

To synthesize a nanocrystal in form of a quantum dot, quantum dots may be prepared by vapor deposition such as metal organic chemical vapor deposition or molecular beam epitaxy, or by a wet chemical process in which a crystal is grown by adding one or more precursors into an organic solvent.

According to one embodiment of the invention, inventive color converters have a laminate structure. They may either have a monolayer structure or a multilayer structure, generally composed of a plurality of polymer layers comprising one or more fluorescent dyes and/or scattering bodies. If the color converter has a multilayer structure, one layer comprises the red fluorescent dye according to the invention and another layer comprises at least one fluorescent dye as defined above.

In one embodiment, the at least one red organic fluorescent dye according to the present invention is present in the layer of the color converter facing the LED. In another embodiment, the at least one further organic fluorescent dye is present in the layer of the color converter facing the LED.

According to any of the above embodiments, the color converter additionally comprises at least one inorganic white pigment as a scattering body.

In a preferred embodiment, at least one of the layers or matrices comprising organic fluorescent dye comprises scattering bodies for light.

Suitable scattering bodies are inorganic white pigments, for example titanium dioxide, barium sulphate, lithopone, zinc oxide, zinc sulphide, calcium carbonate with a mean particle size to DIN 13320 of 0.01 to 10 μm, preferably 0.1 to 1 μm, more preferably 0.15 to 0.4 μm, especially scattering bodies based on $TiO_2$.

Scattering bodies are included typically in an amount of 0.01 to 2.0% by weight, preferably 0.05 to 1% by weight, more preferably 0.1 to 0.5% by weight, based in each case on the polymer of the layer comprising scattering bodies.

In a preferred embodiment, the color converter has a two-layer structure with a red-fluorescing layer and a green-yellow-fluorescing layer comprising at least one fluorescent dye present in accordance with the invention, with the red layer facing the blue light source. In this embodiment, both layers comprise $TiO_2$ as a scattering body.

In one embodiment, the color converters consist of a plurality of polymer layers which have been laminated together to form a composite and wherein the various fluorescent dyes/colorants and/or scattering bodies may be present in different polymer layers.

If inventive color converters comprise more than one organic fluorescent dyes/colorant, it is possible in one embodiment of the invention for a plurality of fluorescent dyes/colorants to be present alongside one another in one layer.

In another embodiment, the various fluorescent dyes/colorants are present in various layers.

In a preferred embodiment, the inventive color converter comprises the at least one organic fluorescent dye of formula (I) present in accordance with the invention or mixtures thereof; at least one further organic fluorescent dye selected from compounds of formula (II) and mixtures thereof, compounds of formula (IV) and mixtures thereof, compounds having a structural unit of formula (VI) and mixtures thereof, compounds of formula (VII), compounds of formula (VIII), compounds of formula (IX), compounds of formula (X) and compounds of formula (XI) and mixtures thereof, and mixtures thereof; scattering bodies based on $TiO_2$; and at least one polymer consisting essentially of polystyrene, polyethylene terephthalate or polycarbonate.

More preferably, inventive color converters comprise
at least one organic fluorescent dye of formula (I) or mixtures thereof, wherein $R^1$ and $R^2$ have the same meaning and are phenyl which carries 1, 2 or 3 $C_1$-$C_6$-alkyl substituents; $R^3$, $R^{10}$, $R^{11}$, and $R^{18}$ have the same meaning and are phenyl, which is unsubstituted or phenyl which is substituted by 1 or 2 $C_1$-$C_4$-alkyl; and $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R^{18}$ are each hydrogen; in particular $R^3$, $R^{10}$, $R^{11}$, and $R^{18}$ are each phenyl;
a compound of formulae (VI-5), (VI-6), (VI-7), or (VI-8) or a mixture thereof as compound comprising at least one structural unit of formula (VI),
scattering bodies based on $TiO_2$; and
at least one polymer consisting essentially of polyethylene terephthalate.

Likewise, more preferably, inventive color converters comprise
at least one organic fluorescent dye of formula (I) or mixtures thereof, wherein $R^1$ and $R^2$ have the same meaning and are phenyl which carries 1, 2 or 3 $C_1$-$C_6$-alkyl substituents; $R^3$, $R^{10}$, $R^{11}$, and $R^{18}$ have the same meaning and are phenyl, which is unsubstituted or phenyl which is substituted by 1 or 2 $C_1$-$C_4$-alkyl; and $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R^{18}$ are each hydrogen; in particular $R^3$, $R^{10}$, $R^{11}$, and $R^{18}$ are each phenyl;
a compound of formulae (VI-5), (VI-6), (VI-7), or (VI-8) or mixtures thereof as compound comprising at least one structural unit of formula (VI);
scattering bodies based on $TiO_2$; and
at least one polymer consisting essentially of polystyrene.

Likewise, more preferably, inventive color converters comprise
at least one organic fluorescent dye of formula (I) or mixtures thereof, wherein $R^1$ and $R^2$ have the same meaning and are phenyl which carries 1, 2 or 3 $C_1$-$C_6$-alkyl substituents; $R^3$, $R^{10}$, $R^{11}$, and $R^{18}$ have the same meaning and are phenyl, which is unsubstituted or phenyl which is substituted by 1 or 2 $C_1$-$C_4$-alkyl; and $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R^{18}$ are each hydrogen; in particular $R^3$, $R^{10}$, $R^{11}$, and $R^{18}$ are each phenyl;
a compound of formulae (VI-5), (VI-6), (VI-7), or (VI-8) and or a mixture thereof as compound comprising at least one structural unit of formula (VI),
scattering bodies based on $TiO_2$; and
at least one polymer consisting essentially of polycarbonate.

In a further embodiment, at least one polymer layer of the color converter has been mechanically reinforced with glass fibers.

Inventive color converters may be in any desired geometric arrangement. The color converters may, for example, be in the form of films, sheets or plaques. Equally, the matrix containing organic fluorescent dyes may be in droplet form or hemispherical form or in the form of lenses with convex and/or concave, flat or spherical surfaces.

"Casting" refers to the embodiment where LEDs or components comprising LEDs are cast or enveloped fully with a polymer comprising organic fluorescent dye.

In one embodiment of the invention, the polymer layers (matrices) comprising organic fluorescent dye are 25 to 400 micrometers (μm) thick, preferably 35 to 300 μm and particularly 50 to 200 μm.

In another embodiment, the polymer layers comprising organic fluorescent dyes are 0.2 to 5 millimeters thick, preferably 0.3 to 3 mm and more preferably 0.4 to 1 mm.

If the color converters consist of one layer or they have a laminate structure, the individual layers, in a preferred embodiment, are continuous and do not have any holes or interruptions.

Inventive color converters may optionally comprise further constituents such as a backing layer.

Backing layers serve to impart mechanical stability to the color converter. The type of material for the backing layers is not crucial, provided that it is transparent and has the desired mechanical strength. Suitable materials for backing layers are, for example, glass or transparent rigid organic polymers such as polycarbonate, polystyrene or polymethacrylates or polymethyl methacrylates.

Backing layers generally have a thickness of 0.1 mm to 10 mm, preferably 0.2 mm to 5 mm, more preferably 0.3 mm to 2 mm.

In one embodiment of the invention, inventive color converters have at least one barrier layer against oxygen and/or water, as disclosed in WO 2012/152812. Examples of suitable barrier materials for barrier layers are, for example, glass, quartz, metal oxides, $SiO_2$, a multilayer system composed of alternating layers of $Al_2O_3$ and $SiO_2$ layers, titanium nitride, $SiO_2$/metal oxide multilayer materials, polyvinyl alcohol, polyacrylonitrile, polyvinylidene chloride (PVDC), liquid crystal polymers (LCP), polystyrene-acrylonitrile (SAN), polybutylene terephthalate (PBT), polybutylene naphthalate (PBN), polyethylene terephthalate (PET), polyethylene naphthalate (PEN), polyvinyl butyrate (PBT), polyvinyl chloride (PVC), polyamides, polyoxymethylenes, polyimides, polyetherimides, epoxy resins, polymers which derive from ethylene-vinyl acetate (EVA) and polymers which derive from ethylene-vinyl alcohol (EVOH).

A preferred material for barrier layers is glass or a multilayer system composed of alternating layers of $Al_2O_3$ and $SiO_2$ layers.

Preferably, suitable barrier layers have low permeability for oxygen.

More preferably, suitable barrier layers have low permeability for oxygen and water.

A further aspect of the invention relates to the use of color converters as defined above for the conversion of light generated by a LED. Especially, the invention relates to the use of color converters as defined above for the conversion of light generated by a blue LED with a center wavelength of emission between 420 nm and 480 nm to provide white light.

Likewise, the present invention relates to the use of a color converter as defined above for conversion of light generated by a cool white LED having a correlated color temperature between 6000 K and 20000 K to provide white light having a lower correlated color temperature. More particularly, they are suitable for conversion of light generated by white LEDs with a CCT between 20,000 K to 6,000 K, such as 20,000 K to 8,000 K, 15,000 K to 8,100 K or 12,000 K to 8200 K to generate light having a lower CCT for example in a range from 2,000K to 5,000 K. In other words, the inventive color converters are capable to shift the wavelength of the white light source towards longer wavelength direction (i.e. redshift) to generate white light with a warm light tone.

Cool white LEDs with a CCT between 6000 K to 20000 K are commercially available. Blue LEDs with a center wavelength of emission between 420 nm and 480 nm are also commercially available.

They are additionally suitable for applications as a light-collecting system (fluorescence collector) in photovoltaics and in fluorescence conversion solar cells.

Inventive fluorescent dyes of formula (I) have a high photostability on illumination with light generated by blue LEDs with a center wavelength of emission between 420 nm and 480 nm. Inventive fluorescent dyes of formula (I) have also a high photostability on illumination with light generated by white LEDs with a CCT between 20,000 K to 6000 K. Moreover, inventive fluorescent dyes of formula (I) are stable toward oxygen and water.

Inventive color converters can be produced by different processes.

In one embodiment, the process for producing inventive color converters comprises the dissolution of the at least one polymer and the at least one organic fluorescent dye and, if present, further organic fluorescent dyes, in a solvent and subsequent removal of the solvent.

In another embodiment, the process for producing inventive color converters comprises the extrusion of the at least one organic fluorescent dye and, if present, further organic fluorescent dyes with the at least one polymer.

A further aspect of the invention relates to lighting devices comprising at least one white LED having a CCT between 6000 K and 20000 K and at least one color converter as defined above, wherein the color converter and the LED are in remote phosphor arrangement. Still a further aspect of the invention relates to lighting devices comprising at least one blue LED with a center wavelength of emission between 420 nm and 480 nm and at least one color converter as defined above, wherein the color converter and the LED are in remote phosphor arrangement.

In one embodiment, inventive lighting devices comprise a plurality of LEDs selected from a blue LED with a center wavelength of emission between 420 nm and 480 nm and a white LED having a CCT between 6000 K and 20000 K. Inventive color converters can be used in combination with LEDs selected from blue LEDs with a center wavelength of emission between 420 nm and 480 nm and white LEDs having a CCT between 6000 K and 20000 K in virtually any geometric form and irrespective of the construction of the lighting device.

Inventive color converters are used in a remote phosphor setup. In this case, the color converter is spatially separated from the LED. In general, the distance between LED and color converter is from 0.1 cm to 50 cm, preferably 0.2 to 10 cm and most preferably 0.5 to 3 cm. Between color converter and LED may be different media such as air, noble gases, nitrogen or other gases or mixtures thereof.

The color converter may, for example, be arranged concentrically around the LED or have a planar geometry. It may take the form, for example, of a plaque, sheet or film, be in droplet form or take the form of a casting.

Inventive lighting devices are suitable for lighting in interiors, outdoors, of offices, of vehicles, in torches, games consoles, streetlights, traffic signs.

Inventive lighting devices exhibit warm-tone white light with a high average color rendering index. In addition, they have a long lifetime, especially a high photostability on illumination with blue light.

A further aspect of the invention relates to the use of a perylene bisimide compound of the formula (I) or a mixture thereof in color converters for converting light emitted from a light source, in particular a light source selected from LEDs and OLEDs, into light of a second, longer wavelength, for coloring coatings, printing inks and plastics, producing aqueous polymer dispersions which absorb and/or emit electromagnetic radiation, for data storage, for optical labels, for security labels in documents and for brand protection or as a fluorescent label for biomolecules. The compounds of formula (I) are highly fluorescent making them useful for security inks. A further aspect relates to the use of a perylene bisimide compound of the formula (I) as defined above or mixtures thereof in security inks for security printing due to their remarkable optical properties. The wavelength of the emitted light may be from 500 to about 750 nm.

Accordingly, a further aspect of the present invention is a printing ink formulation for security printing, comprising at least one compound of the formula (I) or a mixture thereof as defined above.

Security printing is the field that deals with the printing of items such as currency, passports, tamper-evident labels, stock certificates, tax stamps, postage stamps, identity cards, etc. The main goal of security printing is to prevent forgery, tampering or counterfeiting.

In the field of automated banknote processing, UVabsorption plays an important role. Most of the actually circulating currency carries not only visibly coloured printings, but also specific features which are only detectable upon exposure to UV light. Generally, these features are implemented for use by automatic currency processing equipment, in banking and vending applications (automatic teller machines, automatic vending machines, etc.), in order to recognize a determined currency bill and to verify its authenticity, in particular to discriminate it from replicas made by colour copiers.

All security documents are required to have good stability and durability. In the case of bank notes, these requirements are extreme, as bank notes are subjected to toughest use conditions by the public—they are subjected to material stress by folding, crumpling etc., subjected to abrasion, exposed to weather, exposed to bodily fluids such as perspiration, laundered, dry-cleaned, ironed etc. —and, after having been subjected to this, are expected to be as legible as when they started. Furthermore, it is essential that the documents nevertheless should have a reasonable life time, ideally of some years, despite suffering the afore-mentioned conditions. During this time, the documents, and thus the inks on them (including invisible security markings), should be resistant to fading or colour change. Hence, any ink used in a security printing process should, when cured, be robust, water-resistant, resistant to various chemicals and flexible. Moreover, as certain states are moving away from the use of paper as the substrate for bank notes, the employed printing ink formulations should be useable on plastics as well as paper. It has now been found that the compounds of the general formula (I) because of their unique application properties are especially suitable for printing ink formulations that are employed for security printing and in particular for bank notes.

In security printing, the fluorescent dye is added to a printing ink formulation. Suitable printing inks are water-based, oil-based, or solvent-based printing inks, based on pigment or dye, for inkjet printing, flexographic printing, gravure printing, screen printing, intaglio printing, offset printing, laser printing or letterpress printing and for use in electrophotography. Printing inks for these printing processes usually comprise solvents, binders, and also various additives, such as plasticizers, antistatic agents or waxes. Printing inks for offset printing, letterpress printing and intaglio printing are usually formulated as high-viscosity paste printing inks, whereas printing inks for flexographic printing and inkjet printing are usually formulated as liquid printing inks with comparatively low viscosity.

In the context of the present invention, the expression "printing ink" also encompasses formulations that in addition to at least one fluorescent dye of the general formula (I) comprise a colorant. The expression "printing ink" also encompasses printing lacquers that comprise no colorant.

The printing ink formulation for security printing according to the invention preferably comprises
a) at least one compound of the formula (I) or a mixture thereof as defined above;
b) a polymeric binder;
c) optionally an organic solvent;
d) optionally at least one colorant; and
e) optionally at least one further additive.

Suitable components of printing inks are conventional and are well known to those skilled in the art. Examples of such components are described in "Printing Ink Manual", fourth edition, Leach R. H. et al. (eds.), Van Nostrand Reinhold, Wokingham, (1988). Details of printing inks and their formulation are also disclosed in "Printing Inks"-Ullmann's Encyclopedia of Industrial Chemistry, Sixth Edition, 1999 Electronic Release.

The printing ink formulation according to the invention contains in general from 0.0001 to 25% by weight, preferably from 0.001 to 15% by weight, in particular from 0.01 to 5% by weight, based on the total weight of the printing ink formulation, of component a).

The compounds of the general formula (I) are present in the printing ink formulation in dissolved form or in solid form (in a finely divided state).

The printing ink formulation according to the invention contains in general from 5 to 75% by weight, preferably from 10 to 60% by weight, more preferably from 15 to 40% by weight, based on the total weight of the printing ink formulation, of component b).

Suitable polymeric binders b) for the printing ink formulation according to the invention are for example selected from natural resins, phenol resin, phenol-modified resins, alkyd resins, polystyrene homo- and copolymers, terpene resins, silicone resins, polyurethane resins, urea-formaldehyde resins, melamine resins, polyamide resins, polyacrylates, polymethacrylates, chlorinated rubber, vinyl ester resins, acrylic resins, epoxy resins, nitrocellulose, hydrocarbon resins, cellulose acetate, and mixtures thereof.

The printing ink formulation according to the invention can also comprise components that form a polymeric binder by a curing process. Thus, the printing ink formulation according to the invention can also be formulated to be energy-curable, e.g. able to be cured by UV light or EB (electron beam) radiation. In this embodiment, the binder comprises one or more curable monomers and/oligomers. Corresponding formulations are known in the art and can be found in standard textbooks such as the series "Chemistry & Technology of UV & EB Formulation for Coatings, Inks & Paints", published in 7 volumes in 1997-1998 by John Wiley & Sons in association with SITA Technology Limited.

Suitable monomers and oligomers (also referred to as prepolymers) include epoxy acrylates, acrylated oils, urethane acrylates, polyester acrylates, silicone acrylates, acrylated amines, and acrylic saturated resins. Further details and examples are given in "Chemistry & Technology of UV & EB Formulation for Coatings, Inks & Paints", Volume II: Prepolymers & Reactive Diluents, edited by G Webster.

If a curable polymeric binder is employed, it may contain reactive diluents, i.e. monomers which act as a solvent and which upon curing are incorporated into the polymeric binder. Reactive monomers are typically chosen from acrylates or methacrylates, and can be monofunctional or multifunctional. Examples of multifunctional monomers include polyester acrylates or methacrylates, polyol acrylates or methacrylates, and polyether acrylates or methacrylates.

In the case of printing ink formulations to be cured by UV radiation, it is usually necessary to include at least one photoinitiator to initiate the curing reaction of the monomers upon exposure to UV radiation. Examples of useful photoinitiators can be found in standard textbooks such as "Chemistry & Technology of UV & EB Formulation for Coatings, Inks & Paints", Volume III, "Photoinitiators for Free Radical Cationic and Anionic Polymerisation", 2nd edition, by J. V. Crivello & K. Dietliker, edited by G. Bradley and published in 1998 by John Wiley & Sons in association with SITA Technology Limited. It may also be advantageous to include a sensitizer in conjunction with the photoinitiator in order to achieve efficient curing.

The printing ink formulation according to the invention contains in general from 0 to 94.9999% by weight, preferably from 5 to 90% by weight, in particular from 10 to 85% by weight, based on the total weight of the printing ink formulation, of a solvent c).

Suitable solvents are selected from water, organic solvents and mixtures thereof. For the purpose of the invention, reactive monomers which also act as solvents are regarded as part of the afore-mentioned binder component b).

Examples of solvents comprise water; alcohols, e.g. ethanol, 1-propanol, 2-propanol, ethylene glycol, propylene glycol, diethylene glycol and ethoxy propanol; esters, e.g. ethyl acetate, isopropyl acetate, n-propyl acetate and n-butyl acetate; hydrocarbons, e.g. toluene, xylene, mineral oils and vegetable oils, and mixtures thereof.

The printing ink formulation according to the invention may contain an additional colorant d). Preferably, the printing ink formulation contains from 0 to 25% by weight, more preferably from 0.1 to 20% by weight, in particular from 1 to 15% by weight, based on the total weight of the printing ink formulation, of a colorant d).

Suitable colorants d) are selected conventional dyes and in particular conventional pigments. The term "pigment" is used in the context of this invention comprehensively to identify all pigments and fillers, examples being colour pigments, white pigments, and inorganic fillers. These include inorganic white pigments, such as titanium dioxide, preferably in the rutile form, barium sulfate, zinc oxide, zinc sulfide, basic lead carbonate, antimony trioxide, lithopones (zinc sulfide+barium sulfate), or coloured pigments, examples being iron oxides, carbon black, graphite, zinc yellow, zinc green, ultramarine, manganese black, antimony black, manganese violet, Paris blue or Schweinfurt green. Besides the inorganic pigments the printing ink formulation of the invention may also comprise organic colour pigments, examples being sepia, gamboge, Cassel brown, toluidine red, para red, Hansa yellow, indigo, azo dyes, anthraquinonoid and indigoid dyes, and also dioxazine, quinacridone, phthalocyanine, isoindolinone, isoindoline, perylene and metal complex pigments. Also suitable are synthetic white pigments with air inclusions to increase the light scattering, such as the Rhopaque® dispersions. Suitable fillers are, for example, aluminosilicates, such as feldspars, silicates, such as kaolin, talc, mica, magnesite, alkaline earth metal carbonates, such as calcium carbonate, in the form for example of calcite or chalk, magnesium carbonate, dolomite, alkaline earth metal sulfates, such as calcium sulfate, silicon dioxide, etc.

The printing ink formulation according to the invention may contain at least one additive e). Preferably, the printing ink formulation contains from 0 to 25% by weight, more preferably from 0.1 to 20% by weight, in particular from 1 to 15% by weight, based on the total weight of the printing ink formulation, of at least one component e).

Suitable additives (component e)) are selected from plasticizers, waxes, siccatives, antistatic agents, chelators, antioxidants, stabilizers, adhesion promoters, surfactants, flow control agents, defoamers, biocides, thickeners, etc. and combinations thereof. These additives serve in particular for fine adjustment of the application-related properties of the printing ink, examples being adhesion, abrasion resistance, drying rate, or slip.

In particular, the printing ink formulation for security printing according to the invention preferably contains
a) 0.0001 to 25% by weight of at least one compound of the formula (I) or a mixture thereof as defined above,
b) 5 to 75% by weight of at least one polymeric binder,
c) 0 to 94.9999% by weight of at least one solvent,
d) 0 to 25% by weight of at least one colorant, and
e) 0 to 25% by weight of at least one further additive,
wherein the sum of components a) to e) adds up to 100%.

The printing ink formulations according to the invention are advantageously prepared in a conventional manner, for example by mixing the individual components. As mentioned earlier, the fluorescent dye of formula (I) is present in the printing ink formulations in a dissolved or finely divided solid form. Additional colorants may be employed in the printing ink formulation of the invention or in a separate ink formulation. When additional colorants are to be employed in a separate formulation, the time of application of the printing ink formulation according to the invention is usually immaterial. The printing ink formulation according to the invention can for example be applied first and then be overprinted with conventional printing inks. But it is also possible to reverse this sequence or, alternatively, to apply the printing ink formulation according to the invention in a mixture with conventional printing inks. In every case the prints are readable with suitable light sources.

Primers can be applied prior to the printing ink formulation according to the invention. By way of example, the primers are applied in order to improve adhesion to the substrate. It is also possible to apply additional printing lacquers, e.g. in the form of a covering to protect the printed image. Additional printing lacquers may also be applied to serve aesthetic purposes, or serve to control application-related properties. By way of example, suitably formulated additional printing lacquers can be used to influence the roughness of the surface of the substrate, the electrical properties, or the water-vapour-condensation properties. Printing lacquers are usually applied in-line by means of a lacquering system on the printing machine employed for printing the printing ink formulation according to the invention.

The printing ink formulations according to the invention are also suitable for use in multilayer materials. Multilayer materials are e.g. composed of two or more plastics foils, such as polyolefin foils, metal foils, or metallised plastics foils, which are bonded to one another, by way of example, via lamination or with the aid of suitable laminating adhesives. These composites may also comprise other functional layers, such as optically variable layers, odour-barrier layers or water-vapour barriers.

The printing ink formulations according to the present invention are especially suitable for offset, letterpress, gravure and intaglio printing.

When a transparent substrate is used, the type of lamp for exciting the fluorescent dye of formula (I) is generally not critical, i.e. all light sources emitting light at wavelength within the absorption profile of the fluorescent dye of formula (I). For example high or medium pressure mercury lamps are sufficient. Any ultraviolet light source may be employed as a radiation source, such as, a high or low pressure mercury lamp, a black light, an ultraviolet LED, or an ultraviolet laser.

A further aspect of the present invention is a process for the manufacture of a security document comprising the steps printing on a substrate a printing ink formulation as defined above.

A further aspect is a security document, comprising a substrate, a cured ink which ink comprises at least one compound of the formula (I) or a mixture thereof as defined above.

A further aspect is a security document as defined above obtainable by a printing process wherein a printing ink formulation as defined above is employed. The security document is preferably selected from a bank note, a passport, a check, a voucher, an ID- or transaction card, a stamp and a tax label. The security document can also be part of a rigid or flexible packaging, of a carton board or of a brand or product label. The present invention is now illustrated in further detail by the following examples, without imposing any limitation thereto.

EXAMPLES

Spectroscopic Measurements

The fluorescence spectra and fluorescence quantum yields were recorded using an absolute quantum yield measurement instrument (C9920-02) manufactured by Hamamatsu, and, if necessary, equipped with cuvettes for liquid samples. The spectra were recorded at an excitation wavelength of 450 and 510 nm.

I. Preparation of Compound of Formula (I)

Example 1: Compound of Formula (I), where $R^1=R^2=2,6$-Diisopropylphenyl; $R^3=R^{10}=R^{11}=R^{18}=$Phenyl; $R^4=R^5=R^6=R^7=R^8=R^9=R^{12}=R^{13}=R^{14}=R^{15}=R^{16}=$Hydrogen

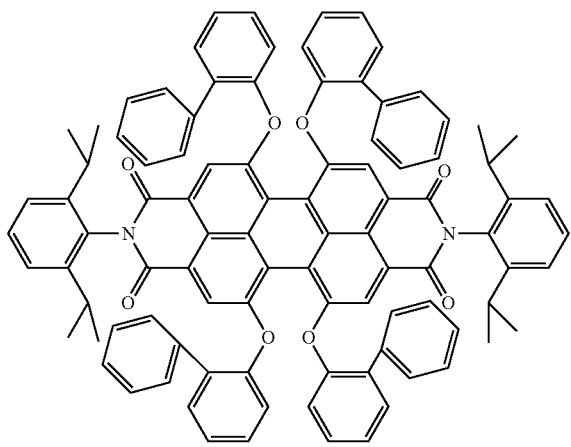 [SMILES: CC(C)c1cccc(C(C)C)c1N1C(=O)c2cc(Oc3ccccc3-c3ccccc3)c3c4c(Oc5ccccc5-c5ccccc5)cc5c6c(cc(Oc7ccccc7-c7ccccc7)c(c7c(Oc8ccccc8-c8ccccc8)cc(c2c37)C1=O)c64)C(=O)N(c1c(C(C)C)cccc1C(C)C)C5=O]

A mixture of 5 g (5.9 mmol) of N,N'-(2,6-diisopropylphenyl)-1,6,7,12,-tetrachloro-perylenetetracarboxylic diimide, 4.23 g of (24.9 mmol) biphenyl-2-ol, 138.21 g (16.9 mmol) of potassium carbonate and 30 mL of N-methyl-2-pyrrolidone (NMP) were stirred at room temperature for 24 h and then for 48 h at 115° C. After cooling to 80° C. the reaction mixture was added dropwise to a mixture of 10 mL of acetic acid and 20 mL of water within 15 min, cooled to room temperature over a period of 2 h and then filtered. The residue was washed with 300 mL of a mixture of ethanol/water (1:1) and then with 600 mL of a mixture of ethanol/water/NMP (4:4:1). The residue was dissolved in a mixture of 35 mL of ethanol and 5 mL of NMP under reflux, then cooled to room temperature and separated to obtain 5.6 g (62%) of a red dye which was purified by chromatography using cyclohexane/ethyl acetate. The yield was 2.06 g (23%). Rf (cylohexane/ethyl acetate 10:1)=0.29.

Example 2: Compound of Formula (I), where $R^1=R^2=2,6$-Diisopropylphenyl; $R^3=R^{10}=R^{11}=R^{18}=$Phenyl; $R^4=R^6=R^7=R^9=R^{12}=R^{14}=R^{15}=$Hydrogen; $R^5=R^8=R^{13}=R^{16}=$Phenyl

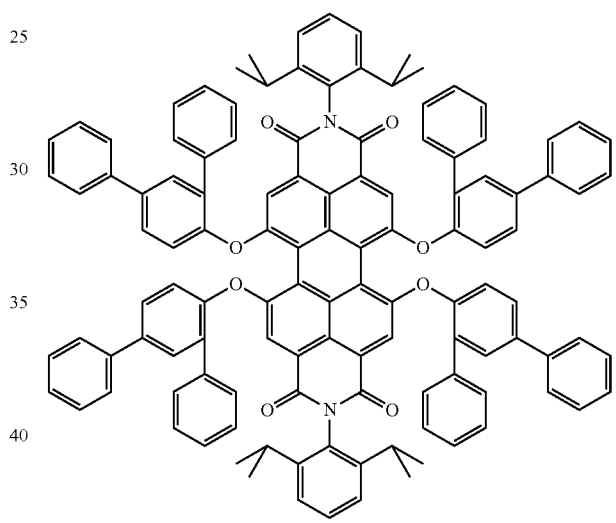

A mixture of 4.24 g (5 mmol) of N,N'-(2,6-diisopropylphenyl)-1,6,7,12-tetrachloro-perylenetetracarboxylic diimide, 25 mL of NMP, 6.16 g (25 mmol) of 2,4 diphenylphenol and 3.46 g (25 mmol) of $K_2CO_3$ were heated to 120° C. for 16 hours. The reaction mixture is cooled to 60° C. and 75 mL of methanol were added. The formed suspension was filtered and washed with methanol 4 times while being stirred on the frit. The residue was washed with hot water several times and dried at 70° C. in vacuo. 5.87 g (70%) of the title product were obtained. According to HPLC the purity is 96.4%.

Rf (petroleum ether: tert-butyl methyl ether=10:2)=0.43

Lambda max emission: 629 nm (in polycarbonate).

FQY in PC 92%.

II. Preparation of Color Converters

Materials used:

LED 1: cool white LED with CCT of 9109 K

LED 2: cool white LED with CCT of 8595 K

Polymer 1: transparent polycarbonate based on a polycondensate of bisphenol A and phosgene (Makrolon® 2805 from Bayer MaterialScience AG)

Dye 1: Yellow fluorescent dye
Compound of formula (VI-5)

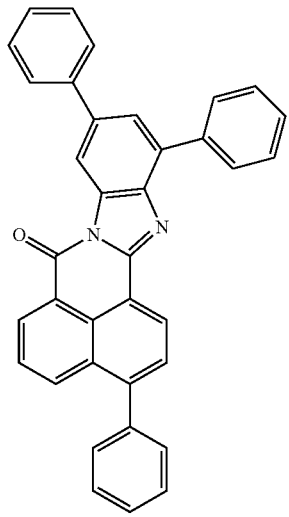

(VI-5)

obtained as described in example 10 of WO 2012/168395, followed by purification with chromatography. The mixture comprising the compound VI-5 is subjected to a further column chromatography to give the pure compound VI-5.

Dye 2: Inventive red fluorescent dye
Compound from example 1

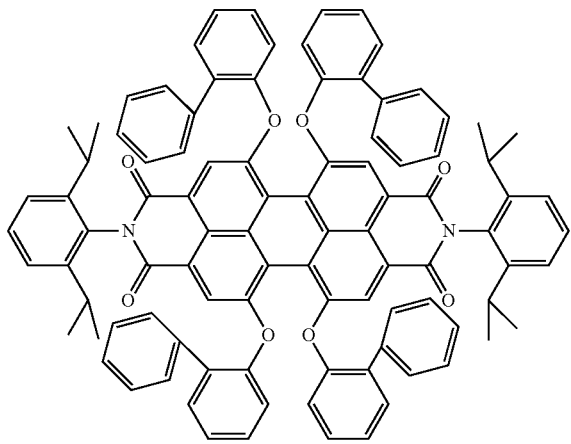 [SMILES: CC(C)c1cccc(C(C)C)c1N1C(=O)c2cc(Oc3ccccc3-c3ccccc3)c3c4c(Oc5ccccc5-c5ccccc5)cc5c6c(cc(Oc7ccccc7-c7ccccc7)c(c7c(Oc8ccccc8-c8ccccc8)cc(c2c37)C1=O)c64)C(=O)N(c1c(C(C)C)cccc1C(C)C)C5=O]

Dye 3: Red-fluorescent dye (not according to the invention)

N, N'-bis(2,6-diisopropylphenyl)-1,6,7,12-tetra-phenoxyperylene-3,4;9,10-tetracarboxylic acid diimide

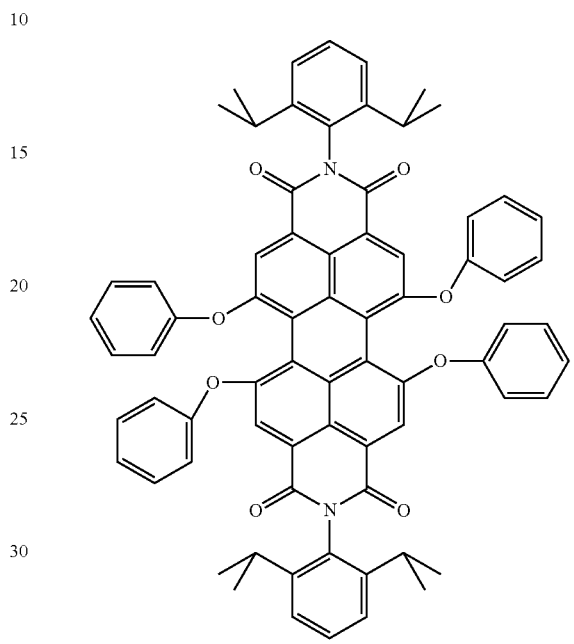

available from BASF SE.

Titanium dioxide: $TiO_2$ rutile pigment: Kronos® 2233—from Kronos Titan

Production of Color Converters:

To produce the converter materials, i.e. polycarbonate, dyes and $TiO_2$ (Kronos 2233) according to the desired concentrations (see Table I), were mixed with dichloromethane. The solution/dispersion obtained was coated onto a glass surface using an applicator frame (wet film thickness 800 μm from Ericsen). After the solvent had dried off, the film was detached from the glass and dried. Circular polymer plates were obtained.

TABLE I

| Example | yellow dye 1 [% by wt.] | red dye 2 [% by wt.] | red dye 3 [% by wt.] | red dye/ yellow dye | $TiO_2$ [% by wt.] | Film thickness [μm] |
|---|---|---|---|---|---|---|
| C1 | 0.0341 | — | 0.0070 | 0.2055 | 0.80 | 131.8 |
| C2 | 0.0345 | — | 0.00661 | 0.1913 | 0.50 | 140.1 |
| A1 | 0.0300 | 0.0108 | — | 0.3600 | 0.80 | 135.0 |
| A2 | 0.0330 | 0.0116 | — | 0.3515 | 0.50 | 154.5 |
| A3 | 0.0325 | 0.0113 | — | 0.3477 | 0.50 | 146.5 |

The amount of yellow fluorescent dye 1, red-fluorescent dye 2, red-fluorescent dye 3 and $TiO_2$ are each based on the amount of polymer polycarbonate used.

Since the spectrum of inventive dye 2 is red-shifted in comparison to the spectrum of comparative dye 3, inventive examples A1, A2 and A3 comprise a greater amount of red fluorescent dye as comparative examples C1 and C2. This takes into account the color perception of the human eye which is more sensitive to yellow-green hues as to red hues.

Characterization of the Lighting Devices:

LED1 and LED2, respectively, were used as pumping light source. The light irradiated from the surface of the converter plate was subjected to a photometric measurement, where the total light irradiated from the device was measured by an integral measurement with an integrating sphere, ISP 500-100, and a CAS 140CT-156 CCD detector (from Instrument Systems, Munich). This measured radiance spectrum was used to derive all relevant photometric data such as CCT (=correlated color temperature) in Kelvin [K], average color rendering index CRI and color rendering index for reference color no. 9 (R9). The results are given in tables II and III.

TABLE II

|  | CIE-x | CIE-y | CIE-u' | CCT [K] | Planck distance | average CRI | R9 |
|---|---|---|---|---|---|---|---|
| LED 1 | 0.2987 | 0.2766 | 0.2088 | 8595 | −1.80E−02 | 81.53 | 51.56 |
| C1 | 0.4319 | 0.4019 | 0.2483 | 3068 | −1.64E−04 | 92.16 | 44.22 |
| A1 | 0.4280 | 0.3991 | 0.2469 | 3115 | −7.01E−04 | 94.03 | 78.67 |

TABLE III

|  | CIE-x | CIE-y | CIE-u' | CCT [K] | Planck distance | average CRI | R9 |
|---|---|---|---|---|---|---|---|
| LED 2 | 0.2932 | 0.2786 | 0.2037 | 9109 | −1.33E−02 | 77.77 | 28.63 |
| C2 | 0.4314 | 0.4013 | 0.2482 | 3073 | −3.12E−04 | 91.50 | 45.39 |
| A1 | 0.4321 | 0.4003 | 0.2491 | 3051 | −8.48E−04 | 93.42 | 89.80 |
| A1 | 0.4302 | 0.4001 | 0.2480 | 3083 | −6.51E−04 | 93.35 | 87.72 |

Tables II and III show that the inventive color converters (examples A1, A2, A3) and non-inventive color converters (examples C1 and C2) create warm-white light having almost similar CIE color coordinates. The inventive examples exhibit an increase in average CRI and a significant increase in R9. Since the yellow dye 1 is the same in the comparative examples as in the inventive examples, the improvement of average CRI and R9 can be attributed to the inventive red dye.

The invention claimed is:

1. A perylene bisimide compound of formula (I)

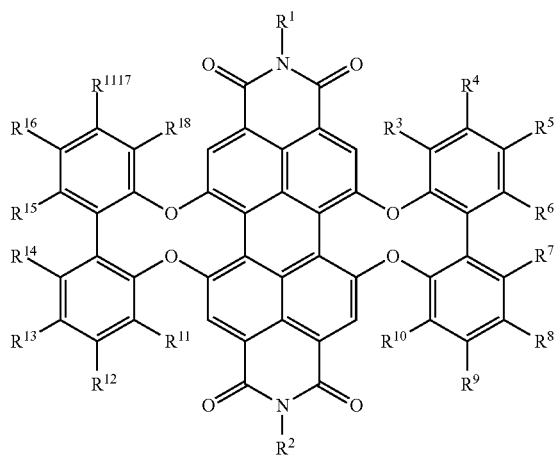

(I)

wherein $R^1$ and $R^2$, independently of each other, are hydrogen, an unsubstituted or a substituted $C_1$-$C_{30}$-alkyl, an unsubstituted or a substituted polyalkyleneoxy, an unsubstituted or a substituted $C_1$-$C_{30}$-alkoxy, an unsubstituted or a substituted $C_1$-$C_{30}$-alkylthio, an unsubstituted or a substituted $C_3$-$C_{20}$-cycloalkyl, an unsubstituted or a substituted $C_3$-$C_{20}$-cycloalkyloxy, an unsubstituted or a substituted $C_6$-$C_{24}$-aryl, or an unsubstituted or a substituted $C_6$-$C_{24}$-aryloxy;

$R^3$, $R^{10}$, $R^{11}$, and $R^{18}$, independently of each other, are phenyl or phenyl substituted by one, two, three, four or five radicals L, wherein L is halogen, cyano, hydroxyl, mercapto, —NR$^{Ar1}$COR$^{Ar2}$, unsubstituted or substituted $C_1$-$C_{30}$-alkyl, polyalkyleneoxy, $C_1$-$C_{30}$-alkoxy, $C_1$-$C_{30}$-alkylthio, $C_3$-$C_{20}$-cycloalkyl, $C_3$-$C_{20}$-cycloalkoxy, $C_6$-$C_{24}$-aryl, $C_6$-$C_{24}$-aryloxy or $C_6$-$C_{24}$-arylthio;

$R^4$, $R^5$, $R^6$, $R^7$, $R^8$, $R^9$, $R^{12}$, $R^{13}$, $R^{14}$, $R^{15}$, $R^{16}$, and $R^{17}$ independently of each other, are hydrogen, halogen, cyano, hydroxyl, mercapto, —NR$^{Ar1}$COR$^{Ar2}$, —CONR$^{Ar1}$R$^{Ar2}$, —SO$_2$NR$^{Ar1}$R$^{Ar2}$, —COOR$^{Ar1}$, —SO$_3$R$^{Ar2}$, an unsubstituted or a substituted $C_1$-$C_{30}$-alkyl, an unsubstituted or a substituted polyalkyleneoxy, an unsubstituted or a substituted $C_1$-$C_{30}$-alkoxy, an unsubstituted or a substituted $C_1$-$C_{30}$-alkylthio, an unsubstituted or a substituted $C_3$-$C_{20}$-cycloalkyl, an unsubstituted or a substituted $C_3$-$C_{20}$-cycloalkoxy, an unsubstituted or a substituted $C_6$-$C_{24}$-aryl, an unsubstituted or a substituted $C_6$-$C_{24}$-aryloxy or an unsubstituted or a substituted $C_6$-$C_{24}$-arylthio, where R⁴ and R⁵, R⁵ and R⁶, R⁷ and R⁸, R⁸ and R⁹, R¹² and R¹³, R¹³ and R¹⁴, R¹⁴ and R¹⁵, R¹⁵ and R¹⁶, and/or R¹⁶ and R¹⁷ together with the carbon atoms to which they are bonded, are optionally form a fused aromatic or non-aromatic carbon ring system wherein the fused ring system is unsubstituted or substituted;

where $R^{Ar1}$ and $R^{Ar2}$, independently of each other, are hydrogen, an unsubstituted or a substituted $C_1$-$C_{18}$-alkyl, an unsubstituted or a substituted $C_3$-$C_{20}$-cycloalkyl, an unsubstituted or a substituted heterocyclyl, an unsubstituted or a substituted $C_6$-$C_{20}$-aryl or an unsubstituted or a substituted heteroaryl.

2. The compound of claim 1, where R¹ and R² in formula (I) independently of each other are $C_1$-$C_{10}$-alkyl, which is unsubstituted or substituted by $C_6$-$C_{10}$-aryl which in turn is unsubstituted or substituted by 1, 2 or 3 $C_1$-$C_{10}$-alkyl, $C_3$-$C_8$-cycloalkyl, which is unsubstituted or substituted by 1, 2 or 3 $C_1$-$C_{10}$-alkyl, and $C_6$-$C_{10}$-aryl which is unsubstituted or substituted by 1, 2 or 3 $C_1$-$C_{10}$-alkyl.

3. The compound of claim 1, where in R³, R¹⁰, R¹¹ and R¹⁸, independently of each other, are phenyl or phenyl which is substituted by 1 or 2 radicals selected from the group consisting of $C_1$-$C_6$-alkyl, $C_1$-$C_6$-alkoxy-$C_1$-$C_6$-alkyl and $C_1$-$C_6$-alkoxy.

4. The compound of claim 1, wherein R⁴, R⁵, R⁶, R⁷, R⁸, R⁹, R¹², R¹³, R¹⁴, R¹⁵, R¹⁶ and R¹⁷, independently of each other, are hydrogen, halogen, $C_1$-$C_{18}$-alkyl, $C_6$-$C_{10}$-aryl, $C_6$-$C_{10}$-aryl-$C_1$-$C_{10}$alkylene, $C_6$-$C_{10}$-aryloxy or $C_6$-$C_{10}$-arylthio, where the aryl moiety of $C_6$-$C_{10}$-aryl, $C_6$-$C_{10}$-aryl-$C_1$-$C_{10}$-alkylene, $C_6$-$C_{10}$-aryloxy and $C_6$-$C_{10}$-arylthio is unsubstituted or substituted by one or more $C_1$-$C_{10}$-alkyl.

5. The compound of claim 4, wherein R⁴, R⁵, R⁶, R⁷, R⁸, R⁹, R¹², R¹³, R¹⁴, R¹⁵, R¹⁶ and R¹⁷, independently of each other, are hydrogen, $C_1$-$C_6$-alkyl or $C_6$-$C_{10}$-aryl.

6. A color converter, comprising at least one compound of the formula (I) of claim 1 as fluorescent dye and at least one polymer as a matrix, wherein the polymer is selected from the group consisting of polystyrene, polycarbonate, polymethyl methacrylate, polyvinylpyrrolidone, polymethacrylate, polyvinyl acetate, polyvinyl chloride, polybutene, silicone, polyacrylate, epoxy resin, polyvinyl alcohol, poly(ethylene vinylalcohol)-copolymer, polyacrylonitrile, polyvinylidene chloride, poly(styrene-acrylonitrile), polybutylene terephthalate, polyethylene terephthalate, polyvinyl butyrate, polyvinyl chloride, polyamides, polyoxymethylenes, polyimides, polyetherimides and a mixture thereof.

7. The color converter of claim 6, further comprising at least one inorganic white pigment as a scattering body.

8. The color converter of claim 7, further comprising at least one further organic fluorescent dye selected from the group consisting of (i) a cyanated naphthoylbenzimidazole compound of formula II

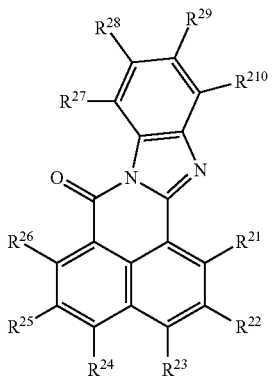

and a mixture thereof, wherein

R²¹, R²², R²³, R²⁴, R²⁵, R²⁶, R²⁷, R²⁸, R²⁹ and R²¹⁰ are each independently hydrogen, cyano or aryl which is unsubstituted or has one or more identical or different substituents $R^{2Ar}$, where each $R^{2Ar}$ is independently cyano, hydroxyl, mercapto, halogen, $C_1$-$C_{20}$-alkoxy, $C_1$-$C_{20}$-alkylthio, nitro, —NR²ᴬʳ²R²ᴬʳ³, —NR²ᴬʳ²COR²ᴬʳ³, —CONR²ᴬʳ²R²ᴬʳ³, —SO₂NR²ᴬʳ²R²ᴬʳ³, —COOR²ᴬʳ², —SO₃R²ᴬʳ², $C_1$-$C_{30}$-alkyl, $C_2$-$C_{30}$-alkenyl, $C_2$-$C_{30}$-alkynyl, $C_3$-$C_8$-cycloalkyl, 3- to 8-membered heterocyclyl, aryl, U-aryl, heteroaryl, or U-heteraryl, where $C_1$-$C_{30}$-alkyl, $C_2$-$C_{30}$-alkenyl, and $C_2$-$C_{30}$-alkynyl are unsubstituted or bear one or more $R^{2a}$ groups, $C_3$-$C_8$-cycloalkyl and 3- to 8-membered heterocyclyl are unsubstituted or bear one or more $R^{2b}$ groups, and aryl, U-aryl, heteroaryl and U-heteroaryl are unsubstituted or bear one or more $R^{2b}$ groups, where each $R^{2a}$ is independently cyano, hydroxyl, oxo, mercapto, halogen, $C_1$-$C_{20}$-alkoxy, $C_1$-$C_{20}$-alkylthio, nitro, —NR²ᴬʳ²R²ᴬʳ³, —NR²ᴬʳ²COR²ᴬʳ³, —CONR²ᴬʳ²R²ᴬʳ³, —SO₂NR²ᴬʳ²R²ᴬʳ³, —COOR²ᴬʳ², —SO₃R²ᴬʳ², $C_3$-$C_8$-cycloalkyl, 3- to 8-membered heterocyclyl, aryl, or heteroaryl, where the cycloalkyl, heterocyclyl, aryl and heteroaryl radicals are unsubstituted or bear one or more $R^{2b}$ groups, each $R^{2b}$ is independently cyano, hydroxyl, oxo, mercapto, halogen, $C_1$-$C_{20}$-alkoxy, $C_1$-$C_{20}$-alkylthio, nitro, —NR²ᴬʳ²R²ᴬʳ³, —NR²ᴬʳ²COR²ᴬʳ³, —CONR²ᴬʳ²R²ᴬʳ³, —SO₂NR²ᴬʳ²R²ᴬʳ³, —COOR²ᴬʳ², —SO₃R²ᴬʳ², $C_1$-$C_{18}$-alkyl, $C_2$-$C_{18}$-alkenyl, $C_2$-$C_{18}$-alkynyl, $C_3$-$C_8$-cycloalkyl, 3- to 8-membered heterocyclyl, aryl, or heteroaryl, where $C_3$-$C_8$-cycloalkyl, 3- to 8-memberd heterocyclyl, aryl, and heteroaryl are unsubstituted or bear one or more $R^{2b1}$ groups, each $R^{2b1}$ is independently cyano, hydroxyl, mercapto, oxo, nitro, halogen, —NR²ᴬʳ²R²ᴬʳ³, —NR²ᴬʳ²COR²ᴬʳ³, —CONR²ᴬʳ²R²ᴬʳ³, —SO₂NR²ᴬʳ²R²ᴬʳ³, —COOR²ᴬʳ², —SO₃R²ᴬʳ², —SO₃R²ᴬʳ², $C_1$-$C_{18}$-alkyl, $C_2$-$C_{18}$-alkenyl, $C_2$-$C_{18}$-alkynyl, $C_1$-$C_{12}$-alkoxy, or $C_1$-$C_{12}$-alkylthio, U is an —O—, —S—, —NR²ᴬʳ¹, —CO—, —SO— or —SO₂— moiety, $R^{2Ar1}$, $R^{2Ar2}$, $R^{2Ar3}$ are each independently hydrogen, $C_1$-$C_{18}$-alkyl, 3- to 8-membered cycloalkyl, 3- to 8-membered heterocyclyl, aryl or heteroaryl, where alkyl is unsubstituted or bears one or more $R^{2a}$ groups, where 3- to 8-membered cycloalkyl, 3- to 8-membered heterocyclyl, aryl and heteroaryl are unsubstituted or bear one or more $R^{2b}$ groups, with the proviso that the compound of the formula II comprises at least one cyano group, (ii) a cyanated perylene compound of (III)

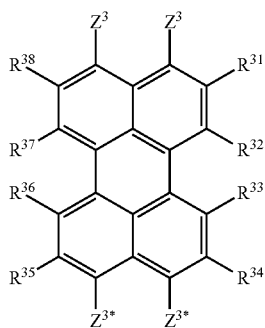

and a mixture thereof,
wherein
one of the $Z^3$ substituents is cyano and the other $Z^3$ substituent is $CO_2R^{39}$, $CONR^{310}R^{311}$, $C_1$-$C_{18}$-alkyl, $C_2$-$C_{18}$-alkenyl, $C_2$-$C_{18}$-alkynyl, $C_3$-$C_{12}$-cycloalkyl or $C_6$-$C_{14}$-aryl, where
$C_1$-$C_{18}$-alkyl, $C_2$-$C_{18}$-alkenyl, and $C_2$-$C_{18}$-alkynyl are unsubstituted or bear one or more identical or different $Z^{3a}$ substituents,
$C_3$-$C_{12}$-cycloalkyl is unsubstituted or bears one or more identical or different $Z^{3b}$ substituents, and
$C_6$-$C_{14}$-aryl is unsubstituted or bears one or more identical or different $Z^{3Ar}$ substituents;
one of the $Z^{3*}$ substituents is cyano and the other $Z^{3*}$ substituent is $CO_2R^{39}$, $CONR^{310}R^{311}$, $C_1$-$C_{18}$-alkyl, $C_2$-$C_{18}$-alkenyl, $C_2$-$C_{18}$-alkynyl, $C_3$-$C_{12}$-cycloalkyl or $C_6$-$C_{14}$-aryl, where
$C_1$-$C_{18}$-alkyl, $C_2$-$C_{18}$-alkenyl, and $C_2$-$C_{18}$-alkynyl are unsubstituted or bear one or more identical or different $Z^{3a}$ substituents,
$C_3$-$C_{12}$-cycloalkyl is unsubstituted or bears one or more identical or different $Z^{3b}$ substituents, and
$C_6$-$C_{14}$-aryl is unsubstituted or bears one or more identical or different $Z^{3Ar}$ substituents;
$R^{31}$, $R^{32}$, $R^{33}$, $R^{34}$, $R^{35}$, $R^{36}$, $R^{37}$ and $R^{38}$ are each independently hydrogen, cyano, bromine or chlorine, with the proviso that 1, 2, 3, 4, 5, 6, 7 or 8 of the $R^{31}$, $R^{32}$, $R^{33}$, $R^{34}$, $R^{35}$, $R^{36}$, $R^{37}$ or $R^{38}$ substituents are cyano;
where
$R^{39}$ is hydrogen, $C_1$-$C_{10}$-alkyl, $C_2$-$C_{10}$-alkenyl, $C_2$-$C_{10}$-alkynyl, $C_3$-$C_{12}$-cycloalkyl or $C_6$-$C_{14}$-aryl, where
$C_1$-$C_{10}$-alkyl, $C_2$-$C_{10}$-alkenyl, and $C_2$-$C_{10}$-alkynyl are unsubstituted or bear one or more identical or different $R^{3a}$ substituents,
$C_3$-$C_{12}$-cycloalkyl is unsubstituted or bears one or more identical or different $R^{3b}$ substituents and
$C_6$-$C_{14}$-aryl is unsubstituted or bears one or more identical or different $R^{3Ar}$ substituents;
$R^{310}$ and $R^{311}$ are each independently hydrogen, $C_1$-$C_{10}$-alkyl, $C_2$-$C_{10}$-alkenyl, $C_2$-$C_{10}$-alkynyl, $C_3$-$C_{12}$-cycloalkyl or $C_6$-$C_{14}$-aryl, where
$C_1$-$C_{10}$-alkyl, $C_2$-$C_{10}$-alkenyl, and $C_2$-$C_{10}$-alkynyl are unsubstituted or bear one or more identical or different $R^{3a}$ substituents,
$C_3$-$C_{12}$-cycloalkyl is unsubstituted or bears one or more identical or different $R^{3b}$ substituents and
$C_6$-$C_{14}$-aryl is unsubstituted or bears one or more identical or different $R^{3Ar}$ substituents;
each $Z^{3a}$ is independently halogen, hydroxyl, $NR^{310a}R^{311a}$, $C_1$-$C_{10}$-alkoxy, $C_1$-$C_{10}$-haloalkoxy, $C_1$-$C_{10}$-alkylthio, $C_3$-$C_{12}$-cycloalkyl, $C_6$-$C_{14}$-aryl, $C(=O)R^{39a}$; $C(=O)OR^{39a}$ or $C(O)NR^{310a}R^{311a}$ where
$C_3$-$C_{12}$-cycloalkyl is unsubstituted or bears one or more identical or different $R^{3b}$ substituents and
$C_6$-$C_{14}$-aryl is unsubstituted or bears one or more identical or different $R^{3Ar}$ substituents;
each $Z^{3b}$ and each $Z^{3Ar}$ is independently halogen, hydroxyl, $NR^{310a}R^{311a}$, $C_1$-$C_{10}$-alkyl, $C_1$-$C_{10}$-alkoxy, $C_1$-$C_{10}$-haloalkoxy, $C_1$-$C_{10}$-alkylthio, $C(=O)R^{39a}$; $C(=O)OR^{39a}$ or $C(O)NR^{310a}R^{311a}$;
each $R^{3a}$ is independently halogen, hydroxyl, $C_1$-$C_{10}$-alkoxy, $C_3$-$C_{12}$-cycloalkyl or $C_6$-$C_{14}$-aryl;
each $R^{3b}$ is independently halogen, hydroxyl, $C_1$-$C_{10}$-alkyl, $C_1$-$C_{10}$-alkoxy, $C_1$-$C_{10}$-haloalkoxy, $C_1$-$C_{10}$-alkylthio, $C_2$-$C_{10}$-alkenyl, $C_2$-$C_{10}$-alkynyl, $C_3$-$C_{12}$-cycloalkyl or $C_6$-$C_{14}$-aryl;
each $R^{3Ar}$ is independently halogen, hydroxyl, $C_1$-$C_{10}$-alkyl, $C_1$-$C_{10}$-alkoxy, $C_1$-$C_{10}$-haloalkoxy, $C_1$-$C_{10}$-alkylthio, $C_2$-$C_{10}$-alkenyl, $C_2$-$C_{10}$-alkynyl, $C_3$-$C_{12}$-cycloalkyl or $C_6$-$C_{14}$-aryl;
$R^{39a}$ is hydrogen, $C_1$-$C_{10}$-alkyl, $C_2$-$C_{10}$-alkenyl, $C_2$-$C_{10}$-alkynyl, $C_3$-$C_{12}$-cycloalkyl or $C_6$-$C_{14}$-aryl; and
$R^{310a}$, $R^{311a}$ are each independently hydrogen, $C_1$-$C_{10}$-alkyl, $C_2$-$C_{10}$-alkenyl, $C_2$-$C_{10}$-alkynyl, $C_3$-$C_{12}$-cycloalkyl or $C_6$-$C_{14}$-aryl, (iii) a cyanated compound of formula (IV)

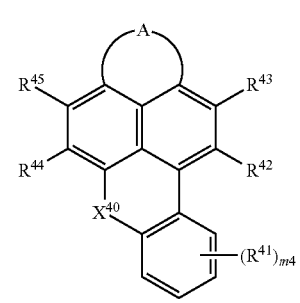

and a mixture thereof,
wherein
m4 is 0, 1, 2, 3 or 4;
each $R^{41}$ independently is bromine, chlorine, cyano, $-NR^{4a}R^{4b}$, $C_1$-$C_{24}$-alkyl, $C_1$-$C_{24}$-haloalkyl, $C_1$-$C_{24}$ alkoxy, $C_1$-$C_{24}$-haloalkoxy, $C_3$-$C_{24}$-cycloalkyl heterocycloalkyl, heteroaryl, $C_6$-$C_{24}$-aryl, $C_6$-$C_{24}$-aryloxy, or $C_6$-$C_{24}$-aryl-$C_1$-$C_{10}$-alkylene, where the rings of cycloalkyl, heterocycloalkyl, heteroaryl, aryl, aryloxy in $C_3$-$C_{24}$-cycloalkyl, heterocycloalkyl, heteroaryl, $C_6$-$C_{24}$-aryl, $C_6$-$C_{24}$-aryloxy, and $C_6$-$C_{24}$ aryl-$C_1$-$C_{10}$-alkylene are unsubstituted or substituted with 1, 2, 3, 4 or 5 identical or different radicals $R^{41a}$ and where $C_1$-$C_{24}$-alkyl, $C_1$-$C_{24}$-haloalkyl, $C_1$-$C_{24}$-alkoxy, and the alkylene moieties of $C_6$-$C_{24}$-aryl-$C_1$-$C_{10}$-alkylene are optionally interrupted by one or more groups selected from the group consisting of O, S and $NR^{4c}$;
at least one of the radicals $R^{42}$, $R^{43}$, $R^{44}$ and $R^{45}$ is CN, and the remaining radicals, independently from each other, are hydrogen, chlorine or bromine;
$X^{40}$ is O, S, SO or $SO_2$;

A is a diradical of formulae (A.1), (A.2), (A.3), or (A.4)

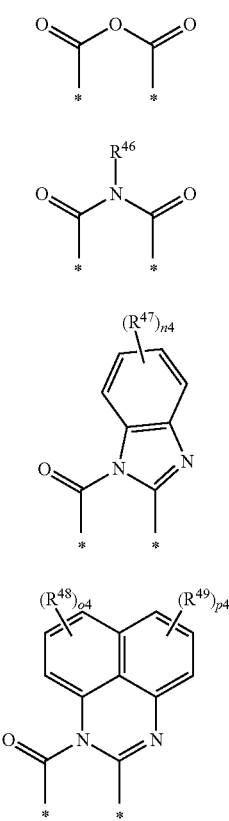

wherein
* in each case denotes a point of attachment to the remainder of the molecule;
n4 is 0, 1, 2, 3 or 4;
o4 is 0, 1, 2 or 3;
p4 is 0, 1, 2 or 3;
$R^{46}$ is hydrogen, $C_1$-$C_{24}$-alkyl, $C_1$-$C_{24}$-haloalkyl, $C_3$-$C_{24}$-cycloalkyl, $C_6$-$C_{24}$-aryl or $C_6$-$C_{24}$-aryl-$C_1$-$C_{10}$-alkylene, where the rings of cycloalkyl, aryl, and arylalkylene in $C_3$-$C_{24}$-cycloalkyl, $C_6$-$C_{24}$-aryl, and $C_6$-$C_{24}$-aryl-$C_1$-$C_{10}$-alkylene are unsubstituted or substituted with 1, 2, 3, 4 or 5 identical or different radicals $R^{46a}$, and where $C_1$-$C_{24}$-alkyl, $C_1$-$C_{24}$-haloalkyl and the alkylene moieties of $C_6$-$C_{24}$-aryl-$C_1$-$C_{10}$-alkylene are optionally interrupted by one or more heteroatoms or heteroatomic groups selected from the group consisting of O, S and $NR^{4c}$;
each $R^{47}$ independently is bromine, chlorine, cyano, —$NR^{4a}R^{4b}$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, or $C_6$-$C_{24}$-aryl-$C_1$-$C_{10}$-alkylene, where the rings of cycloalkyl, heterocycloalkyl, heteroaryl, aryl and arylalkylene in $C_3$-$C_{24}$-cycloalkyl, heterocycloalkyl, heteroaryl, $C_6$-$C_{24}$-aryl, $C_6$-$C_{24}$-aryloxy, and $C_6$-$C_{24}$-aryl-$C_1$-$C_{10}$-alkylene are unsubstituted or substituted with 1, 2, 3, 4 or 5 identical or different radicals $R^{47a}$ and where $C_1$-$C_{24}$-alkyl, $C_1$-$C_{24}$-haloalkyl, $C_1$-$C_{24}$-alkoxy, $C_1$-$C_{24}$-haloalkoxy, and the alkylene moieties of $C_6$-$C_{24}$-aryl-$C_1$-$C_{10}$-alkylene are optionally interrupted by one or more groups selected from the group consisting of O, S and $NR^{4c}$;
each $R^{48}$ independently is bromine, chlorine, cyano, $NR^{4a}R^{4b}$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, or $C_6$-$C_{24}$-aryl-$C_1$-$C_{10}$-alkylene, where the rings of cycloalkyl, heterocycloalkyl, heteroaryl, aryl and arylalkylene in $C_3$-$C_{24}$-cycloalkyl, heterocycloalkyl, heteroaryl, $C_6$-$C_{24}$-aryl, $C_6$-$C_{24}$-aryloxy, and $C_6$-$C_{24}$-aryl-$C_1$-$C_{10}$-alkylene are unsubstituted or substituted with 1, 2, 3, 4 or 5 identical or different radicals $R^{48a}$ and where $C_1$-$C_{24}$-alkyl, $C_1$-$C_{24}$-haloalkyl, $C_1$-$C_{24}$-alkoxy, $C_1$-$C_{24}$-haloalkoxy, and the alkylene moieties of $C_6$-$C_{24}$-aryl-$C_1$-$C_{10}$-alkylene are optionally interrupted by one or more groups selected from the group consisting of O, S and $NR^{4c}$;
each $R^{49}$ independently is selected from bromine, chlorine, cyano, $NR^{4a}R^{4b}$, $C_1$-$C_{24}$-alkyl, $C_1$-$C_{24}$-haloalkyl, $C_1$-$C_{24}$-alkoxy, $C_1$-$C_{24}$-haloalkoxy, $C_3$-$C_{24}$-cycloalkyl, heterocycloalkyl, heteroaryl, $C_6$-$C_{24}$-aryl, $C_6$-$C_{24}$-aryloxy, or $C_6$-$C_{24}$-aryl-$C_1$-$C_{10}$-alkylene, where the rings of cycloalkyl, heterocycloalkyl, heteroaryl, aryl and aryl-alkylene in $C_3$-$C_{24}$-cycloalkyl, heterocycloalkyl, heteroaryl, $C_6$-$C_{24}$-aryl, $C_6$-$C_{24}$-aryloxy, and $C_6$-$C_{24}$-aryl-$C_1$-$C_{10}$-alkylene are unsubstituted or substituted with 1, 2, 3, 4 or 5 identical or different radicals $R^{49a}$ and where $C_1$-$C_{24}$-alkyl, $C_1$-$C_{24}$-haloalkyl, $C_1$-$C_{24}$-alkoxy, $C_1$-$C_{24}$-haloalkoxy, and the alkylene moieties of $C_6$-$C_{24}$-aryl-$C_1$-$C_{10}$-alkylene are optionally interrupted by one or more groups selected from the group consisting of O, S and $NR^{4c}$;
$R^{41a}$, $R^{46a}$, $R^{47a}$, $R^{48a}$, $R^{49a}$ are independently $C_1$-$C_{24}$-alkyl, $C_1$-$C_{24}$-fluoroalkyl, $C_1$-$C_{24}$-alkoxy, fluorine, chlorine or bromine;
$R^{4a}$, $R^{4b}$, $R^{4c}$ are independently hydrogen, $C_1$-$C_{20}$-alkyl, $C_3$-$C_{24}$-cycloalkyl, heterocycloalkyl, heteroaryl or $C_6$-$C_{24}$-aryl;
(iv) a benzoxanthene compound of formula (V)

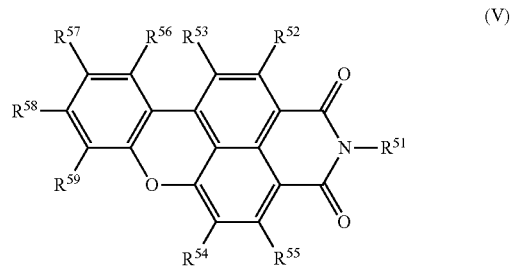

and a mixture thereof,
wherein
$R^{51}$ is phenyl which is unsubstituted or carries 1, 2, 3, 4, or 5 substituents selected from the group consisting of halogen, $R^{511}$, $OR^{552}$, $NHR^{552}$ and $NR^{552}R^{557}$;
$R^{52}$, $R^{53}$, $R^{54}$, $R^{55}$, $R^{56}$, $R^{57}$, $R^{58}$ and $R^{59}$ are independently hydrogen, halogen, $R^{553}$, $OR^{553}$, $NHR^{553}$ or $NR^{553}R^{554}$,
wherein
$R^{511}$ is $C_2$-$C_{18}$-alkyl, $C_6$-$C_{24}$-aryl or heteroaryl;
$R^{552}$ and $R^{557}$ are independently $C_1$-$C_{18}$-alkyl, $C_6$-$C_{24}$-aryl or heteroaryl; and $R^{553}$ and $R^{554}$ are independently $C_1$-$C_{18}$-alkyl, $C_6$-$C_{24}$-aryl or heteroaryl;

(v) a fluorescent compound comprising at least one structural unit of formula (VI)

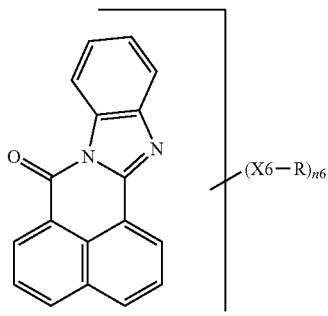
(VI)

where one or more CH groups of the six-membered ring of the benzimidazole structure shown are optionally replaced by nitrogen and where n6 is a number from 0 to (10-p6) for each structural unit of the formula (VI); where p6 is the number of CH units replaced by nitrogen in the six-membered ring of the benzimidazole structure, X6 is a chemical bond, O, S, SO, $SO_2$, or $NR^{61}$; and R is an aliphatic radical, cycloaliphatic radical, aryl, or heteroaryl, each of which optionally bears substituents,
is an aromatic or heteroaromatic ring or ring system, each of which is fused to other aromatic rings of the structural unit of the formula (VI), or
is F, Cl, Br, CN, or H when X6 is not a chemical bond;

where two R radicals are optionally joined to give one cyclic radical and where X6 and R, when n6>one, are the same or different;

each $R^{61}$ is independently hydrogen, $C_1$-$C_{18}$-alkyl or cycloalkyl, the carbon chain of which optionally comprises one or more of —O—, —S—, —CO—, —SO— and —$SO_2$— moieties and which are optionally mono- or polysubstituted; or
is aryl or heteroaryl which is optionally mono- or polysubstituted; and a mixture thereof;

(vi) a perylene compound of formulae (VII), (VIII), (IX) or (X)

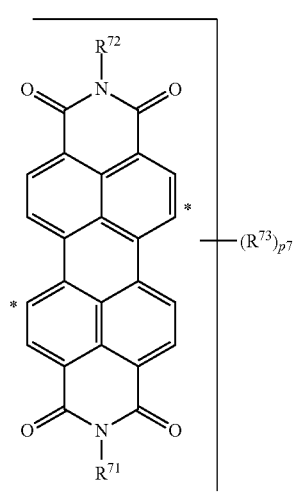
(VII)

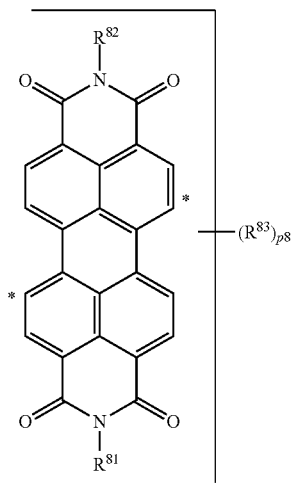
(VIII)

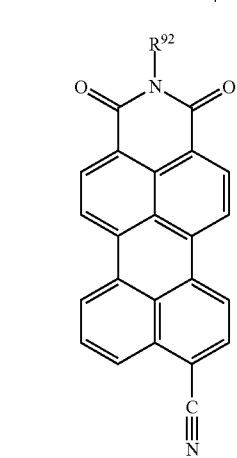
(IX)

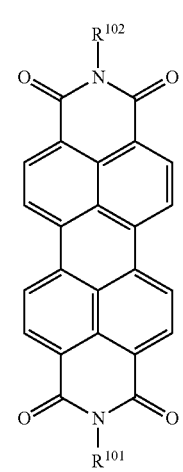
(X)

where
p7 is 2,
$R^{71}$, $R^{72}$ are each independently $C_1$-$C_{30}$-alkyl, $C_3$-$C_8$-cycloalkyl, aryl, heteroaryl, or aryl-$C_1$-$C_{10}$-alkylene, where the aromatic ring in aryl, heteroaryl, and aryl-$C_1$-$C_{10}$-alkylene is unsubstituted or mono- or polysubstituted by $C_1$-$C_{10}$-alkyl;
$R^{73}$ is aryloxy which is unsubstituted or mono- or polysubstituted by $C_1$-$C_{10}$-alkyl or $C_6$-$C_{10}$-aryl, where the $R^{73}$ radicals are at the positions indicated by *;
p8 is 2, $R^{81}$, $R^{82}$ are each independently $C_1$-$C_{30}$-alkyl, $C_3$-$C_8$-cycloalkyl, aryl, heteroaryl, or aryl-$C_1$-$C_{10}$-alkylene, where the aromatic ring in aryl, heteroaryl, and aryl-$C_1$-$C_{10}$-alkylene is unsubstituted or mono- or polysubstituted by $C_1$-$C_{10}$-alkyl;

$R^{83}$ is aryloxy which is unsubstituted or mono- or polysubstituted by $C_1$-$C_{10}$-alkyl or $C_6$-$C_{10}$-aryl, where the $R^{83}$ radicals are at the positions indicated by *;

$R^{92}$ is $C_1$-$C_{30}$-alkyl, $C_3$-$C_8$-cycloalkyl, aryl, heteroaryl, or aryl-$C_1$-$C_{10}$-alkylene, where the aromatic ring in aryl, heteroaryl, and aryl-$C_1$-$C_{10}$-alkylene is unsubstituted or mono- or polysubstituted by $C_1$-$C_{10}$-alkyl;

$R^{101}$, $R^{102}$ are each independently $C_1$-$C_{30}$-alkyl, $C_3$-$C_8$-cycloalkyl, aryl, heteroaryl, or aryl-$C_1$-$C_{10}$-alkylene, where the aromatic ring in aryl, heteroaryl, and aryl-$C_1$-$C_{10}$-alkylene is unsubstituted or mono- or polysubstituted by $C_1$-$C_{10}$-alkyl;

(vii) a perylene bisimide compound of formula (XI)

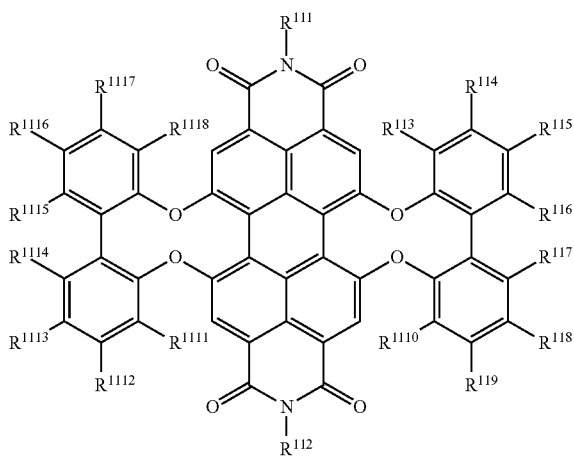

(XI)

and a mixture thereof,
wherein
$R^{111}$ and $R^{112}$, independently are hydrogen, an unsubstituted or a substituted $C_1$-$C_{30}$-alkyl, an unsubstituted or a substituted polyalkyleneoxy, an unsubstituted or a substituted $C_1$-$C_{30}$-alkoxy, an unsubstituted or a substituted $C_1$-$C_{30}$-alkylthio, an unsubstituted or a substituted $C_3$-$C_{20}$-cycloalkyl, an unsubstituted or a substituted $C_3$-$C_{20}$-cycloalkyloxy, an unsubstituted or a substituted $C_6$-$C_{24}$-aryl or an unsubstituted or a substituted $C_6$-$C_{24}$-aryloxy;

$R^{113}$, $R^{114}$, $R^{115}$, $R^{116}$, $R^{117}$, $R^{118}$, $R^{119}$, $R^{1110}$, $R^{1111}$, $R^{1112}$, $R^{1113}$, $R^{1114}$, $R^{1115}$, $R^{1116}$, $R^{1117}$ and $R^{1118}$ independently are hydrogen, halogen, cyano, hydroxyl, mercapto, nitro, —$NE^{111}E^{112}$, —$NR^{Ar111}COR^{Ar112}$, —$CONR^{Ar111}R^{Ar112}$, —$SO_2NR^{Ar111}R^{Ar112}$, —$COOR^{Ar111}$, —$SO_3R^{Ar112}$, an unsubstituted or a substituted $C_1$-$C_{30}$-alkyl, an unsubstituted or a substituted polyalkyleneoxy, an unsubstituted or a substituted $C_1$-$C_{30}$-alkoxy, an unsubstituted or a substituted $C_1$-$C_{30}$-alkylthio, an unsubstituted or a substituted $C_3$-$C_{20}$-cycloalkyl, an unsubstituted or a substituted $C_3$-$C_{20}$-cycloalkoxy, an unsubstituted or a substituted $C_6$-$C_{24}$-aryl, an unsubstituted or a substituted $C_6$-$C_{24}$-aryloxy or an unsubstituted or a substituted $C_6$-$C_{24}$-arylthio, where $R^{113}$ and $R^{1144}$, $R^{114}$ and $R^{115}$, $R^{115}$ and $R^{116}$, $R^{116}$ and $R^{117}$, $R^{117}$ and $R^{118}$, $R^{118}$ and $R^{119}$, $R^{119}$ and $R^{1110}$, $R^{1111}$ and $R^{1112}$, $R^{1112}$ and $R^{1113}$, $R^{1113}$ and $R^{1114}$, $R^{1114}$ and $R^{1115}$, $R^{1115}$ and $R^{1116}$, $R^{1116}$ and $R^{1117}$ and/or $R^{1117}$ and $R^{1118}$ together with the carbon atoms of the biphenylyl moiety to which they are bonded, optionally form a further fused aromatic or non-aromatic ring system wherein the fused ring system is unsubstituted or substituted;

where
$E^{111}$ and $E^{112}$, independently are hydrogen, an unsubstituted or a substituted $C_1$-$C_{18}$-alkyl, an unsubstituted or a substituted $C_2$-$C_{18}$-alkenyl, an unsubstituted or a substituted $C_2$-$C_{18}$-alkynyl, an unsubstituted or a substituted $C_3$-$C_{20}$-cycloalkyl, or an unsubstituted or a substituted $C_6$-$C_{10}$-aryl;

$R^{Ar111}$ and $R^{Ar112}$, each independently are hydrogen, an unsubstituted or a substituted $C_1$-$C_{18}$-alkyl, an unsubstituted or a substituted $C_3$-$C_{20}$-cycloalkyl, an unsubstituted or a substituted heterocyclyl, an unsubstituted or a substituted $C_6$-$C_{20}$-aryl or an unsubstituted or a substituted heteroaryl;

and
a mixture thereof.

9. The color converter of claim 8, wherein the at least one further organic fluorescent dye is a fluorescent compound comprising at least one structural unit of formula (VI).

10. A method for converting light, the method comprising:
converting light generated by a blue LED with a center wavelength of emission between 420 nm and 480 nm via the color converter of claim 6 into light of a second, longer wavelength.

11. A method for converting light, the method comprising:
converting light generated by a cool white LED having a correlated color temperature between 6000 K and 20000 K via the color converter of claim 6 so as to provide white light having a lower correlated color temperature.

12. A lighting device, comprising:
at least one light emitting diode (LED) selected from the group consisting of a blue LED with a center wavelength of emission from 420 nm to 480 nm and a cool white LED having a correlated color temperature between 6000 K and 20000 K; and
(ii) at least one color converter of claim 6,
wherein the at least one color converter is in a remote arrangement from the at least one LED.

13. A color converter, comprising:
the perylene bisimide compound of the formula I of claim 1 or a mixture thereof.

14. A security ink, comprising
the perylene bisimide compound of the formula (I) of claim 1 or a mixture thereof.

15. A printing ink formulation for security printing, comprising
at least one compound of the formula (I) of claim 1 or a mixture thereof.

16. A printing ink formulation of claim 15, further comprising
a polymeric binder;
optionally an organic solvent;
optionally at least one colorant; and
optionally at least one further additive.

* * * * *